(12) United States Patent
Baumann et al.

(10) Patent No.: US 9,985,225 B2
(45) Date of Patent: May 29, 2018

(54) HETEROLEPTIC COPPER COMPLEXES FOR OPTOELECTRONIC USES

(71) Applicant: CYNORA GMBH, Bruchsal (DE)

(72) Inventors: Thomas Baumann, Karlsruhe (DE); Tobias Grab, Karlsruhe (DE); Daniel Volz, Karlsruhe (DE); Daniel Zink, Bruchsal (DE)

(73) Assignee: CYNORA GMBH, Bruchsal (DE)

( * ) Notice: Subject to any disclaimer, the term of this patent is extended or adjusted under 35 U.S.C. 154(b) by 691 days.

(21) Appl. No.: 14/357,805

(22) PCT Filed: Nov. 16, 2012

(86) PCT No.: PCT/EP2012/072927
§ 371 (c)(1),
(2) Date: May 13, 2014

(87) PCT Pub. No.: WO2013/072508
PCT Pub. Date: May 23, 2013

(65) Prior Publication Data
US 2014/0326981 A1    Nov. 6, 2014

(30) Foreign Application Priority Data

Nov. 16, 2011 (EP) .................... 11189397
Dec. 21, 2011 (EP) .................... 11195010

(51) Int. Cl.
| | | |
|---|---|---|
| H01L 51/54 | (2006.01) |
| C09K 11/06 | (2006.01) |
| C07F 1/08 | (2006.01) |
| H01L 51/00 | (2006.01) |
| C07F 9/50 | (2006.01) |
| C07F 9/6506 | (2006.01) |
| C07F 9/6518 | (2006.01) |
| C07F 9/653 | (2006.01) |
| C07F 9/6539 | (2006.01) |
| H01L 51/05 | (2006.01) |
| H01L 51/42 | (2006.01) |
| H01L 51/56 | (2006.01) |
| H01L 51/50 | (2006.01) |

(52) U.S. Cl.
CPC ............ *H01L 51/0091* (2013.01); *C07F 1/08* (2013.01); *C07F 9/5022* (2013.01); *C07F 9/5027* (2013.01); *C07F 9/5045* (2013.01); *C07F 9/6539* (2013.01); *C07F 9/65066* (2013.01); *C07F 9/65068* (2013.01); *C07F 9/65186* (2013.01); *C07F 9/65312* (2013.01); *C09K 11/06* (2013.01); *H01L 51/009* (2013.01); *H01L 51/0508* (2013.01); *H01L 51/42* (2013.01); *H01L 51/56* (2013.01); *C09K 2211/1033* (2013.01); *C09K 2211/1037* (2013.01); *C09K 2211/1044* (2013.01); *C09K 2211/1048* (2013.01); *C09K 2211/1051* (2013.01); *C09K 2211/1059* (2013.01); *C09K 2211/188* (2013.01); *H01L 51/5012* (2013.01); *H01L 51/5016* (2013.01); *Y02E 10/549* (2013.01); *Y02P 70/521* (2015.11)

(58) Field of Classification Search
None
See application file for complete search history.

(56) References Cited

U.S. PATENT DOCUMENTS

| | | | |
|---|---|---|---|
| 6,989,273 B2 | 1/2006 | Hsieh et al. | |
| 7,413,818 B2 * | 8/2008 | Tsuboyama et al. | .. C09K 11/06 257/E51.041 |
| 2002/0179885 A1 | 12/2002 | Che et al. | |
| 2003/0186080 A1 | 10/2003 | Kamatani et al. | |
| 2003/0205707 A1 | 11/2003 | Chi-Ming | |
| 2005/0079384 A1 * | 4/2005 | Tsuboyama et al. | .. C09K 11/06 428/690 |
| 2006/0073360 A1 | 4/2006 | Ise et al. | |
| 2006/0105202 A1 | 5/2006 | Kitamura | |

(Continued)

FOREIGN PATENT DOCUMENTS

| | | |
|---|---|---|
| DE | 10338550 A1 | 3/2005 |
| DE | 10350606 A1 | 6/2005 |
| DE | 10358665 A1 | 7/2005 |

(Continued)

OTHER PUBLICATIONS

International Search Report for PCT/EP2012/072927 dated Apr. 2, 2013.

(Continued)

*Primary Examiner* — Marie R. Yamnitzky
(74) *Attorney, Agent, or Firm* — Ryan, Mason & Lewis, LLP

(57) ABSTRACT

A heteroleptic binuclear copper(I) complex of the $Cu_2X_2$(E∩N*)$L_2$ form, having a structure of formula A:

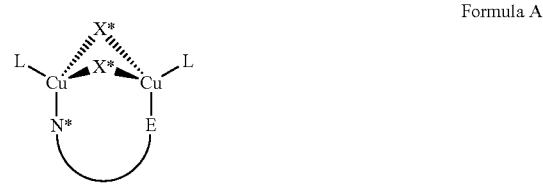

Formula A

The copper(I) complex may be used in optoelectronic components, particularly for use in organic light emitting diodes (OLEDs).

15 Claims, 19 Drawing Sheets

(56) References Cited

U.S. PATENT DOCUMENTS

2012/0184738 A1* 7/2012 Yersin et al. ............ C07F 1/005 544/225
2014/0183490 A1 7/2014 Baumann et al.

FOREIGN PATENT DOCUMENTS

| JP | 2005-129499 A | * | 5/2005 |
| JP | 2014527030 A | | 10/2014 |
| WO | 03095587 A1 | | 11/2003 |
| WO | 2004016711 A1 | | 2/2004 |
| WO | 2004017043 A2 | | 2/2004 |
| WO | 2006003000 A1 | | 1/2006 |
| WO | 2006028546 A1 | | 3/2006 |
| WO | 2006032449 A1 | | 3/2006 |
| WO | 2010149748 A1 | | 12/2010 |

OTHER PUBLICATIONS

C. Adachi et al., "High-Efficiency Red Electrophosphorescence Devices," Applied Physics Letters, Mar. 2001, pp. 1622-1624, vol. 78, No. 11.

X. Yang et al., "Highly Efficient Polymeric Electrophosphorescent Diodes," Advanced Materials, Apr. 2006, pp. 948-954, vol. 18, No. 7.

X.H. Yang et al. "Polymer Electrophosphorescence Devices with High Power Conversion Efficiencies," Applied Physics Letters, 2004, pp. 2476-2478, vol. 84, No. 14.

Hartmut Yersin, "Triplet Emitters for OLED Applications, Mechanisms of Exciton Trapping and Control of Emission Properties," Topics in Current Chemistry, 2004, pp. 1-26, vol. 241.

Zakya Kafafi, "Organic Electroluminescence," Taylor & Francis, May 2005, 499 pages.

P.C. Ford et al., "Photoluminescence Properties of Multinuclear Copper(I) Compounds," Chemical Reviews, Dec. 1999, pp. 3625-3647, vol. 99, No. 12.

A. Rossler et al., "Customized Materials—Nanoparticles: Materials of the Future," Chemie in Unserer Zeit, Jan. 2001, pp. 32-41, vol. 35, No. 1.

Y. Sun et al., "Luminescent One-Dimensional Nanoscale Materials with PtII . . . PtII Interactions," Angewandte Chemie, Aug. 2006, pp. 5738-5741, vol. 118, No. 34.

Y. Chen et al., "Nanoporous Carbon Produced by Ball Milling," Applied Physics Letters, May 1999, pp. 2782-2784, vol. 74, No. 19.

Hartmut Yersin, "Highly Efficient OLEDs with Phosphorescent Materials," Wiley-VCH Verlag GmbH & Co. KGaA, Jan. 2008, 457 pages.

* cited by examiner

27 555 nm

28 499 nm

31 540 nm

32 554 nm

33 535 nm

34 544 nm

35 540 nm

36 551 nm

HETEROLEPTIC COPPER COMPLEXES FOR OPTOELECTRONIC USES

FIELD OF THE INVENTION

The invention relates to heteroleptic copper(I) complexes of the general formula A, in particular for use in optoelectronic components.

BACKGROUND OF THE INVENTION

A dramatic change is currently on the horizon in the sector of visual display unit and illumination technology. It will be possible to manufacture flat displays or illuminated surfaces with a thickness of less than 0.5 mm. These are notable for many fascinating properties. For example, it will be possible to achieve illuminated surfaces in the form of wallpaper with very low energy consumption. In addition, color visual display units with hitherto unachievable trueness of color, brightness and viewing angle independence will be producible with low weight and very low power consumption. The visual display units will be configurable as microdisplays or large visual display units of several $m^2$ in area, in rigid or flexible form, or else as transmission or reflection displays. In addition, it will be possible to use simple and inexpensive production processes such as screen printing or inkjet printing or vacuum sublimation. This will enable very inexpensive manufacture compared to conventional flat visual display units. This new technology is based on the principle of OLEDs, Organic Light Emitting Diodes, which is shown schematically and in simplified form in FIG. 36.

Such components consist predominantly of organic layers, as shown schematically and in simplified form in FIG. 36. At a voltage of, for example, 5 V to 10 V, negative electrons pass from a conductive metal layer, for example from an aluminum cathode, into a thin electron conduction layer and migrate in the direction of the positive anode. This consists, for example, of a transparent but electrically conductive thin indium tin oxide layer, from which positive charge carriers, called holes, migrate into an organic hole conduction layer. These holes move in the opposite direction compared to the electrons, specifically toward the negative cathode. In a middle layer, the emitter layer, which likewise consists of an organic material, there are additionally special emitter molecules where, or close to which, the two charge carriers recombine and lead to uncharged but energetically excited states of the emitter molecules. The excited states then release their energy as bright emission of light, for example in a blue, green or red color. White light emission is also achievable. In some cases, it is also possible to dispense with the emitter layer when the emitter molecules are present in the hole or electron conduction layer.

The novel OLED components can be configured with a large area as illumination bodies, or else in exceptionally small form as pixels for displays. A crucial factor for the construction of highly effective OLEDs is the luminous materials used (emitter molecules). These can be implemented in various ways, using purely organic or organometallic molecules, and complexes. It can be shown that the light yield of the OLEDs can be much greater with organometallic substances, called triplet emitters, than for purely organic materials. Due to this property, the further development of the organometallic materials is of high significance. The function of OLEDs has been described very frequently.[i-vi] Using organometallic complexes with high emission quantum yield (transitions including the lowermost triplet states to the singlet ground states), it is possible to achieve a particularly high efficiency of the device. These materials are frequently referred to as triplet emitters or phosphorescent emitters. This has been known for some time.[i-v] For triplet emitters, many property rights have already been applied for and granted.[vii-xix]

Copper complexes of the $Cu_2X_2L_4$, $Cu_2X_2L'_2$ and $Cu_2X_2L_2L'$ form (L=phosphane, amine, imine ligand; L'=bidentate phosphane, imine, amine ligand, see below) are already known in the prior art. They exhibit intense luminescence on excitation with UV light. The luminescence can originate either from an MLCT, CC (cluster centered) or XLCT (halogen-to-ligand charge transfer) state, or a combination thereof. Further details of similar Cu(I) systems can be found in the literature.[xx] In the case of the related $[Cu_2X_2(PPh_3)_2nap]$ complex (nap=1,8-naphthyridine, X=Br, I), a transition between the molecular orbital of the $\{Cu_2X_2\}$ unit (Cu d and halogen p orbitals) and the $\pi^*$ orbitals of the nap group is discussed.[xxi]

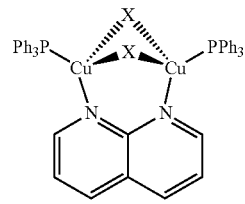

Example of a structure of the complexes of the $Cu_2X_2L_2L'$ form (L = $PPh_3$, L' = 1,8-naphthyridine, X = Br, I)

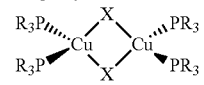

Example of complexes of the $Cu_2X_2L_4$ form (L = $PR_3$, X = Cl, Br, or I)

Triplet emitters have great potential for the generation of light in displays (as pixels) and in illuminated surfaces (for example, as luminous wallpaper). Very many triplet emitter materials have already been patented and are now also being used technologically in first devices. The solutions to date have disadvantages and problems, specifically in the following areas:

long-term stability of the emitters in the OLED devices,
thermal stability,
chemical stability to water and oxygen,
availability of important emission colors,
manufacturing reproducibility,
achievability of high efficiency at high current densities,
achievability of very high luminances,
high cost of the emitter materials,
emitter materials are toxic and
syntheses are complex.

Accordingly, it was an object of the present invention to overcome at least some of the abovementioned disadvantages.

BRIEF DESCRIPTION OF THE DRAWINGS

Exemplary embodiments of the present invention will be described below in more detail, with reference to the accompanying drawings, of which.

DETAILED DESCRIPTION OF EXEMPLARY EMBODIMENTS OF THE INVENTION

Figure 1A:
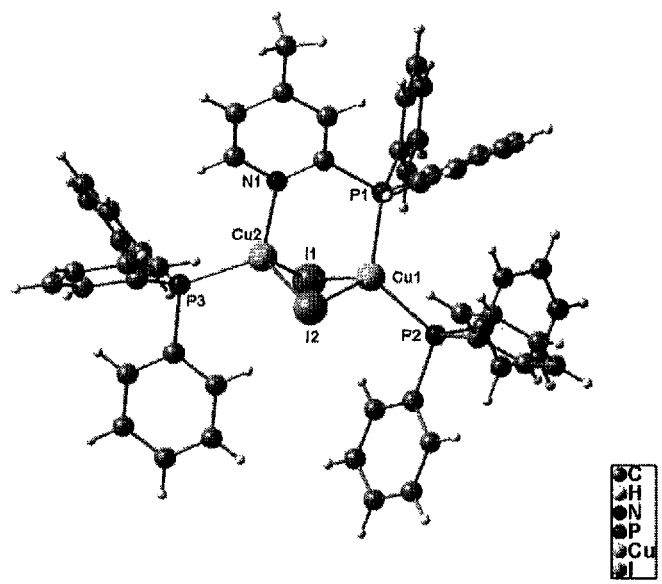
FIG. 1A shows the crystal structure of compound 1 in accordance with an embodiment of the present invention.

Exemplary embodiments of the invention will now be discussed in further detail. This invention may, however, be embodied in many different forms and should not be construed as limited to the embodiments set forth herein.

The problem underlying the invention is solved by the provision of heteroleptic binuclear copper(I) complexes of the $Cu_2X_2(E\cap N^*)L_2$ form, which comprise a structure according to formula A or have a structure of the formula A:

Formula A

In formula A (subsequently also referred to as $Cu_2X_2(E\cap N^*)L_2$), $E\cap N^*$ stands for a chelating N-heterocyclic ligand that binds to the $Cu_2X_2$ core via a nitrogen atom and either a phosphorus, arsenic or antimony atom, and L, independently form each other, for a phosphane, arsane or antimony ligand, wherein both ligands L can also be connected to each other such that a bidentate ligand results, or wherein one ligand L or both ligands L can also be connected to E∩N* such that a tridentate or tetradentate ligand results. At least one L is dissimilar to E∩N*.

Special embodiments of the binuclear copper(I) complexes according to the invention of formula A are illustrated by formulas I and II and III and are explained below.

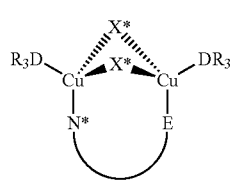

Formula I

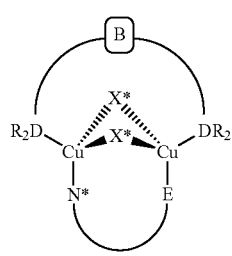

Formula II

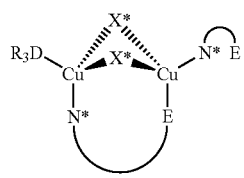

Formula III with:
- X*=Cl, Br, I, CN, OCN, SCN, alkynyl and/or $N_3$ (i.e. independently from each other, so that the complex can comprise two identical or two different atoms X*),
- N*∩E=independently from each other bidentate ligands with E=phosphinyl/arsenyl/antimonyl group of the $R_2E$ form (R=alkyl, aryl, heteroaryl, alkoxyl, phenoxyl, amide); N*=imine function.
- "∩" is a carbon atom. E is in particular a $Ph_2P$ group (Ph=phenyl), the imine function is part of an aromatic group (e.g. pyridyl, pyridazinyl, pyrimidyl, pyrazinyl, triazinyl, tetrazinyl, oxazolyl, thiazolyl, imidazolyl, pyrazolyl, isoxazolyl, isothiazolyl, 1,2,3-triazolyl, 1,2,4-triazolyl, 1,2,4-oxadiazolyl, 1,2,4-thiadiazolyl, tetrazolyl, 1,2,3,4-oxatriazolyl, 1,2,3,4-thiatriazolyl, chinolyl, isochinolyl, chinoxalyl, chinazolyl, etc.), which is optionally further substituted and/or annulated.
- "∩" is likewise part of this aromatic group. The carbon atom is directly adjacent both to the imine nitrogen atom and to the E atom.
- D=independently from each other P and/or As and/or Sb.
- R=each independently hydrogen, halogen or substituents, which are bound via oxygen (—OR), nitrogen (—$NR_2$) or silicon atoms (—$SiR_3$) as well as alkyl (also branched or cyclic), heteroalkyl, aryl, heteroaryl, alkenyl, alkynyl groups or substituted alkyl (also branched or cyclic), heteroalkyl, aryl, heteroaryl and alkenyl groups with substituents such as halogens or deuterium, alkyl groups (also branched or cyclic), heteroalkyl, aryl, heteroaryl and further generally known donor and acceptor groups such as for example amines, carboxylates and their esters and $CF_3$ groups. The rests R can optionally also lead to annulated ring systems.
- N*∩E and/or L can optionally be substituted, especially by groups which improve the charge carrier transport and/or groups which increase solubility of the copper(I) complex in the standard organic solvents for OLED component production. Standard organic solvents include, as well as alcohols, ethers, alkanes and halogenated aliphatic and aromatic hydrocarbons and alkylated aromatic hydrocarbons, especially toluene, chlorobenzene, dichlorobenzene, mesitylene, xylene, tetrahydrofuran, phenetole, propiophenone.

A copper(I) complex according to the invention consists in one embodiment of one bidentate ligand N*∩E and either two identical monodentate ligands $DR_3$ or two different monodentate ligands $DR_3$, wherein a ligand can be identical or different to N*∩E or a bidentate ligand $R_2D$-B-$DR_2$, whereby different functionalities can be introduced via the periphery of the different ligands (for example, one hole transport unit and one electron transport unit each, referred to below as hole conductor and electron conductor, respectively) and thus, an optimum charge carrier transport to and a well-defined recombination directly on the copper complex is ensured. The great advantage in the case of use of copper as the central metal is the low cost thereof, in particular compared to the metals such as Re, Os, Ir and Pt which are otherwise customary in OLED emitters. In addition, the low toxicity of copper reason in favor of its use.

With regard to its use in optoelectronic components, the copper(I) complexes according to the invention are notable for a wide range of achievable emission colors. In addition, the emission quantum yield is high, in particular greater than 50%. For emitter complexes with a Cu central ion, the emission decay times are astonishingly short.

In addition, the copper(I) complexes according to the invention are usable in relatively high emitter concentrations without notable quenching effects. This means that emitter concentrations of 5% to 100% can be used in the emitter layer.

Preferably, the ligand N*∩E comprises the following ligands:

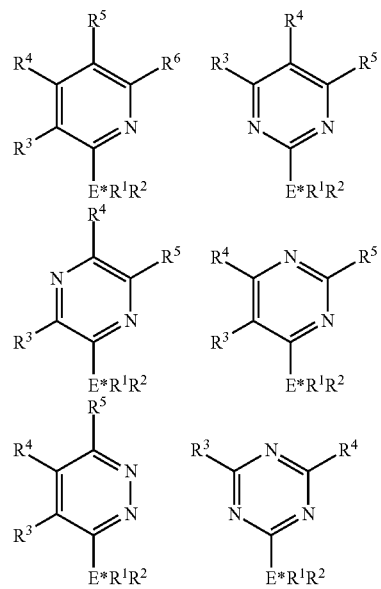

-continued

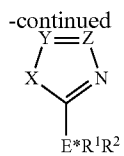

X = NR³, Y = CR⁴, Z = CR⁵: 2E*R¹R²-1R³-4R⁵-5R⁴-1H-Imidazole
X = NR³, Y = N, Z = CR⁴: 5E*R¹R²-1R³-3R⁴-1H-1,2,4-Triazole
X = NR³, Y = CR⁴, Z = N: 3E*R¹R²-4R³-5R⁴-4H-1,2,4-Triazole
X = NR³, Y = N, Z = N: 5E*R¹R²-1R³-1H-Tetrazole
X = O, Y = CR³, Z = CR⁴: 2E*R¹R²-4R⁴-5R³-Oxazole
X = O, Y = N, Z = CR³: 5E*R¹R²-3R³-1,2,4-Oxadiazole
X = O, Y = CR³, Z = N: 2E*R¹R²-5R³-1,3,4-Oxadiazole
X = O, Y = N, Z = N: 5E*R¹R²-1,2,3,4-Oxatriazole
X = S, Y = CR³, Z = CR⁴: 2E*R¹R²-4R⁴-5R³-Thiazole
X = S, Y = N, Z = CR³: 5E*R¹R²-3R³-1,2,4-Thiadiazole
X = S, Y = CR³, Z = N: 2E*R¹R²-5R³-1,3,4-Thiadiazole
X = S, Y = N, Z = N: 5E*R¹R²-1,2,3,4-Thiatriazole

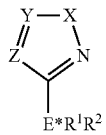

X = NR³, Y = CR⁴, Z = CR⁵: 3E*R¹R²-1R³-4R⁵-5R⁴-1H-Pyrazole
X = NR³, Y = N, Z = CR⁴: 4E*R¹R²-2R³-5R⁴-2H-1,2,3-Triazole
X = NR³, Y = CR⁴, Z = N: 3E*R¹R²-1R³-5R⁴-1H-1,2,4-Triazole
X = NR³, Y = N, Z = N: 5E*R¹R²-2R³-2H-Tetrazole
X = O, Y = CR³, Z = CR⁴: 3E*R¹R²-4R⁴-5R³-Isoxazole
X = O, Y = N, Z = CR³: 3E*R¹R²-4R³-1,2,5-Oxadiazole
X = O, Y = CR³, Z = N: 3E*R¹R²-5R³-1,2,4-Oxadiazole
X = O, Y = N, Z = N: 4E*R¹R²-1,2,3,5-Oxatriazole
X = S, Y = CR³, Z = CR⁴: 3E*R¹R²-4R⁴-5R³-Isothiazole
X = S, Y = N, Z = CR³: 3E*R¹R²-4R³-1,2,5-Thiadiazole
X = S, Y = CR³, Z = N: 3E*R¹R²-5R³-1,2,4-Thiadiazole
X = S, Y = N, Z = N: 4E*R¹R²-1,2,3,5-Thiatriazole

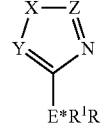

X = NR³, Y = CR⁴, Z = CR⁵: 4E*R¹R²-1R³-2R⁵-5R⁴-1H-Imidazole
X = NR³, Y = N, Z = CR⁴: 3E*R¹R²-1R³-5R⁴-1H-1,2,4-Triazole
X = NR³, Y = CR⁴, Z = N: 4E*R¹R²-1R³-5R⁴-1H-1,2,3-Triazole
X = NR³, Y = N, Z = N: 5E*R¹R²-2R³-2H-Tetrazole
X = O, Y = CR³, Z = CR⁴: 4E*R¹R²-2R⁴-5R³-Oxazole
X = O, Y = N, Z = CR³: 3E*R¹R²-5R³-1,2,4-Oxadiazole
X = O, Y = CR³, Z = N: 4E*R¹R²-5R³-1,2,3-Oxadiazole
X = O, Y = N, Z = N: 4E*R¹R²-1,2,3,5-Oxatriazole
X = S, Y = CR³, Z = CR⁴: 4E*R¹R²-2R⁴-5R³-Thiazole
X = S, Y = N, Z = CR³: 3E*R¹R²-5R³-1,2,4-Thiadiazole
X = S, Y = CR³, Z = N: 4E*R¹R²-5R³-1,2,3-Thiadiazole
X = S, Y = N, Z = N: 4E*R¹R²-1,2,3,5-Thiatriazole with
E*=independently from each other P, As or Sb,
X=independently from each other NR³, O or S,
Y=independently from each other CR³, CR⁴ or N,
Z=independently from each other CR⁴, CR⁵ or N,
R¹-R⁶ can each independently from each other be hydrogen, halogen or substituents, which are bound via oxygen (—OR), nitrogen (—NR₂) or silicon atoms (—SiR₃) as well as alkyl (also branched or cyclic), heteroalkyl, aryl, heteroaryl, alkenyl, alkynyl groups or substituted alkyl (also branched or cyclic), heteroalkyl, aryl, heteroaryl and alkenyl groups with substituents such as halogens or deuterium, alkyl groups (also branched or cyclic), heteroalkyl, aryl, heteroaryl and further generally known donor and acceptor groups such as for example amines, carboxylates and their esters and CF₃ groups. R³-R⁶ can optionally also lead to annulated ring systems.

Preferably, the ligand DR₃ (see formula I) comprises the following ligands:
monodentate ligands with
D=independently from each other P, As or Sb,
R₃ can each independently from each other be hydrogen, halogen or substituents, which are bound via oxygen (—OR), nitrogen (—NR₂) or silicon atoms (—SiR₃) as well as alkyl (also branched or cyclic), heteroalkyl, aryl, heteroaryl, alkenyl, alkynyl groups or substituted alkyl (also branched or cyclic), heteroalkyl, aryl, heteroaryl and alkenyl groups with substituents such as halogens or deuterium, alkyl groups (also branched or cyclic), heteroalkyl, aryl, heteroaryl and further generally known donor and acceptor groups such as for example amines, carboxylates and their esters and CF₃ groups. The three individual groups R can optionally also lead to annulated ring systems.

Preferably, the ligand R₂D-B-DR₂ (see formula II) is a ligand with the following characteristics:
bidentate ligands with
D=independently from each other P, As or Sb,
R₂ can each independently from each other be hydrogen, halogen or substituents, which are bound via oxygen (—OR), nitrogen (—NR₂) or silicon atoms (—SiR₃) as well as alkyl (also branched or cyclic), heteroalkyl, aryl, heteroaryl, alkenyl, alkynyl groups or substituted alkyl (also branched or cyclic), heteroalkyl, aryl, heteroaryl and alkenyl groups with substituents such as halogens or deuterium, alkyl groups (also branched or cyclic), heteroalkyl, aryl, heteroaryl and further generally known donor and acceptor groups such as for example amines, carboxylates and their esters and CF₃ groups, which are bound to another group D via a bridge B and thus form a bidentate ligand, wherein the bridge B is a direct bond or a substituted or unsubstituted alkylene, alkenylene, alkynylene or arylene group or a combination of both, or —O—, —NR— or —SiR₂—, wherein each R is, independently from each other, selected from the group consisting of hydrogen, halogen or substituents, which are bound via oxygen (—OR), nitrogen (—NR₂) or silicon atoms (—SiR₃) as well as alkyl (also branched or cyclic), heteroalkyl, aryl, heteroaryl, alkenyl, alkynyl groups or substituted alkyl (also branched or cyclic), heteroalkyl, aryl, heteroaryl and alkenyl groups with substituents such as halogens or deuterium, alkyl groups (also branched or cyclic), heteroalkyl, aryl, heteroaryl and further generally known donor and acceptor groups, such as, for example, amines, carboxylates and their esters as well as CF₃ groups. The two individual groups R can also lead to annulated ring systems.

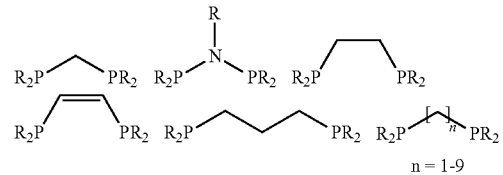

n = 1-9

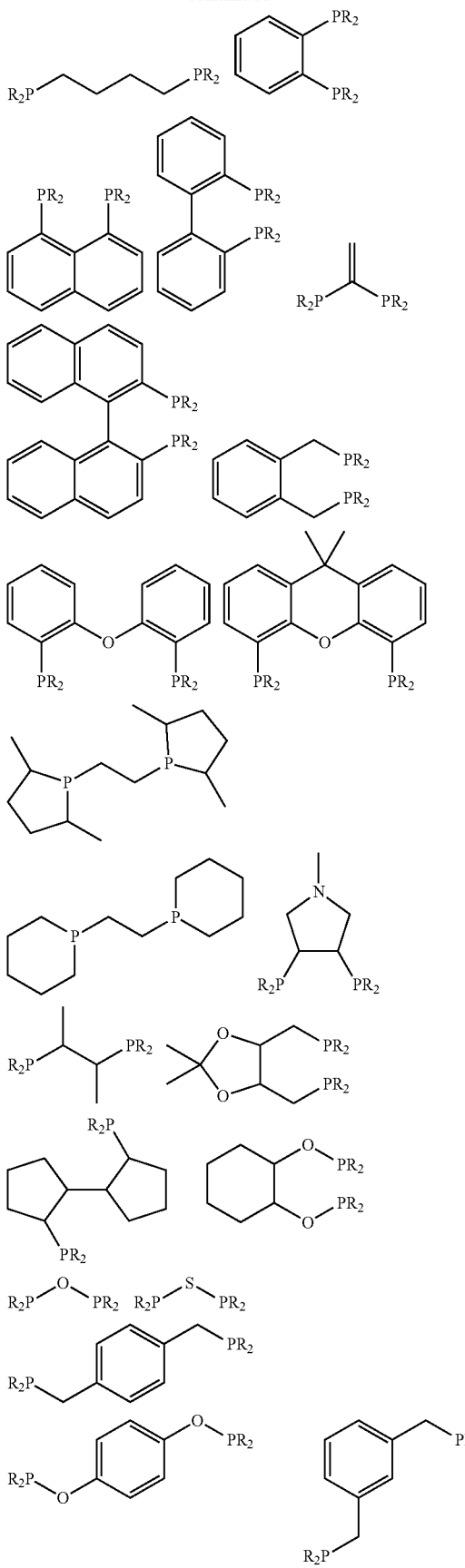
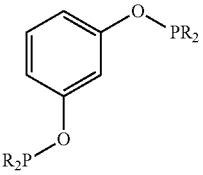

The bidentate ligand N*∩E as well as the two monodentate ligands DR$_3$ or the bidentate ligand R$_2$D-B-DR$_2$ can be substituted at suitable positions with at least one function group FG. That way, direct $C_{FG}$—$C_{N^*\cap E}$ bonds can be formed, wherein $C_{N^*\cap E}$ represents a C atom of the ligand N*∩E and $C_{FG}$ represents a C atom of the function group. If the binding atom is a nitrogen atom, $N_{FG}$—$C_{N^*\cap E}$ bonds will result, wherein $N_{FG}$ stands for the nitrogen atom. On the other hand, the function group can be linked to the N*∩E ligand via a bridge, wherein the bridge is, e.g. ether, thioether, ester, amide, methylene, silane, ethylene, or ethine bridges. Thereby, for example, the following functions can result as bridges: $C_{FG}$—O—$C_{N^*\cap E}$, $C_{FG}$—S—$C_{N^*\cap E}$, $C_{FG}$—C(O)—O—$C_{N^*\cap E}$, $C_{FG}$—C(O)—NH—$C_{N^*\cap E}$, $C_{FG}$—CH$_2$—$C_{N^*\cap E}$, $C_{FG}$—SiR'$_2$—$C_{N^*\cap E}$, $C_{FG}$—CH=CH—$C_{N^*\cap E}$, $C_{FG}$—C≡C—$C_{N^*\cap E}$, $N_{FG}$—CH$_2$—$C_{N^*\cap E}$.

The methods for connecting the function group to the N*∩E ligand and/or ligand L, either directly or via a bridge, are known to a person skilled in the art (Suzuki-, Still-, Heck-, Sonogashira-, Kumuda-, Ullmann-, Buchwald-Hartwig-coupling as well as their variants; (thio)etherification, esterification, nucleophilic and electrophilic substitutions at the spa-carbon atom or aromatic compounds, etc.). For example, the ligand (4,4'-bis(5-(hexylthio)-2,2'-bithiene-5'-yl)-2,2'-bipyridine) described in the literature illustrates the possibility of the connection of an electrophilic substituent to a bpy ligand via a Stille coupling (C.-Y. Chen, M. Wang, J.-Y. Li, N. Pootrakulchote, L. Alibabaei, C.-h. Ngoc-le, J.-D. Decoppet, J.-H. Tsai, C. Gratzel, C.-G. Wu, S. M. Zakeeruddin, M. Grätzel, ACS Nano 2009, 3, 3103).

In a particular embodiment, the group R can also be a substituent that conducts electrons, conducts holes or increases the solubility.

The invention also relates to a method for the production of a copper(I) complex according to the invention. This method according to the invention comprises the step of performing a chemical reaction of N*∩E and L with Cu(I)X, wherein X*=Cl, Br, I, CN, OCN, SCN, alkynyl and/or N$_3$ (independently from each other), N*∩E=a bidentate ligand with
  E=phosphanyl/arsanyl/antimonyl group of the form R$_2$E (with R=alkyl, aryl, heteroaryl, alkoxyl, phenoxyl, or amide);
  N*=imine function, which is part of an aromatic group, which is selected from pyridyl, pyridazinyl, pyrimidyl, pyrazinyl, triazinyl, tetrazinyl, oxazolyl, thiazolyl, imidazolyl, pyrazolyl, isoxazolyl, isothiazolyl, 1,2,3-triazolyl, 1,2,4-triazolyl, 1,2,4-oxadiazolyl, 1,2,4-thiadiazolyl, tetrazolyl, 1,2,3,4-oxatriazolyl, 1,2,3,4-thiatriazolyl, chinolyl, isochinolyl, chinoxalyl, chinazolyl, etc., which are optionally further substituted and/or annulated, "∩"=at least one carbon atom which is likewise part of the aromatic group, wherein the carbon atom is directly adjacent both to the imine nitrogen atom and to the phosphorus, arsenic or antimony atom, and L shaped:
either as two monodentate ligands $DR_3$ with
D=phosphanyl/arsanyl/antimonyl group of the form $R_3D$, wherein the three groups R are each independently from each other hydrogen, halogen or substituents, which are bound via oxygen (—OR), nitrogen (—$NR_2$) or silicon atoms (—$SiR_3$) as well as alkyl (also branched or cyclic), heteroalkyl, aryl, heteroaryl, alkenyl, alkynyl groups or substituted alkyl (also branched or cyclic), heteroalkyl, aryl, heteroaryl and alkenyl groups with substituents such as halogens or deuterium, alkyl groups (also branched or cyclic), heteroalkyl, aryl, heteroaryl and further donor and acceptor groups such as for example amines, carboxylates and their esters and $CF_3$ groups; the three individual groups R optionally lead to annulated ring systems;

or as bidentate ligand $R_2D$-B-$DR_2$ with
D=phosphanyl/arsanyl/antimonyl group of the form $R_2D$, that are bound to another group D via a bridge B, wherein the bridge B is a direct bond or a substituted or unsubstituted alkylene, alkenylene, alkynylene or arylene group or a combination of both, or —O—, —NR— or —$SiR_2$—, wherein the groups R are each independently from each other hydrogen, halogen or substituents, which are bound via oxygen (—OR), nitrogen (—$NR_2$) or silicon atoms (—$SiR_3$) as well as alkyl (also branched or cyclic), heteroalkyl, aryl, heteroaryl, alkenyl, alkynyl groups or substituted alkyl (also branched or cyclic), heteroalkyl, aryl, heteroaryl and alkenyl groups with substituents such as halogens or deuterium, alkyl groups (also branched or cyclic), heteroalkyl, aryl, heteroaryl and further donor and acceptor groups such as, for example, amines, carboxylates and their esters and $CF_3$ groups; the two individual groups R optionally lead to annulated ring systems;

or as two different monodentate ligands $DR_3$, wherein a ligand $DR_3$ can be identical or different to N*∩E with
D=phosphanyl/arsanyl/antimonyl group of the form $R_3D$ (with R=alkyl, aryl, heteroaryl, alkoxyl, phenoxyl, or amide), and N*∩E=a bidentate ligand with
E=phosphanyl/arsenyl/antimonyl group of the form $R_2E$ (with R=alkyl, aryl, heteroaryl, alkoxyl, phenoxyl, or amide);
N*=imine function which is part of an aromatic group which is selected from pyridyl, pyridazinyl, pyrimidyl, pyrazinyl, triazinyl, tetrazinyl, oxazolyl, thiazolyl, imidazolyl, pyrazolyl, isoxazolyl, isothiazolyl, 1,2,3-triazolyl, 1,2,4-triazolyl, 1,2,4-oxadiazolyl, 1,2,4-thiadiazolyl, tetrazolyl, 1,2,3,4-oxatriazolyl, 1,2,3,4-thiatriazolyl, chinolyl, isochinolyl, chinoxalyl, chinazolyl, etc., which are optionally further substituted and/or annulated,
"∩"=at least one carbon atom which is likewise part of the aromatic group, wherein the carbon atom is directly adjacent both to the imine nitrogen atom and to the phosphorus, arsenic or antimony atom.

The at least one substituent optionally present on the ligand N*∩E and/or L to increase the solubility of the complex in organic solvents and/or to improve the charge carrier transport is described further below.

The reaction is preferably performed in dichloromethane (DCM), but also other organic solvents such as acetonitrile or tetrahydrofuran or dimethyl sulfoxide or ethanol can be used. The addition of diethyl ether or hexane or methyl-tert-butyl ether or pentane or methanol or ethanol or water to the dissolved product allows for a solid to be obtained. This can be achieved by precipitation or inward diffusion or in an ultrasound bath.

Through the reaction of bidentate P∩N* ligands (P∩N*=phosphane ligand, for definition see below) and L with Cu(I)X (X=Cl, Br, I), preferably in dichloromethane (DCM), preferably at room temperature, the binuclear 2:3 complex $Cu_2X_2(E∩N^*)L_2$, in which the copper atoms are bridged by a phosphane ligand and the two halide anions (eq. 1), is surprisingly formed.

The structure of the formula A is related to known complexes of the $Cu_2X_2L_2L'$ or $Cu_2X_2L_4$ form. Unlike the case of $Cu_2X_2L_2L'$, the complex, however, is obtainable in only one step by the reaction of Cu(I)X with the bidentate P∩N* ligand and either two monodentate ligands $DR_3$ or one bidentate ligand $R_2D$-B-$DR_2$ or one monodentate ligand $DR_3$ and one monodentate ligand P∩N*, which can be identical of different to the bidentate ligand P∩N*. The complex can be isolated by precipitation with $Et_2O$ as a yellow or red microcrystalline powder. Single crystals can be obtained by slow diffusion of $Et_2O$ into the reaction solution. As soon as the complexes are present as powders or crystals, they are sparingly soluble to insoluble in common organic solvents. Especially at low solubilities, complexes were identified only by elemental and X-ray structural analyses.

eq. 1

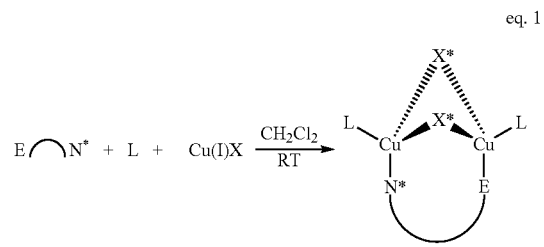

Above, the general formula A is shown. The bidentate ligands E∩N* and/or either the two monodentate ligands $DR_3$ or the bidentate ligand $R_2D$-B-$DR_2$ or the monodentate ligand $DR_3$ and the monodentate ligand P∩N*, which can be identical or different to the bidentate ligand P∩N*, can, independently from each other, comprise at least one substituent: The substituents can each independently from each other be hydrogen, halogen or substituents, which are bound via oxygen (—OR), nitrogen (—$NR_2$) or silicon atoms (—$SiR_3$) as well as alkyl (also branched or cyclic), heteroalkyl, aryl, heteroaryl, alkenyl, alkynyl groups or substituted alkyl (also branched or cyclic), heteroalkyl, aryl, heteroaryl and alkenyl groups with substituents such as halogens or deuterium, alkyl groups (also branched or cyclic), heteroalkyl, aryl, heteroaryl and further generally known donor and acceptor groups, such as, for example, amines, carboxylates and their esters and $CF_3$ groups. The substituents can also lead to annulated ring systems.

Substituents for Introducing Different Functionalities

The aforementioned substituents for introducing different functionalities via different ligands (for example, hole and/or electron conductors) for the warranty of a good charge carrier transport and a well-defined recombination directly on the copper complex, can be bound either singly or a number of times to the E∩N* and/or L ligand. Identical or different function groups can be used. The function groups can be present symmetrically or unsymmetrically.

Electron Conductors

Since the electron conductor materials are exclusively aromatic compounds, a substitution is possible using conventional coupling reactions. As coupling reactions, for example Suzuki-, Still-, Heck-, Sonogashira-, Kumuda-, Ullmann-, Buchwald-Hartwig-couplings as well as their variants can be used.

Thereby, a reaction is performed between an E∩N* ligand and/or L ligand substituted with a halide (Cl, Br, I), in particular Br, and a corresponding electron conducting material substituted with a suitable leaving group. Favorable is the performance of a Suzuki-coupling using the corresponding arylboronic acids and esters as well as a Buchwald-Hartwig-coupling for generating aryl-N-bonds. Depending on the function groups, further common linkage reactions can also be used, e.g. via a bridge between function group FG and E∩N* and/or L ligand. In the presence of —OH groups, esterification and etherification may be used, with —NH$_2$ groups imine and amide formation, with —COOH groups esterification. The substitution pattern of the E∩N* and/or L must be adapted accordingly. Methods for attaching the function groups FG are known to the person skilled in the art.

As an electron transport substituent, the following groups can for example be used (linkage takes place at the position marked with a #):

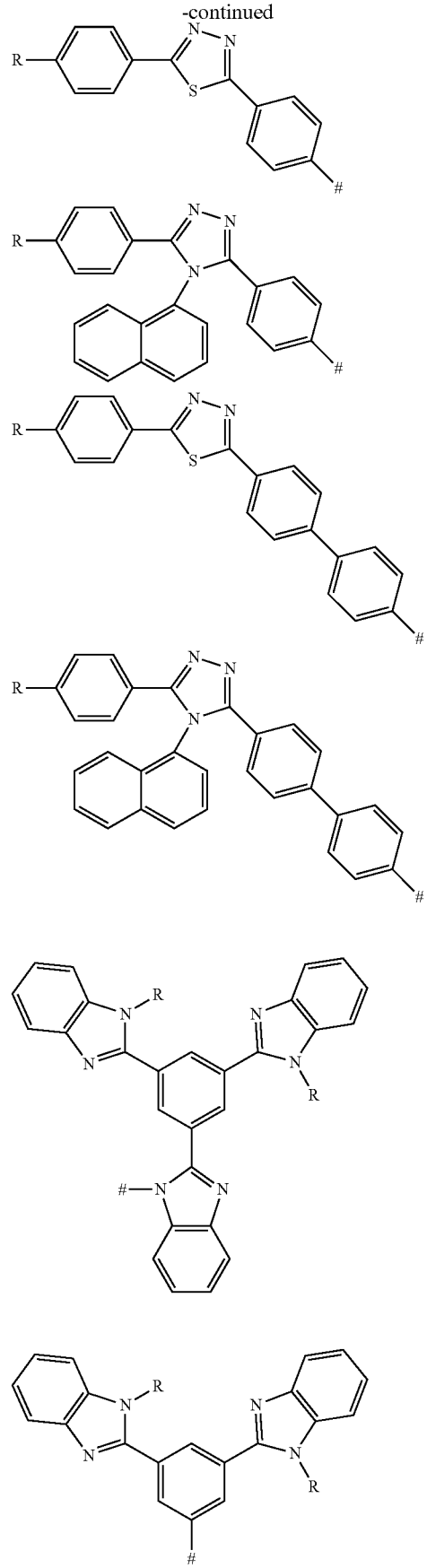

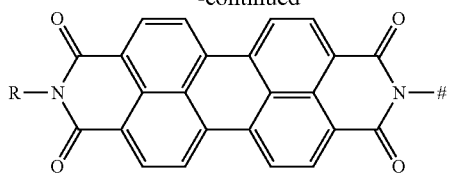

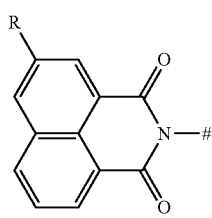

The substituents R and R' are alkyl groups [$CH_3$—($CH_2$)$_n$—] (n=0-20) that can also be branched or substituted with halogens (F, Cl, Br, I) or an aryl groups (in particular phenyl) that can be substituted with alkyl groups, halogens (F, Cl, Br, I), silane (—$SiR'''_3$) or ether groups —OR''' (R''' defined like R; the substituents used herein do not necessarily correspond to the substituents R, R', R'' of formula I or II). Likewise, R can be an unsaturated group, such as alkenyl and alkynyl groups, which again can be substituted with alkyl groups, halogens (F, Cl, Br, I), silane- (—$SiR''_3$) or ether groups —OR'' (R'' defined as R).

Hole Conductors

For the hole conductors, the analogous applies as for the electron conductors. The attachment of the hole conductor to the E∩N* and/or L ligand can also most conveniently be realized through palladium-catalyzed coupling reactions; further ways of attachments, also via a bridge, are possible.

As hole transport substituents, the following groups can, for example, be used (linkage take place at the position marked with a #):

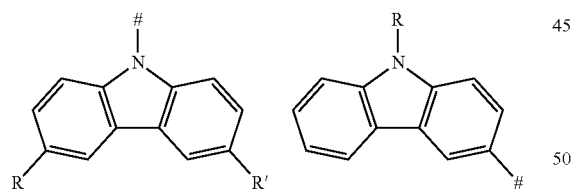

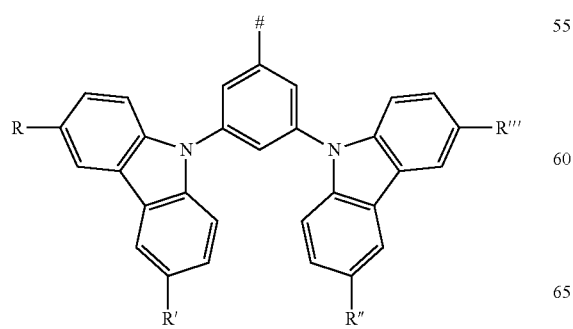

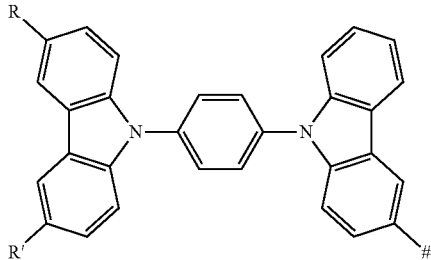

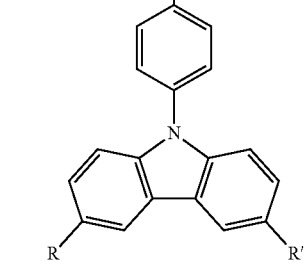

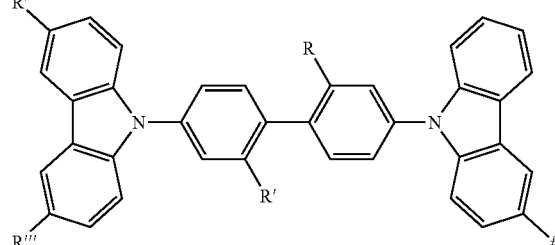

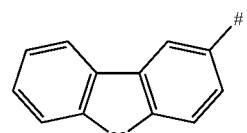

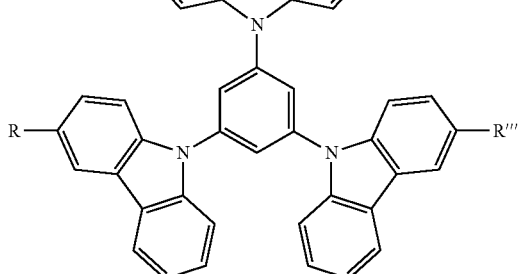

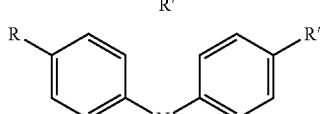

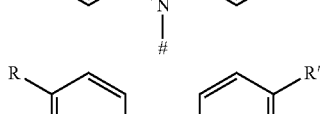

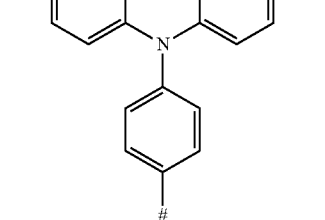

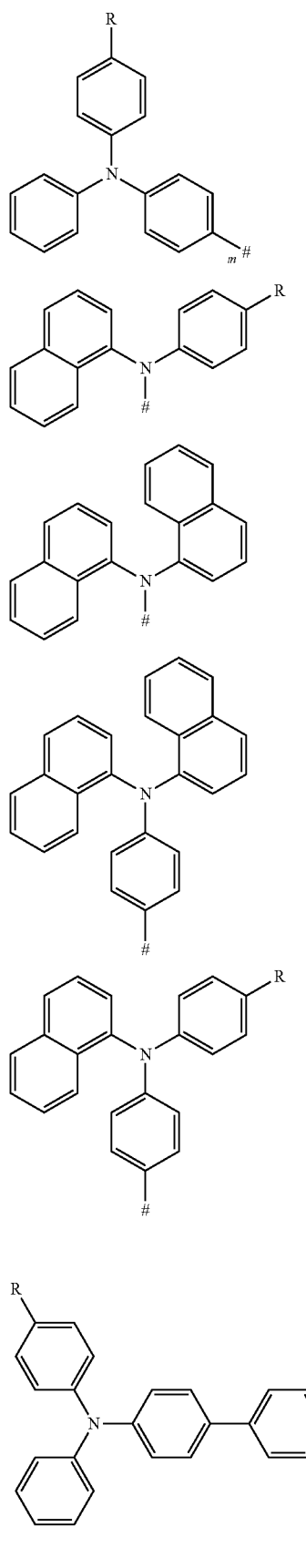
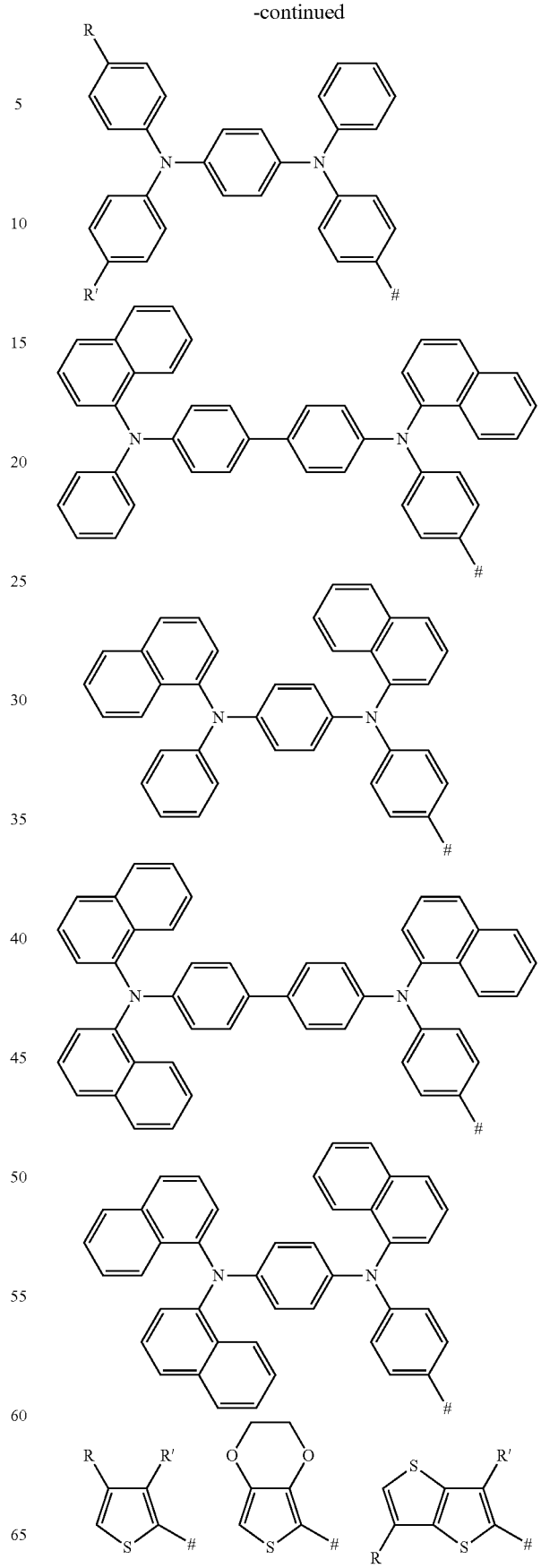

-continued

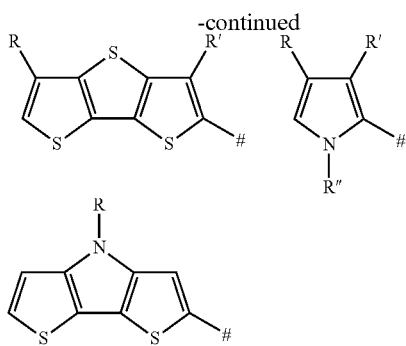

The substituent R, R″ and R‴ shown above is an alkyl group [$CH_3$—($CH_2$)$_n$—] (n=0-20) that can also be branched or substituted with halogens (F, Cl, Br, I), or an aryl group (in particular phenyl) that can be substituted with alkyl groups, halogens (F, Cl, Br, I), silane (—SiR‴″$_3$) or ether groups —OR‴″ (R‴″ defined like R; the substituents used above for the hole transport substituents do not necessarily correspond to the substituents R, R′, R″ of formula I or II). Likewise, R can be an unsaturated group such as alkenyl and alkynyl groups, which again can be substituted with alkyl groups, halogens (F, Cl, Br, I), silane- (—SiR″$_3$) or ether groups —OR″ (R″ defined as R).

For the use of the copper(I) complexes as self-catalyzing emitter materials for realizing a cross-linking with a second reactant, functionalities can be attached in the periphery of the E∩N* and/or L ligand that allow for a cross-linking with a corresponding complementary functional unit of the second reactant catalyzed by the copper(I) complex and thus make immobilization possible. In addition, such cross-linking provides for stabilization and fixation of the geometrical structure of the metal complexes, such that movement of the ligands and thus a change of structure of the excited molecules are inhibited and a decrease in efficiency due to radiationless relaxation pathways is effectively suppressed.

The copper catalyzed click reaction between a terminal or activated alkyne as first click group and an azide as a second click group is an example for a self-catalyzed cross-linking reaction. Since the metal complex emitter has to carry at least two alkyne units, at least two of the structures N*∩E and/or L are preferably substituted with at least one of the above-named functional groups each for the achievement of cross-linking, whereas the structure N*∩E and/or L not active in the cross-linking can optionally be substituted with another of the above-named functional groups for the increase of solubility of the complex in organic solvents and/or for improving the charge carrier transport.

Thus, different functionalities can be introduced via the periphery of the different ligands (for example, one hole and electron transport unit each for the achievement of an optimal charge carrier transport to and a well-defined recombination directly on the copper complex and/or a substituent for increasing the solubility of the complex in organic solvents and/or a functional group for achieving cross-linking), whereby a very flexible adjustment and modification of the metal(I) complexes is possible.

Solubility

When manufacturing optoelectronic devices using wet-chemical processes, it is advantageous to specifically regulate the solubility. Thereby, the complete or partial dissolution of a layer already deposited can be avoided. By introducing special substituents, the solubility characteristics can be strongly influenced. Thereby, it is possible to use orthogonal solvents that dissolve only the substance of the instant manufacturing step, but not the substances of the layer(s) below. For this purpose, the substituents $R^1$-$R^6$ can be chosen such that they allow tuning of the solubilities. The following possibilities for selecting corresponding substituents are given:

Solubility in Nonpolar Media

Nonpolar substituents $R^1$-$R^6$ increase the solubility in nonpolar solvents and decrease the solubility in polar solvents. Nonpolar groups are, e.g. alkyl groups [$CH_3$—($CH_2$)$_n$—] (n=1-30), also branched or cyclic, substituted alkyl groups, e.g. with halogens. Particular notice deserve: partially or perfluorinated alkyl groups as well as perfluorinated oligo- and polyethers, e.g. [—($CF_2$)$_2$—O]$_n$— and (—$CF_2$—O)$_n$— (n=2-500). Further nonpolar groups are: ether —OR*, thioether —SR*, differently substituted silanes R*$_3$Si— (R*=alkyl or aryl), siloxanes R*$_3$Si—O—, oligosiloxanes R(—R$_2$Si—O)$_n$— (R=R*, n=2-20), polysiloxanes R**(—R*$_2$Si—O)$_n$— (n>20); oligo/polyphosphazenes R**(—R*$_2$P=N—)$_n$— (n=1-200).

Solubility in Polar Media

Polar substituents $R^1$-$R^6$ increase the solubility in polar media. These can be:

Alcohol groups: —OH

Carboxylic acid, phosphonic acid, sulfonic acid groups as well as their salts and esters (R*=H, alkyl, aryl, halogen; cations: alkali metals, ammonium salts): —COOH, —P(O)(OH)$_2$, —P(S)(OH)$_2$, —S(O)(OH)$_2$, —COOR*, —P(O)(OR*)$_2$, —P(S)(OR*)$_2$, —S(O)(OR*)$_2$, —CONHR*, —P(O)(NR*$_2$)$_2$, —P(S)(NR*$_2$)$_2$, —S(O)(NR*$_2$)$_2$ Sulfoxides: —S(O)R*, —S(O)$_2$R*

Carbonyl groups: —C(O)R*

Amines: —NH$_2$, —NR*$_2$, —N($CH_2CH_2$OH)$_2$,

Hydroxylamines =NOR*

Oligoesters, —O($CH_2$O—)$_n$, —O($CH_2CH_2$O—)$_n$ (n=2-200)

Positively charged substituents: e.g. ammonium salts —N$^+$R*$_3$X$^-$, phosphonium salts —P$^+$R*3X$^-$ Negatively charged substituents: e.g. borate —(BR*$_3$)$^-$, aluminate —(AlR*$_3$)$^-$ (the anion can be an alkali metal or ammonium ion).

The preparation method can optionally comprise the step that at least one ligand N*∩E and/or L is substituted with at least one of the above named substituents for increasing the solubility in an organic solvent, wherein in one embodiment of the invention the substituent can be selected from the group consisting of:

long-chain, branched or unbranched or cyclic alkyl chains with a length of C1 to C30, long-chain, branched or unbranched or cyclic alkoxy chains with a length of C1 to C30, branched or unbranched or cyclic perfluoroalkyl chains with a length of C1 to C30, and short-chain polyethers.

The preparation method can optionally comprise the step that at least one ligand N*∩E and/or L is substituted with at least one of the above-named functional groups for improving charge carrier transport and for increasing the recombination probability of the charge carrier directly on the copper(I) complexes according to the invention, wherein the functional group at the ligand N*∩E can be identical or different to the functional group at the ligand L, preferably different, wherein the substituent can be selected in one embodiment of the invention from the group consisting of electron conductors and hole conductors.

The invention also includes copper(I) complexes producible by such a synthesis process.

According to the invention, the copper(I) complexes of the formula A can be used as an emitter material in an emitter layer of a light emitting optoelectronic component.

According to the invention, the copper(I) complexes of the formula A can also be used as an absorber material in an absorber layer of an optoelectronic component.

The expression "optoelectronic components" is understood to mean especially:

organic light emitting components (organic light emitting diodes, OLEDs),
light emitting electrochemical cells (LECs, LEECs),
OLED sensors, especially in gas and vapor sensors that are not hermetically sealed from the outside,
organic solar cells (OSCs, organic photovoltaics, OPVs),
organic field-effect transistors and
organic lasers.

The proportion of the copper(I) complex in the emitter or absorber layer in such an optoelectronic component is, in one embodiment of the invention, 100%. In an alternative embodiment, the proportion of the copper(I) complex in the emitter or absorber layer is 1% to 99%.

Advantageously, the concentration of the copper(I) complex as an emitter in optical light-emitting components, especially in OLEDs, is between 5% and 80%.

The present invention also provides for optoelectronic components which comprise a copper(I) complex as described herein. The optoelectronic component can be in the form of an organic light-emitting component, an organic diode, an organic solar cell, an organic transistor, an organic light-emitting diode, a light-emitting electrochemical cell, an organic field-effect transistor and an organic laser.

Furthermore, the present invention relates to a method for the production of an optoelectronic device, wherein a copper (I) complex according to the invention of the type described herein is used. In this method, in particular a copper(I) complex according to the invention is applied onto a support. This application can be conducted wet-chemically, by means of colloidal suspension or by means of sublimation, in particular wet-chemically. The method can comprise the following steps: Application of a first emitter complex dissolved in a first solvent onto a carrier, and depositing a second emitter complex dissolved in a second solvent onto the carrier; wherein the first emitter complex is not soluble in the second solvent, and the second emitter complex is not soluble in the first solvent; and wherein the first emitter complex and/or the second emitter complex is a copper(I) complex according to the invention. The method can further comprise the following step: Application of a third emitter complex dissolved in a first solvent or in a third solvent onto the carrier, wherein the third copper(I) complex is a copper (I) complex according to the invention. First and second solvent are not identical.

The present invention also relates to a process for altering the emission and/or absorption properties of an electronic component. This involves introducing a copper(I) complex according to the invention into a matrix material for conduction of electrons or holes into an optoelectronic component.

The present invention also relates to the use of a copper(I) complex according to the invention, especially in an optoelectronic component, for conversion of UV radiation or of blue light to visible light, especially to green (490-575 nm), yellow (575-585 nm), orange (585-650 nm) or red light (650-750 nm) (down-conversion).

In a preferred embodiment, the optoelectronic device is a white-light OLED, wherein the first emitter complex is a red-light emitter, the second emitter complex is a green-light emitter and the third emitter complex is a blue-light emitter. The first, second and/or third emitter complex is preferably a copper(I) complex according to the invention.

Since the copper(I) complexes according to the invention with unsubstituted N*∩E ligands are in part sparingly soluble in some organic solvents, they may not be processable directly from solution. In the case of solvents that are themselves good ligands (acetonitrile, pyridine), a certain solubility exists, but a change in the structure of the complexes or displacement of the phosphane or arsane or antimony ligands under these conditions cannot be ruled out. It is therefore unclear whether the substances, in the event of deposition on the substrate, will crystallize as $Cu_2X_2$(E∩N*)(L)$_2$, or will be present molecularly in this form in the matrix. For this reason, the substances should be produced in a size suitable for use in optoelectronic components or be reduced thereto (<20 nm to 30 nm, nanoparticles), or be rendered soluble by means of suitable substituents.

The copper(I) complexes according to the invention are preferably processed from solution, since the high molecular weight complicates deposition from vacuum by sublimation. Therefore, the photoactive layers are preferably produced from solution by spin-coating or slot-casting processes, or by any printing process such as screenprinting, flexographic printing, offset printing or inkjet printing.

The unsubstituted copper(I) complexes described here (definition further below, see Examples) are, however, sparingly soluble in the standard organic solvents, except for dichloromethane, which should not be used for OLED component production in a glovebox. Application as a colloidal suspension is possible in many cases (see further below), but industrial processing of the emitter materials in dissolved form is usually simpler in technical terms. It is therefore a further aim of this invention to chemically alter the emitters such that they are soluble. Suitable solvents for the OLED component production are, as well as alcohols, ethers, alkanes and halogenated aromatic and aliphatic hydrocarbons and alkylated aromatic hydrocarbons, especially toluene, chlorobenzene, dichlorobenzene, mesitylene, xylene, tetrahydrofuran, phenetole, and propiophenone.

In order to improve the solubility of the copper(I) complexes according to the invention in organic solvents, at least one of the structures N*∩E and/or L is preferably substituted with at least one of the above named substituents. The substituent can be selected from the group consisting of:

long-chain, branched or unbranched or cyclic alkyl chains with a length of C1 to C30, preferably with a length of C3 to C20, particularly preferably with a length of C5 to C15, long-chain, branched or unbranched or cyclic alkoxy chains with a length of C1 to C30, preferably with a length of C3 to C20, particularly preferably with a length of C5 to C15, branched or unbranched or cyclic perfluoroalkyl chains with a length of C1 to C30, preferably with a length of C3 to C20, particularly preferably with a length of C5 to C15, and short-chain polyethers, for example polymers of the (—OCH$_2$CH$_2$O—)$_n$ form where n<500.

Examples thereof are polyethylene glycols (PEGs), which can be used as chemically inert, water-soluble and nontoxic polymers with a chain length of 3 to 50 repeat units.

In a preferred embodiment of the invention, the alkyl chains or alkoxy chains or perfluoroalkyl chains are modified with polar groups, for example with alcohols, aldehydes, acetals, amines, amidines, carboxylic acids, carboxylic esters, carboxamides, imides, carbonyl halides, carboxylic anhydrides, ethers, halogens, hydroxamic acids, hydrazines, hydrazones, hydroxylamines, lactones, lactams, nitriles, isocyanides, isocyanates, isothiocyanates, oximes, nitrosoaryls, nitroalkyls, nitroaryls, phenols, phosphoric esters and/or phosphonic acids, thiols, thioethers, thioaldehydes, thioketones, thioacetals, thiocarboxylic acids, thioesters, dithio acids, dithio esters, sulfoxides, sulfones, sulfonic acids, sulfonic esters, sulfinic acids, sulfinic esters, sulfenic acids, sulfenic esters, thiosulfinic acids, thiosulfinic esters, thiosulfonic acids, thiosulfonic esters, sulfonamides, thiosulfonamides, sulfinamides, sulfenamides, sulfates, thiosulfates, sultones, sultams, trialkylsilyl and triarylsilyl groups, and also trialkoxysilyl groups which result in a further increase in solubility.

A very marked increase in solubility is achieved from at least one C6 unit, branched or unbranched or cyclic.

In order to improve the charge carrier transport and the recombination probability of the charge carrier directly on the copper(I) complexes according to the invention, at least one of the structures N*∩E and/or L is preferably substituted with at least one of the above-listed functional groups for the improvement of the charge carrier transport, wherein the functional group at the ligand N*∩E can be identical or different to the functional group at the ligand L, preferably different. The substituent can be selected from the group consisting of electron conductor and hole conductor.

The substituents of the structures N*∩E and/or L of the copper(I) complexes can be arranged anywhere in the structure. In particular, a position of the substituent in the ortho, meta and/or para position to the heteroatom which forms the coordination to the Cu ion is possible. Preference is given to substitution in the meta and/or para position.

A further aspect of the invention relates to the alteration of the emission colors of the copper(I) complexes by means of electron-donating or -withdrawing substituents, or by means of fused N-heteroaromatics. The terms electron-donating and electron-withdrawing are known to a person skilled in the art.

Examples of electron-donating substituents are especially:
-alkyl, -phenyl, —CO$_2$(-), —O(-), —NH-alkyl group, —N-(alkyl group)$_2$, —NH$_2$, —OH, —O-alkyl group, —NH(CO)-alkyl group, —O(CO)-alkyl group, —O(CO)-aryl group, —O(CO)-phenyl group, —(CH)=C-(alkyl group)$_2$, —S-alkyl group.

Examples of electron-withdrawing substituents are especially:
-halogen, —(CO)H, —(CO)-alkyl group, —(CO)O-alkyl group, —(CO)OH, —(CO)halide, —CF$_3$, —CN, —SO$_3$H, —NH$_3$(+), —N(alkyl group)$_3$(+), —NO$_2$.

Advantageously, the electron-donating and -withdrawing substituents are removed from the coordination site of the ligand as far as possible, and are especially in the meta or para position.

It is thus possible, through suitable selection of substitution within the base structure of a pyridine ligand, to establish a very broad emission color range.

The change in the emission colors of the copper(I) complexes described here can also be effected by further heteroatoms, such as N, O, S, and by means of fused N, O and S heteroaromatics.

The use of fused N-heteroaromatics such as, for example, isoquinoline, benzothiazole, quinoxaline enables color shifts, for example into the yellow to deep-red spectral range. The solubility of copper(I) complexes with fused N-heteroaromatics can likewise be increased by substitution(s) with the above-described substituents, long-chain (branched or unbranched or cyclic) alkyl chains of length C1 to C30, preferably with a length of C3 to C20, particularly preferably with a length of C5 to C15, long-chain (branched or unbranched or cyclic) alkoxy chains of length C1 to C30, preferably with a length of C3 to C20, particularly preferably with a length of C5 to C15, long-chain (branched or unbranched or cyclic) perfluoroalkyl chains of length C1 to C30, preferably with a length of C3 to C20, particularly preferably with a length of C5 to C15, and short-chain polyethers (chain length: 3 to 50 repeat units).

In a preferred embodiment, the copper(I) complex according to the invention comprises at least one substituent to increase solubility in an organic solvent and/or at least one electron-donating and/or at least one electron-withdrawing substituent. It is also possible that a substituent that improves solubility is simultaneously either an electron-donating or -withdrawing substituent. One example of such a substituent is a dialkylated amine with an electron-donating effect via the nitrogen atom and a solubility-increasing effect through the long-chain alkyl groups.

By means of a modular synthesis strategy in which the individual units for preparation of these ligands are combined with one another in a matrix, the introduction of linear and branched and cyclic alkyl chains, alkoxy chains or perfluoroalkyl chains of different lengths at different positions in the molecules is possible. Preference is given to substitutions which are far removed from the coordination site of the ligand or the ligands N*∩E and/or L.

Proceeding from a suitable synthesis unit A, in analogous reactions, different reactants B, C and D are linked under analogous reaction conditions to give chemically diverse target molecules AB, AC and AD. It is thus possible, for example, to attach alkyl chains of different lengths to a suitable pyridine ligand in a modular manner by use of nucleophilic substitution reactions.

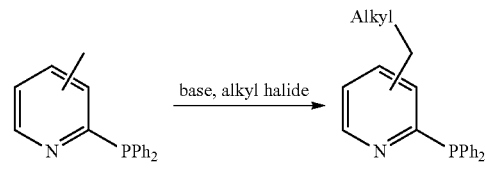

For the production of the abovementioned nanoparticles smaller than 30 nm, it is possible to employ several techniques:[xxii]

Bottom-up processes for synthesis of nanoparticles:

Rapid injection of the reaction solution into a large excess of a suitable precipitant (e.g. pentane, diethyl ether).[xxiii]

Fine atomization of the reaction solution in a vacuum chamber, possibly at elevated temperature (spray drying). This vaporizes the solvent, leaving the complex in finely distributed form.

In a freeze-drying process, the droplets of the reaction solution are dispersed in a coolant (e.g. liquid nitrogen), which freezes the material. Subsequently, it is dried in the solid state.

Co-deposition of the complexes and of the matrix material on the substrate directly from the reaction solution.

Synthesis in an ultrasound bath.

Top-down processes for comminution of the substances:
Comminution by means of high-energy ball mills.[xxiv]
Comminution by means of high-intensity ultrasound.

Isolation of particles with the desired size can be achieved by filtration with suitable filters or by centrifugation.

In order to achieve homogeneous distribution of the nanoparticles in the matrix (for example of the matrix material used in the emitter layer), a suspension is prepared in a solvent in which the matrix material dissolves. The customary processes (for example, spin-coating, inkjet printing, etc.) can be used to apply the matrix material and the nanoparticles to a substrate with this suspension. In order to avoid aggregation of the nanoparticles, stabilization of the particles by means of surface-active substances may be necessary under some circumstances. However, these should be selected such that the complexes are not dissolved. Homogeneous distribution can also be achieved by the abovementioned co-deposition of the complexes together with the matrix material directly from the reaction solution.

Since the substances described possess a high emission quantum yield even as solids, they can also be deposited directly on the substrate as a thin layer (100% emitter layer) proceeding from the reaction solution.

EXAMPLES

In the examples shown here, the ligand E∩N* of the general formula A is a ligand P∩N* (with E=Ph$_2$P). The identities and structures of the complexes 1 to 51 were clearly proven by NMR spectroscopy, mass spectroscopy, elemental analyses and/or crystal structure analyses (see FIG. 1A).

Examples of Complexes of the Form Cu$_2$X$_2$(P∩N*)L$_2$

I. P∩N*=Ph$_2$Ppic, L=PPh$_3$: Cu$_2$I$_2$(Ph$_2$Ppic)(PPh$_3$)$_2$ (1)

The compound 1 is a yellow, fine-crystalline solid.

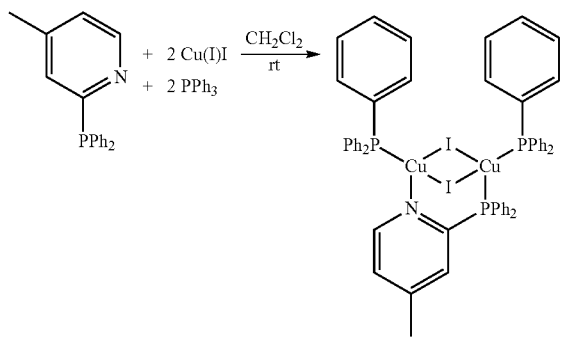

Eq. 3

Figure 1B:
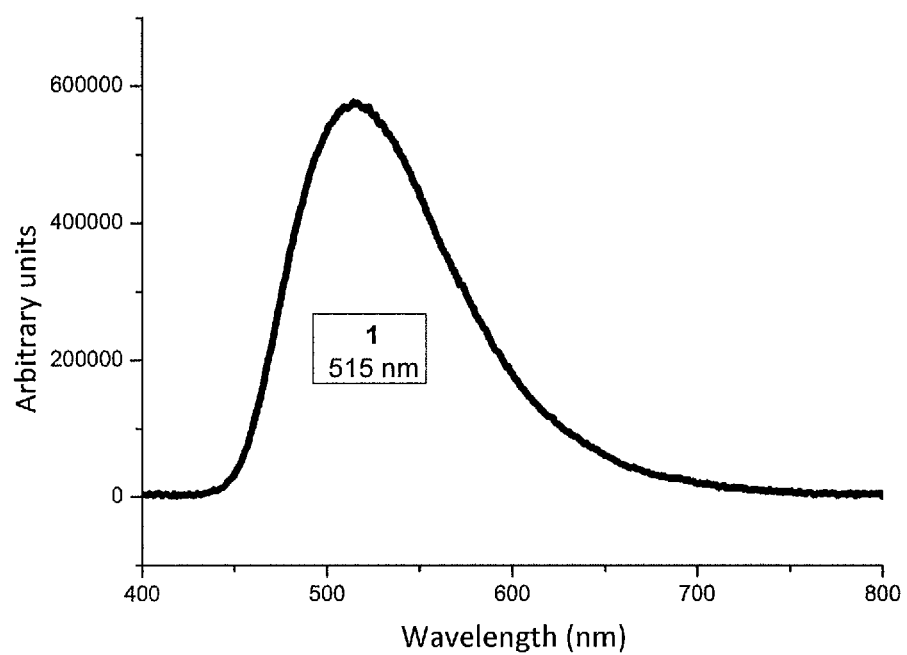
FIG. 1B shows a graphical overview of the emission spectrum of compound 1 in accordance with an embodiment of the present invention.

Characterization:
Elemental Analysis:
found: C 54.45; H 4.04; N 0.79
calc.: C 54.84; H 3.92; N 1.18
The crystal structure is shown in FIG. 1A.
The emission spectrum is shown in FIG. 1B.

II. P∩N*=Ph$_2$Ppic, L=P(p-Tol)$_3$: Cu$_2$I$_2$(Ph$_2$Ppic)(P(p-Tol)$_3$)$_2$ (2)

2 is a yellow, fine-crystalline solid.

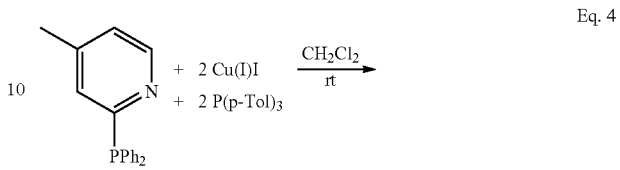

Eq. 4

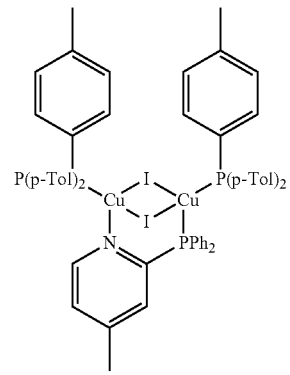

Figure 2:
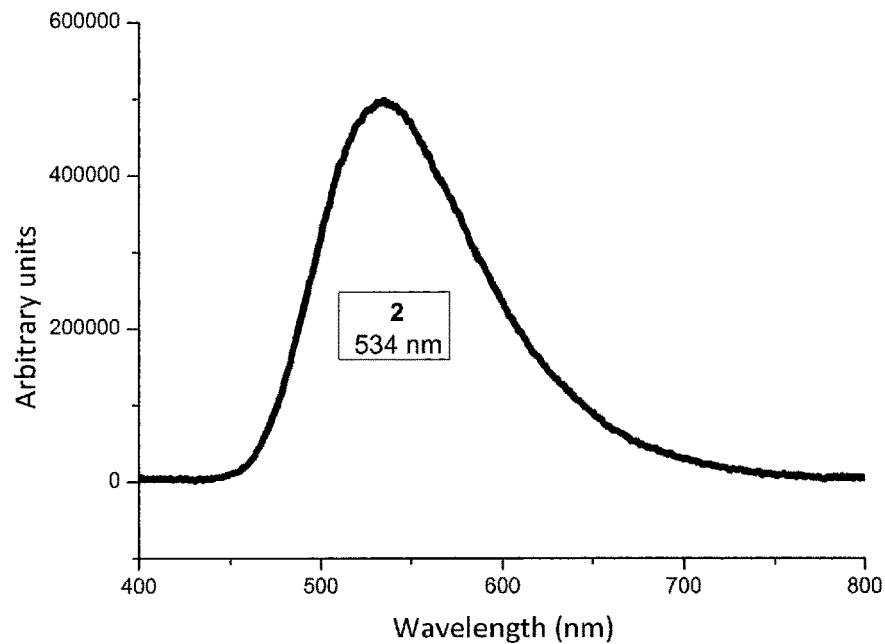
FIG. 2 shows a graphical overview of the emission spectrum of compound 2 in accordance with an embodiment of the present invention.

Characterization:
Elemental Analysis:
found: C 53.88; H 4.44; N 0.86
calc.: C 54.20; H 4.47; N 1.04
The emission spectrum is shown in FIG. 2

III. P∩N*=Ph$_2$Pic, L=EtPPh$_2$: Cu$_2$I$_2$(Ph$_2$Pic)(EtPPh$_2$)$_2$ (3)

The compound 3 is a yellow, fine-crystalline solid.

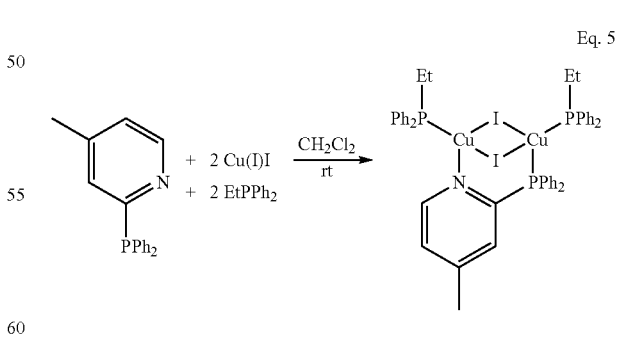

Eq. 5

Figure 3:
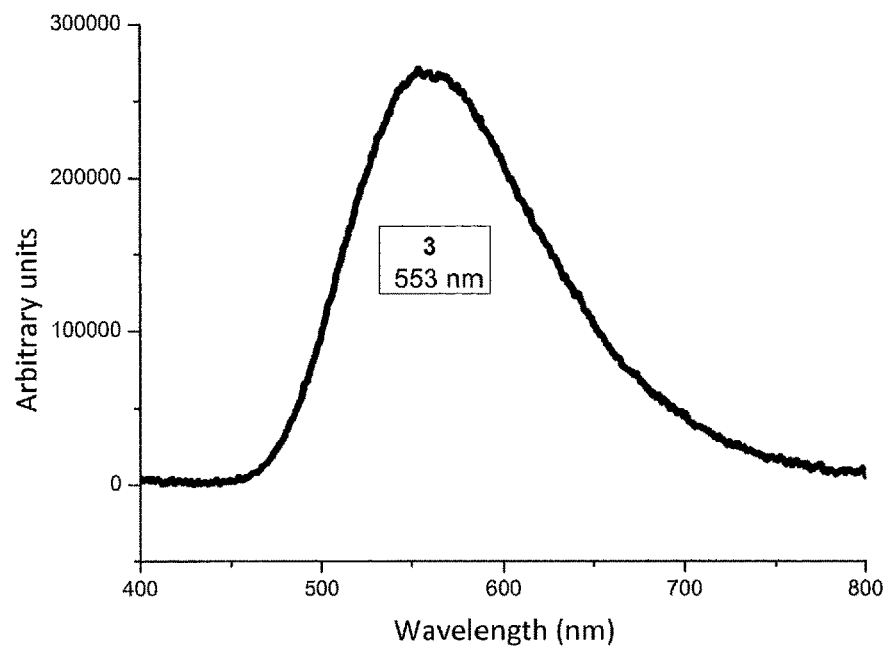
FIG. 3 shows a graphical overview of the emission spectrum of compound 3 in accordance with an embodiment of the present invention.

Characterization:
Elemental Analysis:
found: C 50.70; H 4.28; N 1.20
calc.: C 50.84; H 4.27; N 1.29
The emission spectrum is shown in FIG. 3

IV. P∩N*=Ph₂P(2-Mepy), L=PPh₃: Cu₂I₂(Ph₂P(2-Mepy))(PPh₃)₂ (4)

The compound 4 is a yellow, fine-crystalline solid.

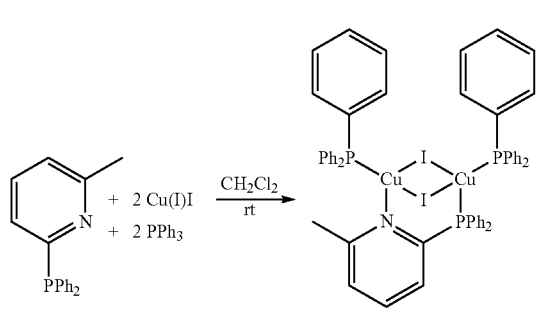

Figure 4:
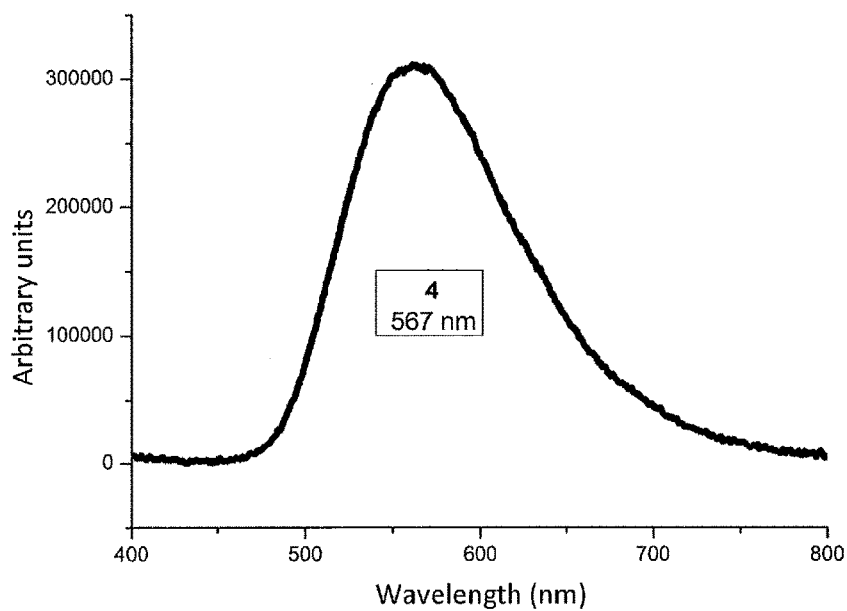
FIG. 4 shows a graphical overview of the emission spectrum of compound 4 in accordance with an embodiment of the present invention.

Characterization:
Elemental Analysis:
found: C 48.06; H 3.68; N 0.91
calc.: C 47.62; H 3.65; N 0.97
The emission spectrum is shown in FIG. 4.

V. P∩N*=Ph₂P(iBupy), L=PPh₃: Cu₂I₂(Ph₂P(iBupy))(PPh₃)₂ (5)

The compound 5 is a yellow, fine-crystalline solid.

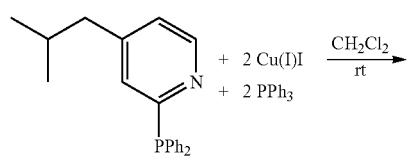

Figure 5:
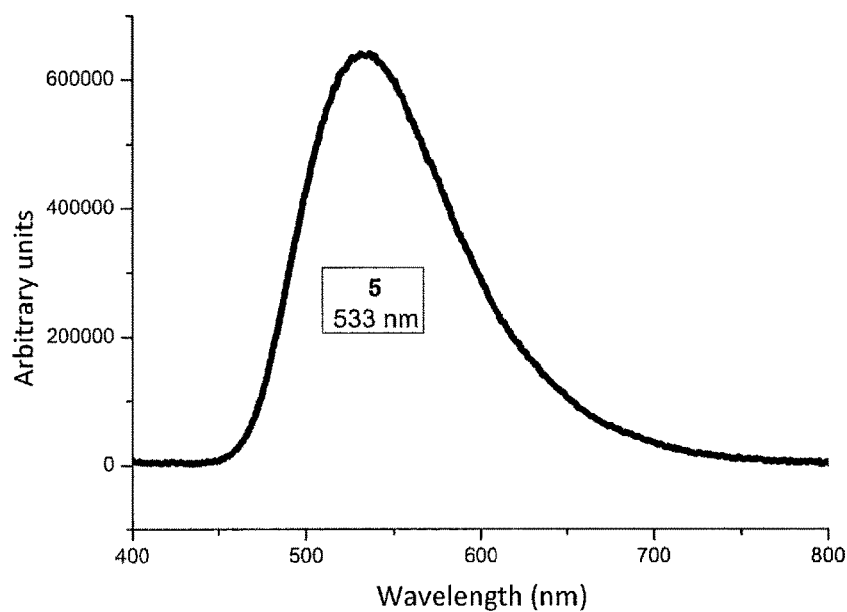
FIG. 5 shows a graphical overview of the emission spectrum of compound 5 in accordance with an embodiment of the present invention.

Characterization:
Elemental Analysis:
found: C 56.55; H 4.80; N 0.75
(with ½ molecule n-hexane)
calc.: C 56.84; H 4.69; N 1.10
The emission spectrum is shown in FIG. 5.

VI. P∩N*=Ph₂P(cyPentpy), L=PPh₃: Cu₂I₂(Ph₂P(cyPentpy))(PPh₃)₂ (6)

The compound 6 is a yellow, fine-crystalline solid.

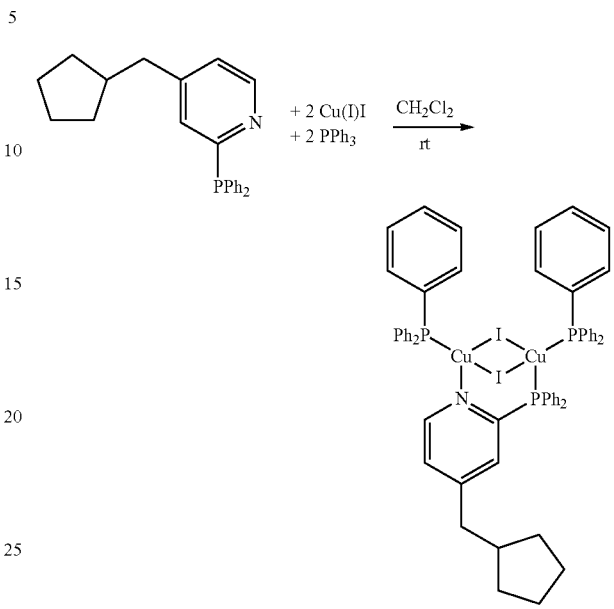

Figure 6:
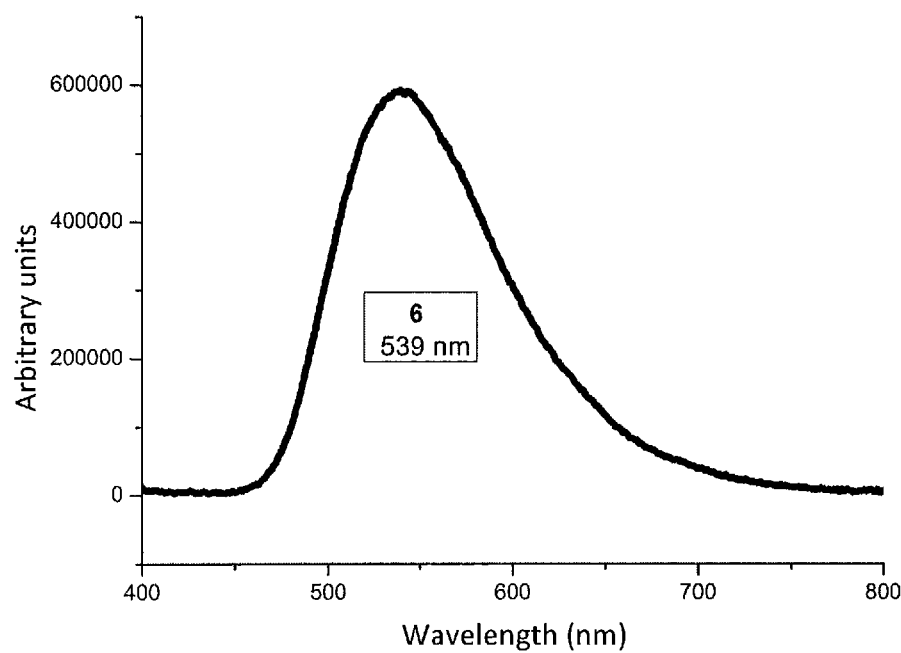
FIG. 6 shows a graphical overview of the emission spectrum of compound 6 in accordance with an embodiment of the present invention.

Characterization:
Elemental Analysis:
found: C 57.19; H 5.08; N 0.69
(with ¼ molecule n-hexane)
calc.: C 57.11; H 4.55; N 1.10
The emission spectrum is shown in FIG. 6.

VII. P∩N*=Ph₂Piqn, L=PPh₃: Cu₂I₂(Ph₂Piqn)(PPh₃)₂ (7)

The compound 7 is an orange-colored, crystalline solid.

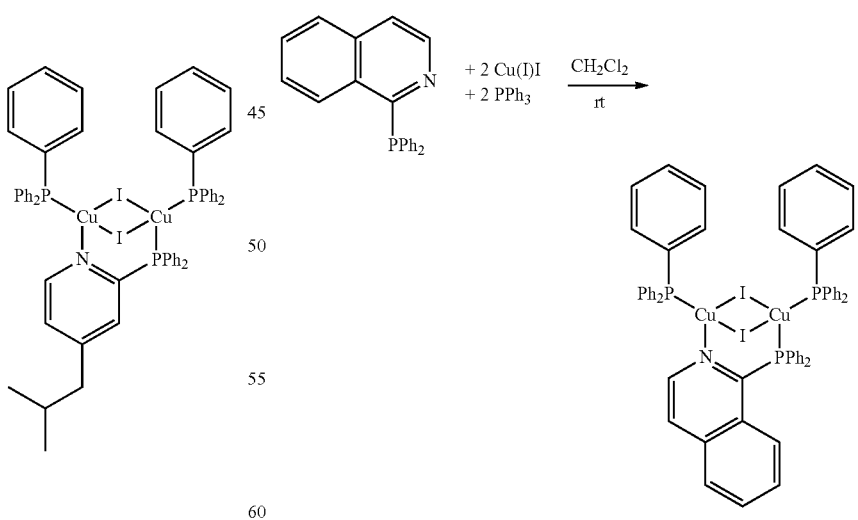

Figure 7:
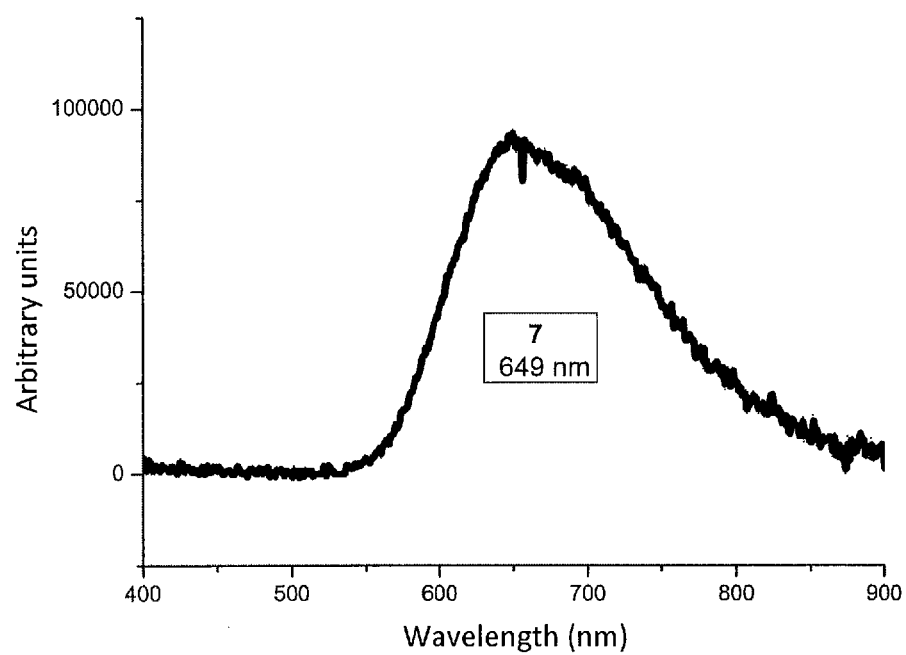
FIG. 7 shows a graphical overview of the emission spectrum of compound 7 in accordance with an embodiment of the present invention.

Characterization:
Elemental Analysis:
found: C 57.15; H 3.92; N 1.29
(with ½ molecule n-hexane)
calc.: C 57.11; H 4.23; N 1.11
The emission spectrum is shown in FIG. 7.

VIII. P∩N*=Ph$_2$P(Oxadiazole), L=PPh$_3$: Cu$_2$I$_2$(Ph$_2$P(Oxadiazole))(PPh$_3$)$_2$ (8)

The compound 8 is a yellow, fine-crystalline solid.

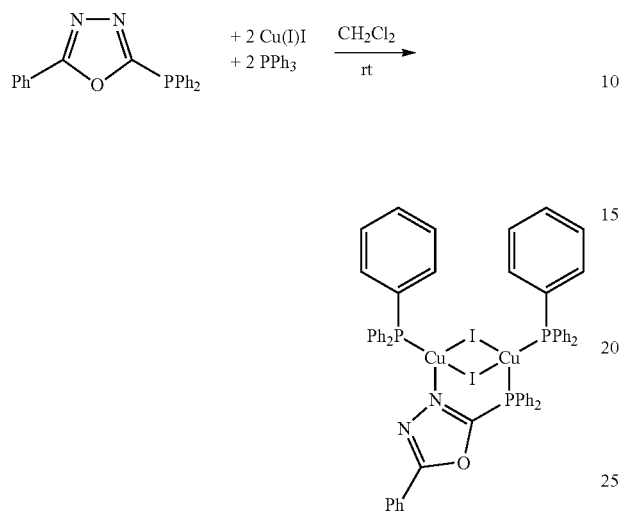

Figure 8:
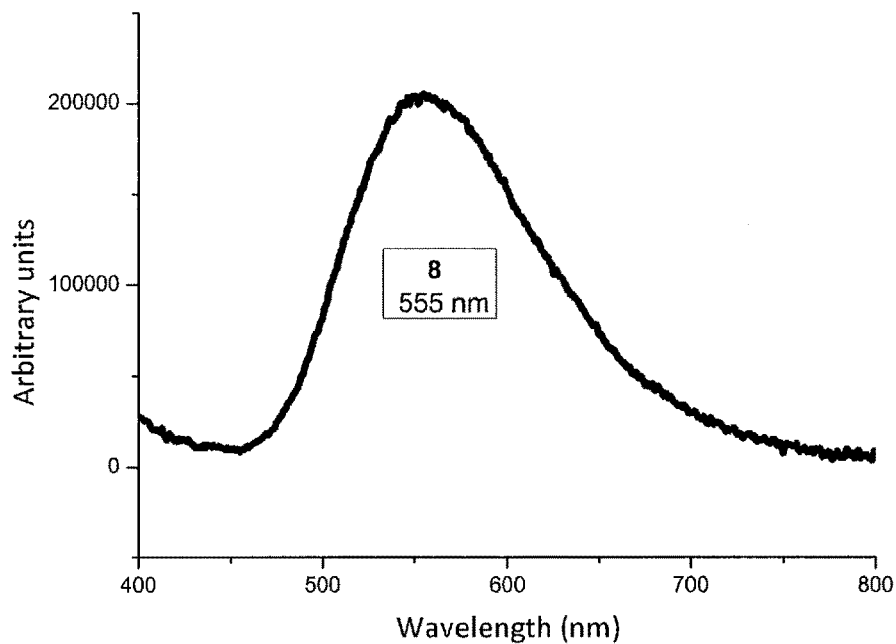
FIG. 8 shows a graphical overview of the emission spectrum of compound 8 in accordance with an embodiment of the present invention.

Characterization:
Elemental Analysis:
found: C 54.45; H 4.07; N 1.97
calc.: C 54.43; H 3.67; N 2.27
The emission spectrum is shown in FIG. 8.

IX. P∩N*=Ph$_2$P(Oxadiazole), L=P(p-Tol)$_3$: Cu$_2$I$_2$(Ph$_2$P(Oxadiazole))(P(p-Tol)$_3$)$_2$ (9)

The compound 9 is a yellow, fine-crystalline solid.

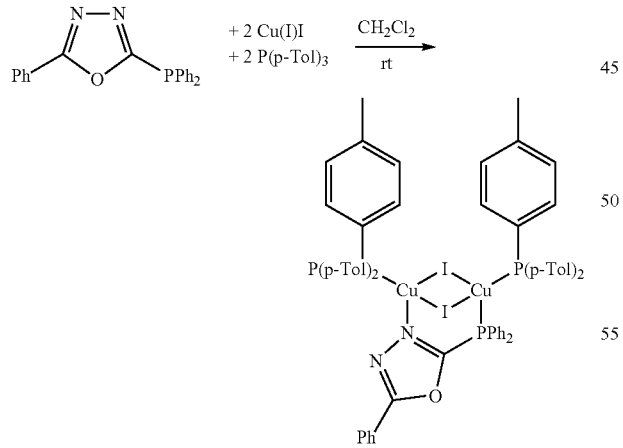

Figure 9:
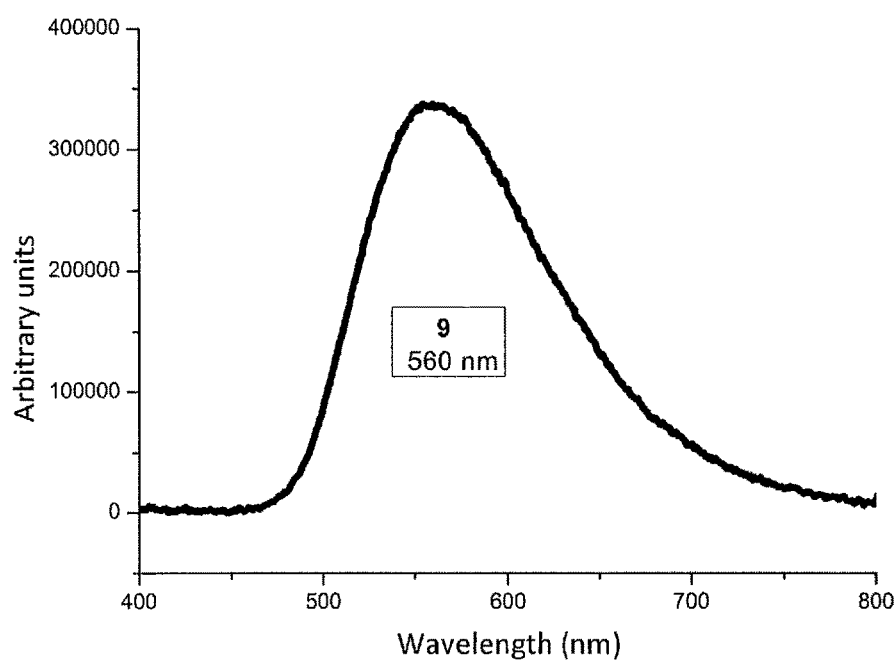
FIG. 9 shows a graphical overview of the emission spectrum of compound 9 in accordance with an embodiment of the present invention.

Characterization:
Elemental Analysis:
found: C 55.80; H 4.16; N 2.54
calc.: C 56.42; H 4.35; N 2.12
The emission spectrum is shown in FIG. 9.

X. P∩N*=Ph$_2$P(Oxadiazole), L=EtPPh$_2$: Cu$_2$I$_2$(Ph$_2$P(Oxadiazole))(EtPPh$_2$)$_2$ (10)

The compound 10 is a yellow, fine-crystalline solid.

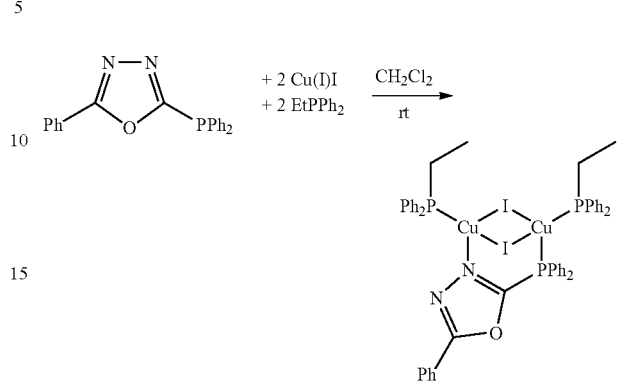

Figure 10:
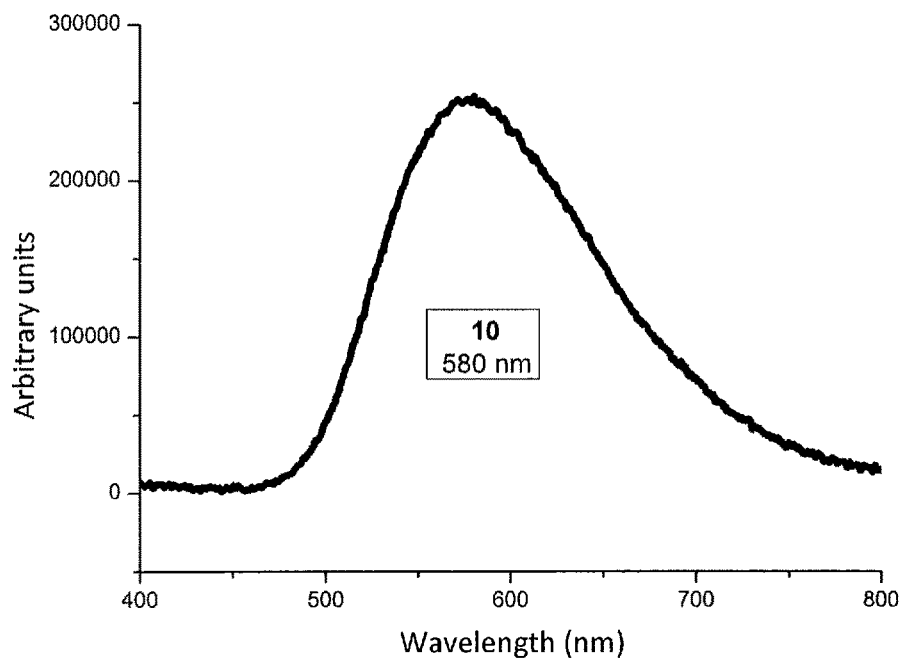
FIG. 10 shows a graphical overview of the emission spectrum of compound 10 in accordance with an embodiment of the present invention.

Characterization:
Elemental Analysis:
found: C 50.05; H 3.83; N 2.70
calc.: C 49.92; H 3.95; N 2.41
The emission spectrum is shown in FIG. 10.

XI. P∩N*=Ph$_2$P(Oxadiazole), L=MePPh$_2$: Cu$_2$I$_2$(Ph$_2$P(Oxadiazole))(MePPh$_2$)$_2$ (11)

The compound 11 is a yellow, fine-crystalline solid.

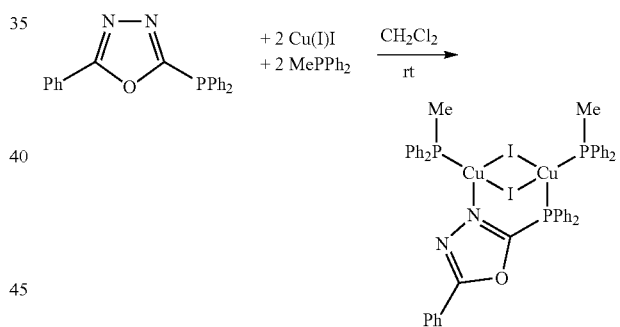

Figure 11:
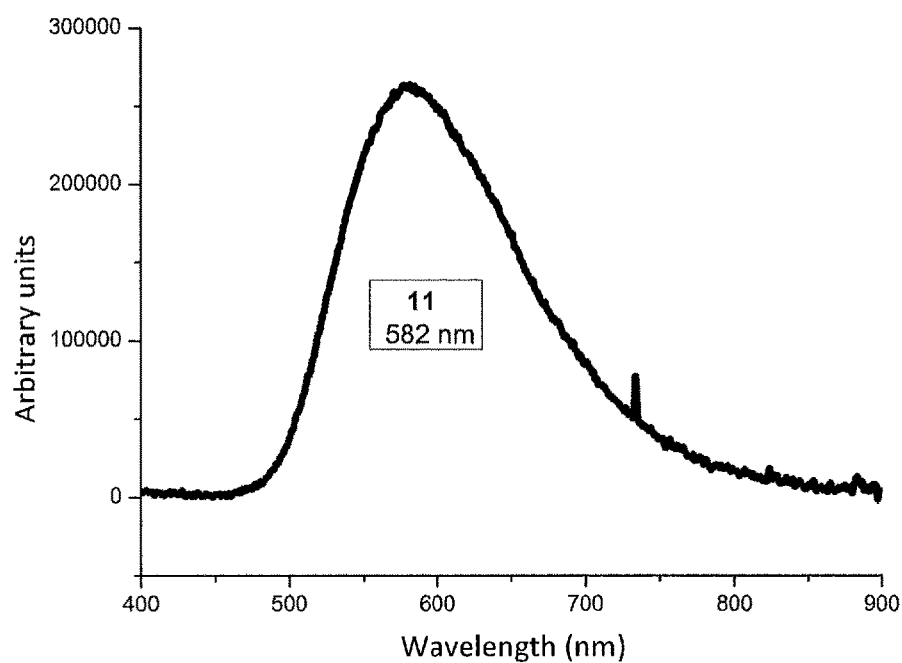
FIG. 11 shows a graphical overview of the emission spectrum of compound 11 in accordance with an embodiment of the present invention.

Characterization:
Elemental Analysis:
found: C 50.18; H 3.98; N 2.25
calc.: C 49.70; H 3.72; N 2.52
The emission spectrum is shown in FIG. 11.

XII. P∩N*=Ph$_2$P(Oxadiazole), L=PhP(CH$_2$CH$_2$PPh$_2$)$_2$: Cu$_2$I$_2$(Ph$_2$P(Oxadiazole))(PhP(CH$_2$CH$_2$PPh$_2$)$_2$)$_2$ (12)

The compound 12 is a yellow, fine-crystalline solid.

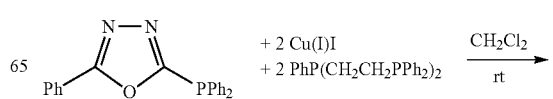

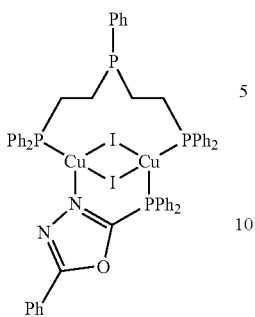

Characterization:

Elemental Analysis:

found: C 49.84; H 3.76; N 1.67

(with one molecule DCM)

calc.: C 49.64; H 3.79; N 2.11

Figure 12:
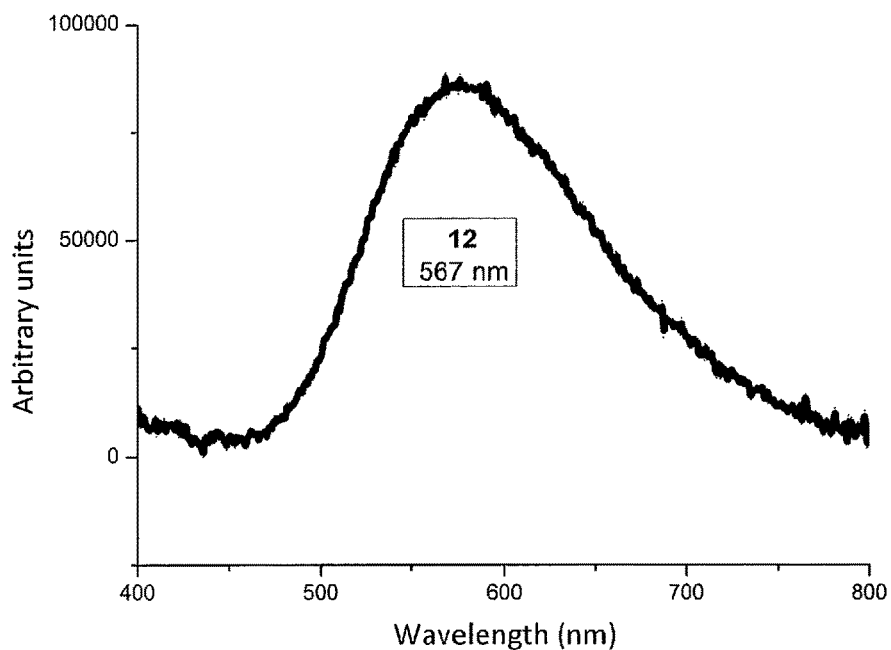
FIG. 12 shows a graphical overview of the emission spectrum of compound 12 in accordance with an embodiment of the present invention.

The emission spectrum is shown in FIG. 12.

XIII. P∩N*=Ph$_2$PMe$_2$Thiaz, L=PPh$_3$: Cu$_2$I$_2$(Ph$_2$PMe$_2$Thiaz)(PPh$_3$)$_2$ (13)

The compound 13 is a yellow, fine-crystalline solid.

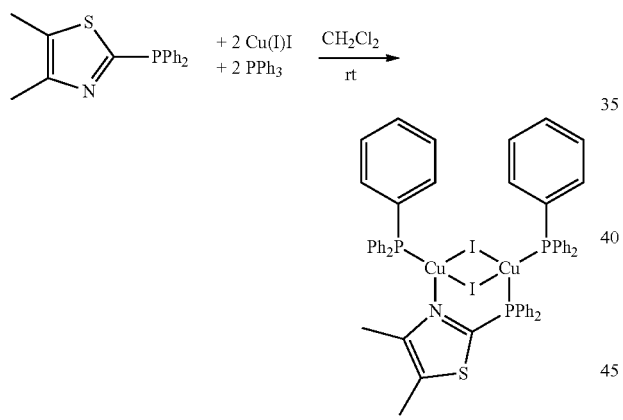

Characterization:

Elemental Analysis:

found: C 52.54; H 4.07; N 1.86; S 2.19 calc.: C 52.92; H 3.85; N 1.16; S 2.67

Figure 13:
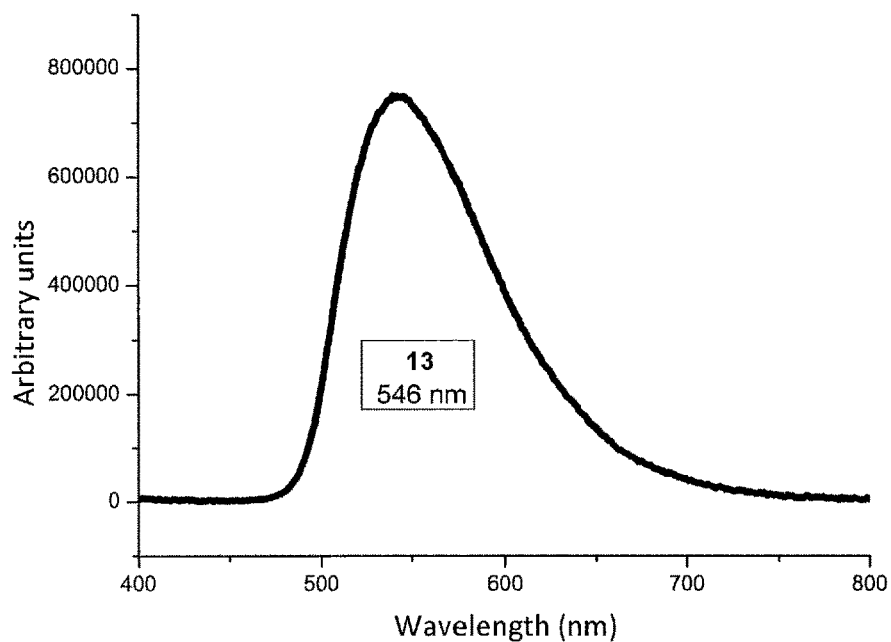
FIG. 13 shows a graphical overview of the emission spectrum of compound 13 in accordance with an embodiment of the present invention.

The emission spectrum is shown in FIG. 13.

XIV. P∩N*=Ph$_2$PThiaz, L=PPh$_3$: Cu$_2$I$_2$(Ph$_2$PThiaz)(PPh$_3$)$_2$ (14)

The compound 14 is a yellow, fine-crystalline solid.

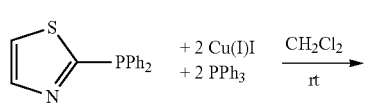

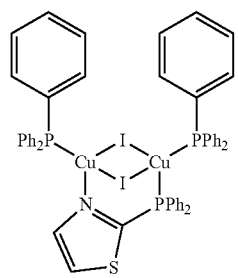

Characterization:

Elemental Analysis:

found: C 52.14; H 3.65; N 1.01; S 2.43 calc.: C 52.14; H 3.60; N 1.19; S 2.73

Figure 14:
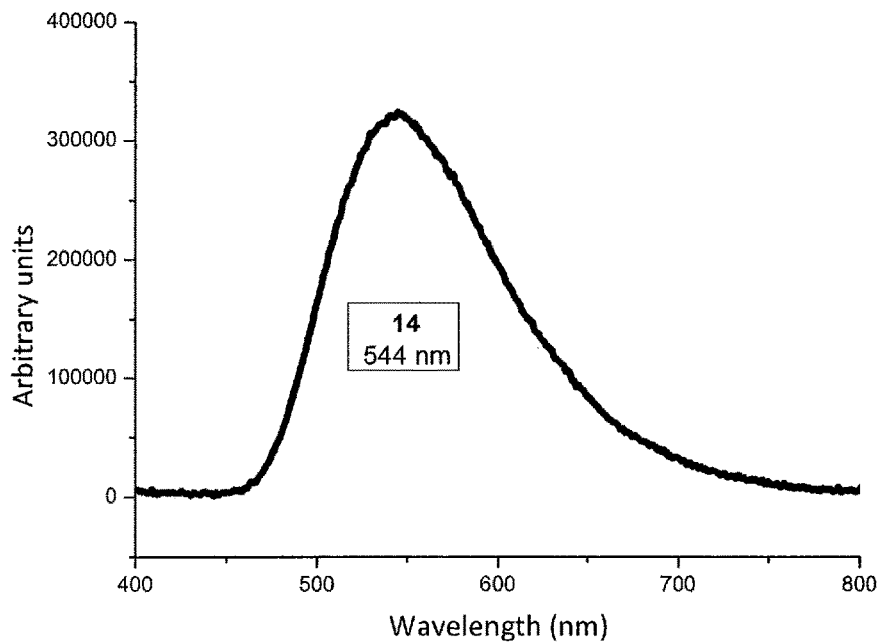
FIG. 14 shows a graphical overview of the emission spectrum of compound 14 in accordance with an embodiment of the present invention.

The emission spectrum is shown in FIG. 14.

XV. P∩N*=Ph$_2$P(Ph$_2$-Triaz), L=PPh$_3$: Cu$_2$I$_2$(Ph$_2$P(Ph$_2$-Triaz))(PPh$_3$)$_2$ (15)

The compound 15 is a white, fine-crystalline solid.

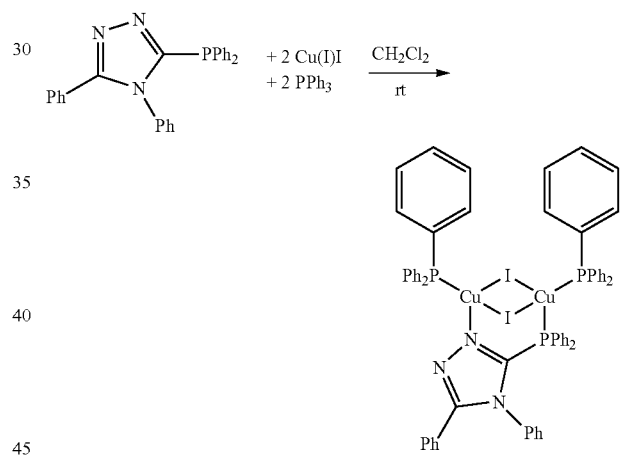

Characterization:

Elemental Analysis:

found: C 55.89; H 3.74; N 2.70 calc.: C 56.13; H 3.82; N 3.15

Figure 15:
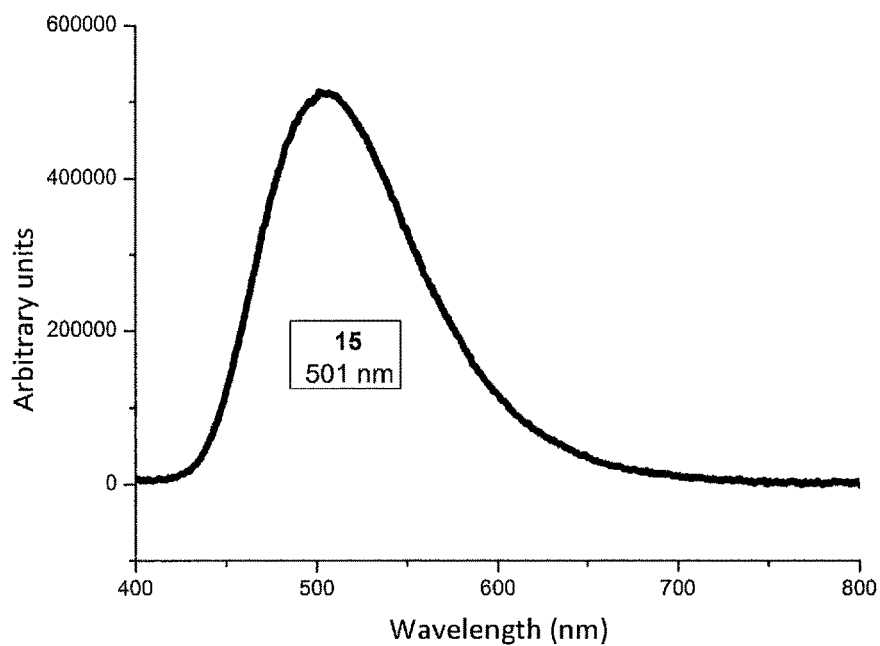
FIG. 15 shows a graphical overview of the emission spectrum of compound 15 in accordance with an embodiment of the present invention.

The emission spectrum is shown in FIG. 15.

XVI. P∩N*=Ph$_2$PTolTriaz, L=PPh$_3$: Cu$_2$I$_2$(Ph$_2$PTolTriaz)(PPh$_3$)$_2$ (16)

The compound 16 is a white, fine-crystalline solid.

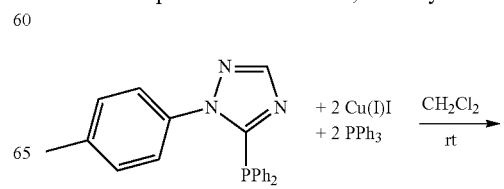

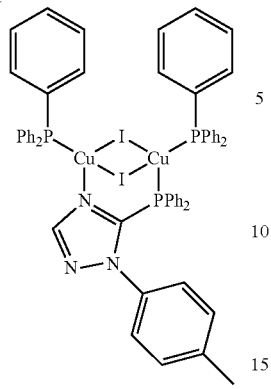

Figure 16:
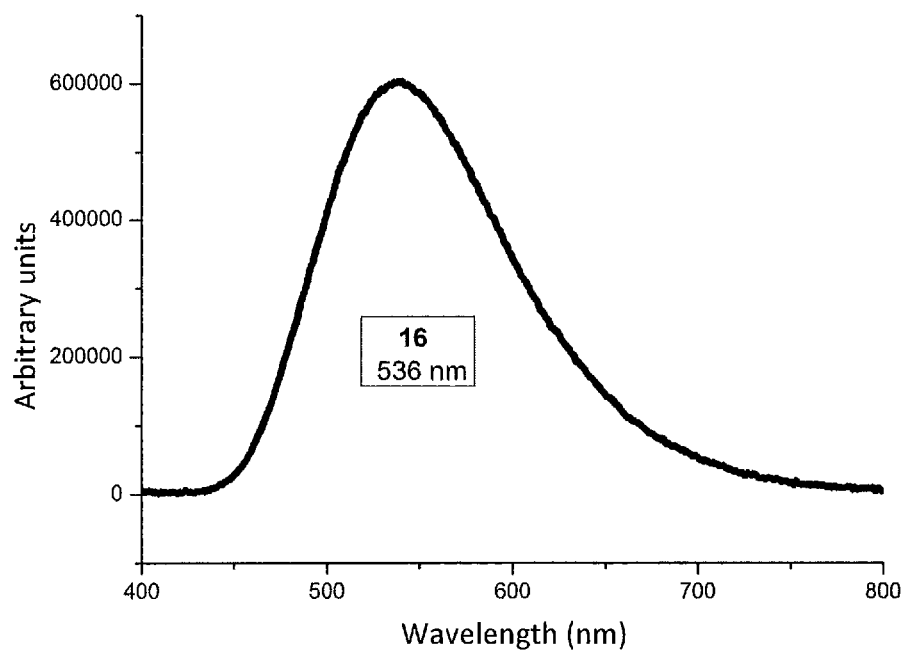
FIG. 16 shows a graphical overview of the emission spectrum of compound 16 in accordance with an embodiment of the present invention.

Characterization:
Elemental Analysis:
found: C 54.26; H 4.05; N 3.36
calc.: C 54.14; H 3.85; N 3.31
The emission spectrum is shown in FIG. 16.

XVII. P∩N*=Ph₂PPrTriaz, L=PPh₃: Cu₂I₂(Ph₂PPrTriaz)(PPh₃)₂ (17)

The compound 17 is a white, fine-crystalline solid.

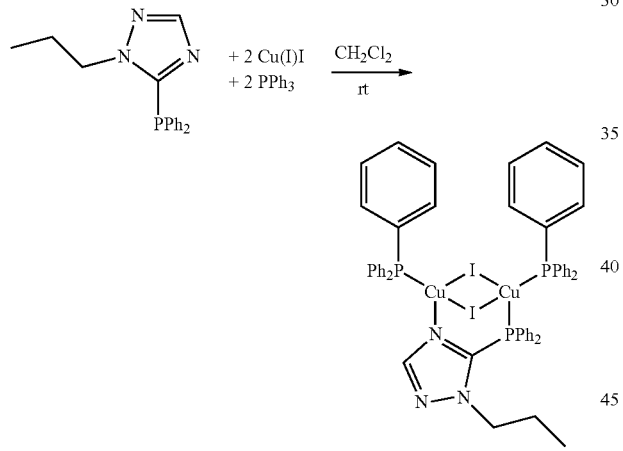

Figure 17:
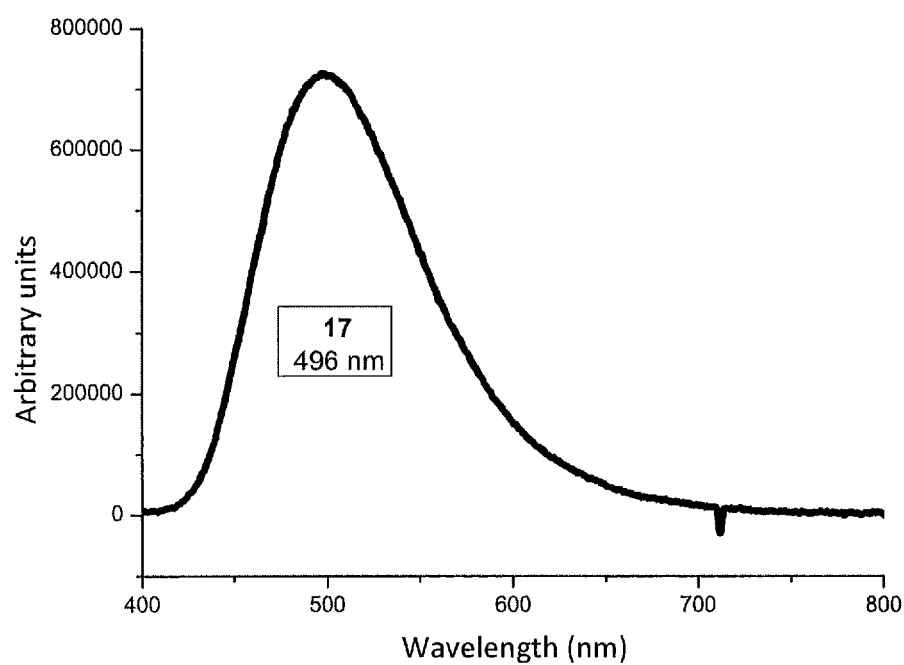
FIG. 17 shows a graphical overview of the emission spectrum of compound 17 in accordance with an embodiment of the present invention.

Characterization:
Elemental Analysis:
found: C 52.77; H 4.05; N 3.11
calc.: C 53.01; H 4.03; N 3.50
The emission spectrum is shown in FIG. 17.

XVIII. P∩N*=Ph₂PPentTriaz, L=PPh₃: Cu₂I₂(Ph₂PPentTriaz)(PPh₃)₂ (18)

The compound 18 is a white, fine-crystalline solid.

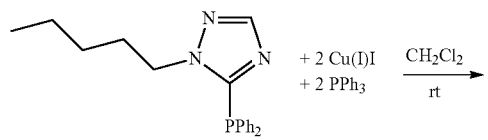

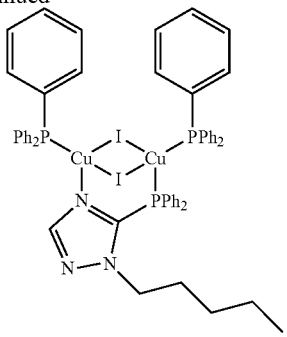

Figure 18:
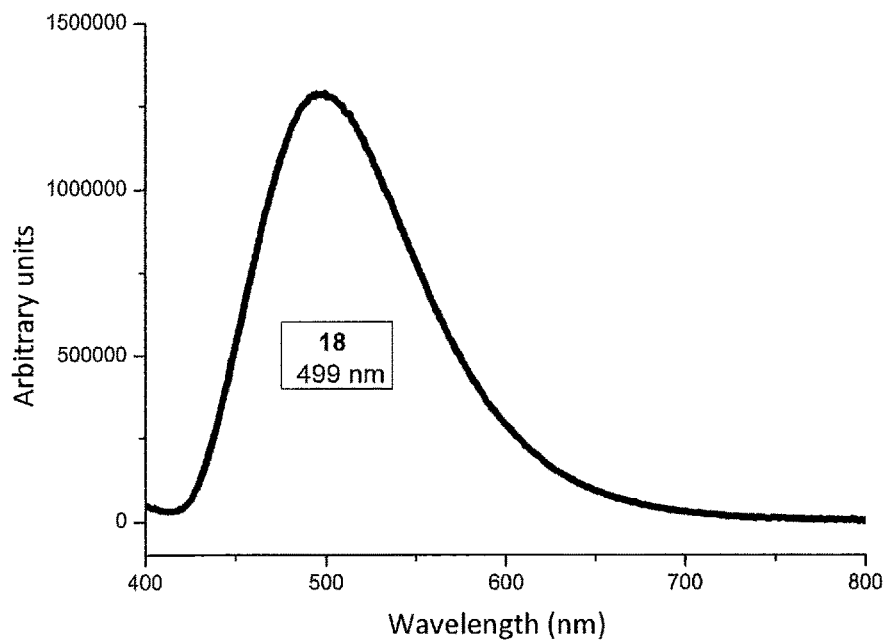
FIG. 18 shows a graphical overview of the emission spectrum of compound 18 in accordance with an embodiment of the present invention.

Characterization:
Elemental Analysis:
found: C 53.55; H 4.34; N 3.65
calc.: C 53.76; H 4.27; N 3.42
The emission spectrum is shown in FIG. 18.

XIX. P∩N*=Ph₂PEtHexTriaz, L=PPh₃: Cu₂I₂(Ph₂PEtHexTriaz)(PPh₃)₂ (19)

The compound 19 is a white, fine-crystalline solid.

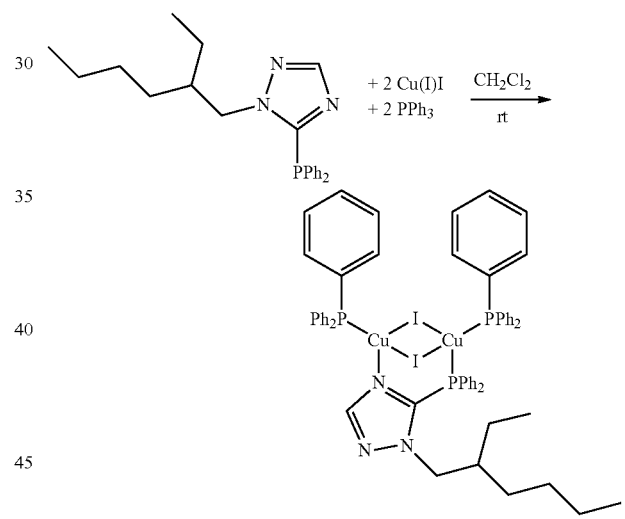

Figure 19:
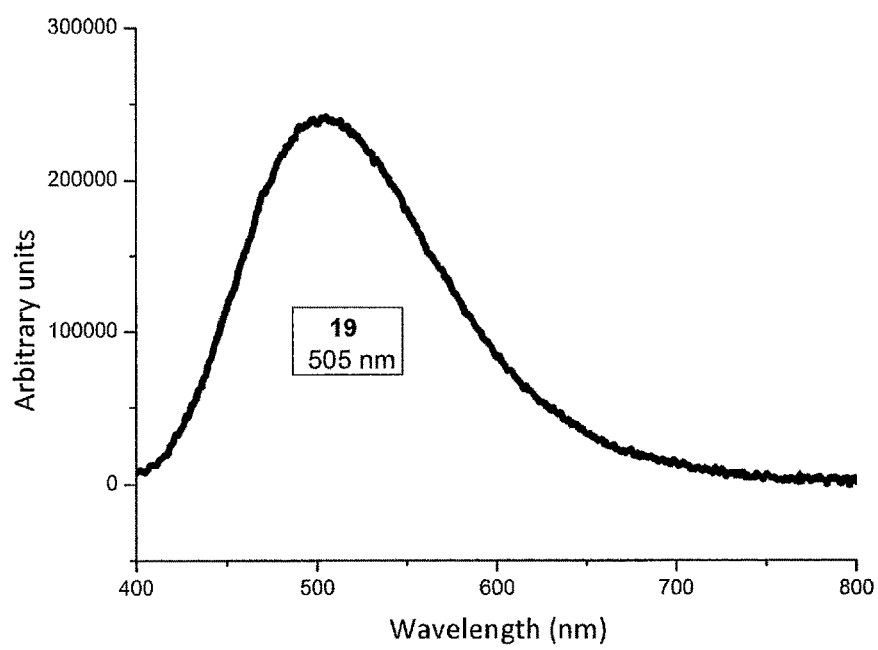
FIG. 19 shows a graphical overview of the emission spectrum of compound 19 in accordance with an embodiment of the present invention.

Characterization:
Elemental Analysis:
found: C 53.70; H 4.36; N 2.63
calc.: C 53.50; H 4.53; N 3.20
The emission spectrum is shown in FIG. 19.

XX. P∩N*=Ph₂PBnTriaz, L=PPh₃: Cu₂I₂(Ph₂PBnTriaz)(PPh₃)₂ (20)

The compound 20 is a white, fine-crystalline solid.

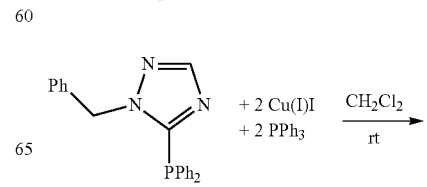

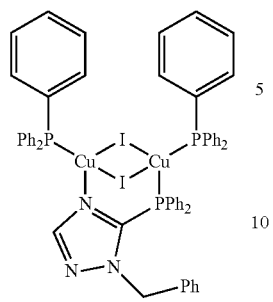

Figure 20:
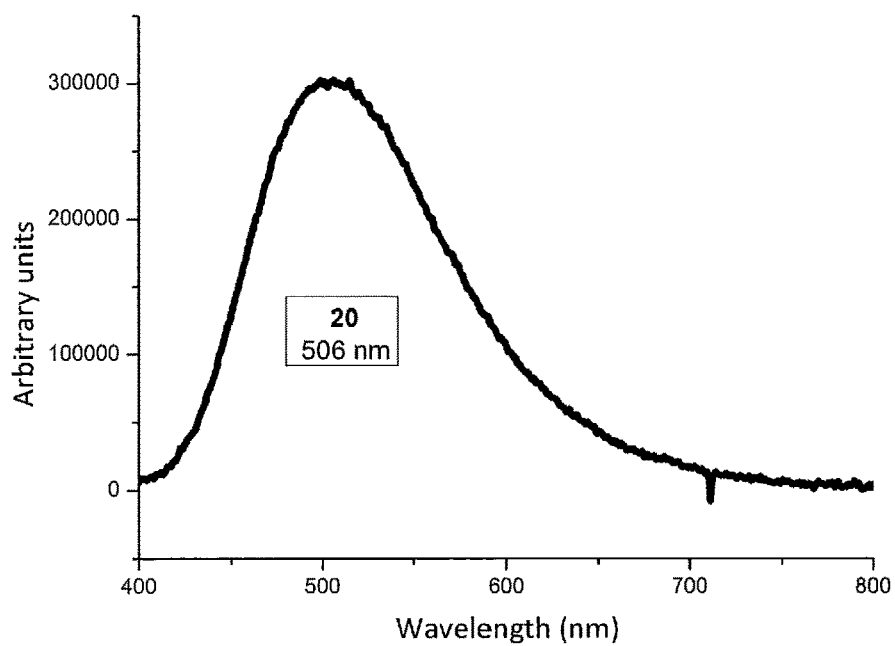
FIG. 20 shows a graphical overview of the emission spectrum of compound 20 in accordance with an embodiment of the present invention.

Characterization:
Elemental Analysis:
found: C 54.67; H 3.78; N 3.28
calc.: C 54.82; H 3.87; N 3.36
The emission spectrum is shown in FIG. 20.

XXI. P∩N*=Ph$_2$P(MeImide), L=PPh$_3$: Cu$_2$I$_2$(Ph$_2$P(MeImide))(PPh$_3$)$_2$ (21)

The compound 21 is a white, fine-crystalline solid.

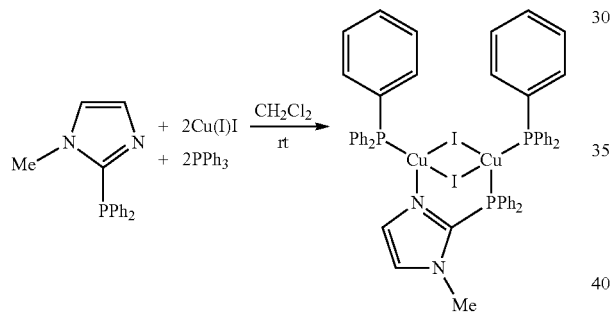

Figure 21:
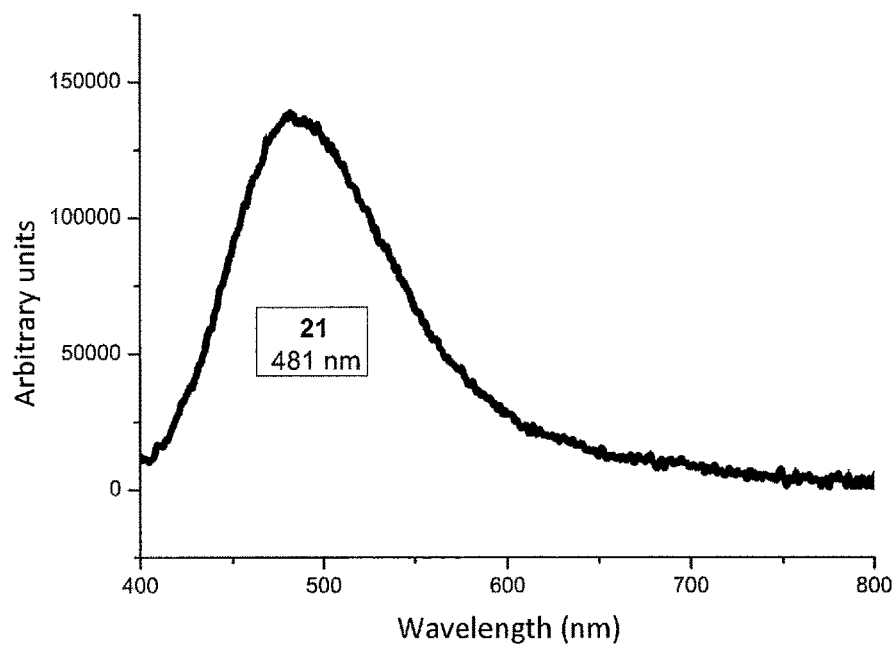
FIG. 21 shows a graphical overview of the emission spectrum of compound 21 in accordance with an embodiment of the present invention.

Characterization:
Elemental Analysis:
found: C 52.38; H 3.84; N 2.33
(with ⅓ molecule DCM)
calc.: C 52.39; H 3.90; N 2.28
The emission spectrum is shown in FIG. 21.

XXII. P∩N*=Ph$_2$P(MeTolImide), L=PPh$_3$: Cu$_2$I$_2$(Ph$_2$P(MeTolImide))(PPh$_3$)$_2$ (22)

The compound 22 is a white, fine-crystalline solid.

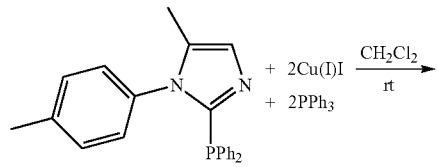

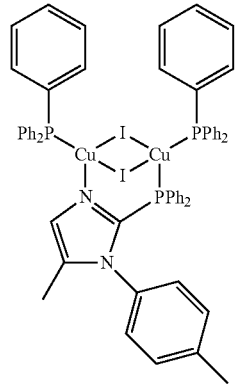

Figure 22:
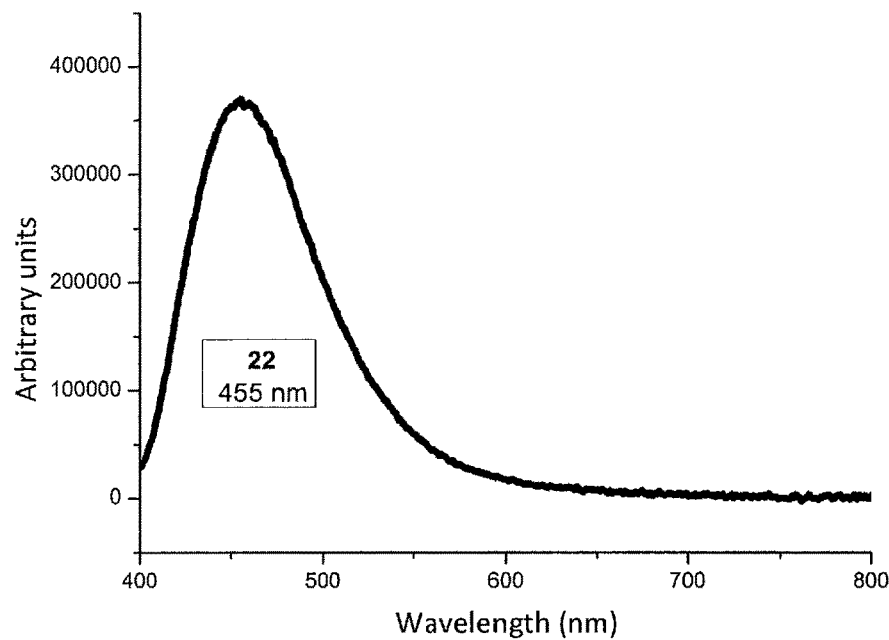
FIG. 22 shows a graphical overview of the emission spectrum of compound 22 in accordance with an embodiment of the present invention.

Characterization:
Elemental Analysis:
found: C 55.58; H 4.05; N 1.74
(with ¼ molecule DCM)
calc.: C 55.46; H 4.05; N 2.18
The emission spectrum is shown in FIG. 22.

XXIII. P∩N*=Ph$_2$P(iBuBenzimide), L=PPh$_3$: Cu$_2$I$_2$(Ph$_2$P(iBuBenzimide)(PPh$_3$)$_2$ (23)

The compound 23 is a white, fine-crystalline solid.

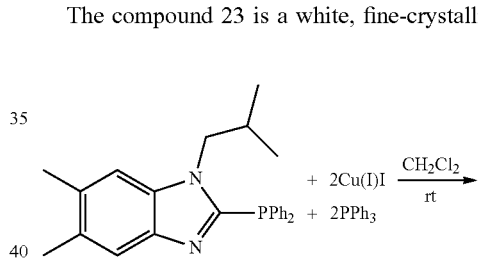

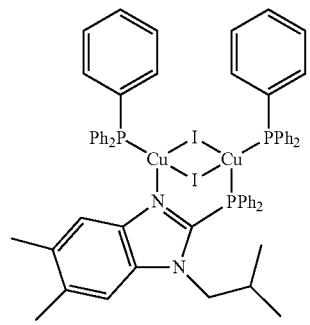

Figure 23:
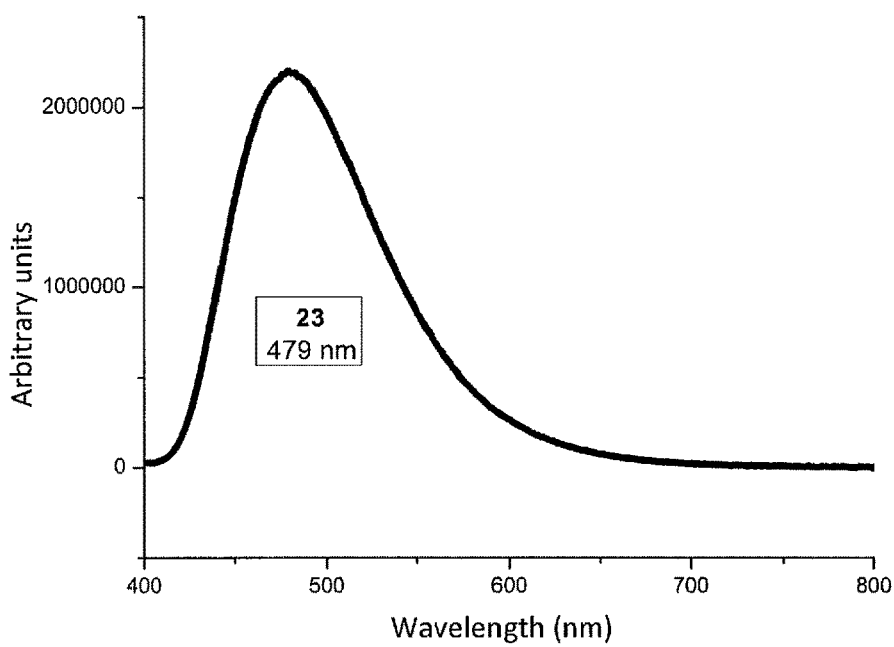
FIG. 23 shows a graphical overview of the emission spectrum of compound 23 in accordance with an embodiment of the present invention.

Characterization:
Elemental Analysis:
found: C 56.20; H 4.55; N 1.69
(with ¼ molecule DCM)
calc.: C 56.02; H 4.41; N 2.13
The emission spectrum is shown in FIG. 23.

XXIV. P∩N*=Ph$_2$P(OctBenzimide), L=PPh$_3$: Cu$_2$I$_2$(Ph$_2$P(OctBenzimide)(PPh$_3$)$_2$ (24)

The compound 24 is a white, fine-crystalline solid.

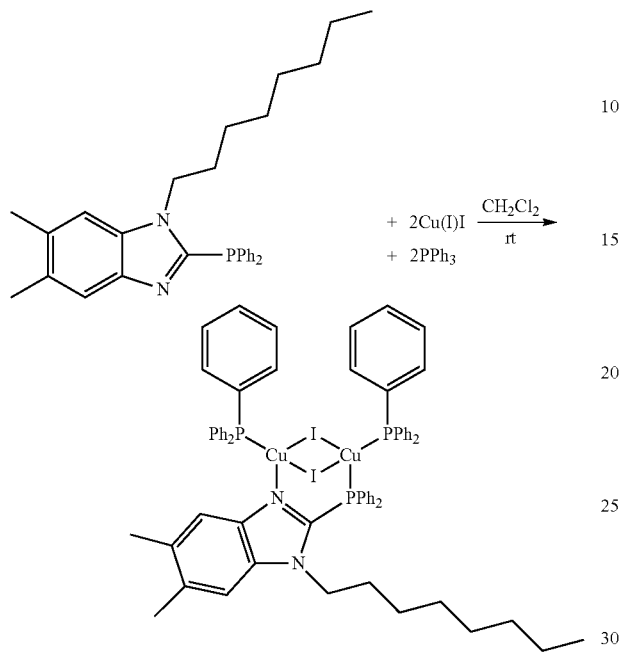

Figure 24:
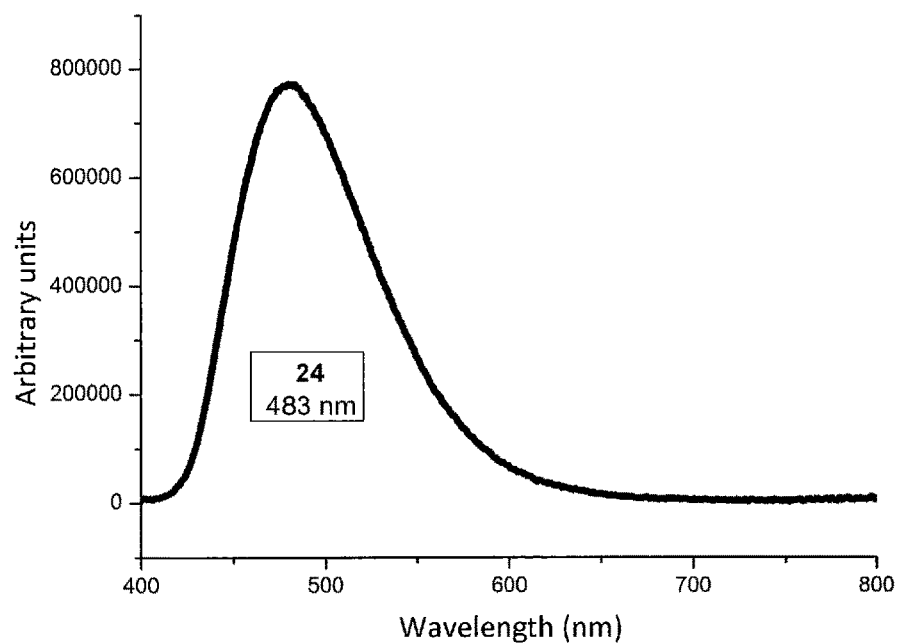
FIG. 24 shows a graphical overview of the emission spectrum of compound 24 in accordance with an embodiment of the present invention.

Characterization:
Elemental Analysis:
found: C 57.60; H 4.79; N 1.93
calc.: C 57.91; H 4.86; N 2.08
The emission spectrum is shown in FIG. 24.

XXV. P∩N*=Ph$_2$P(PhenanthroImide), L=PPh$_3$: Cu$_2$I$_2$(Ph$_2$P(PhenanthroImide)(PPh$_3$)$_2$ (25)

The compound 25 is a white, fine-crystalline solid.

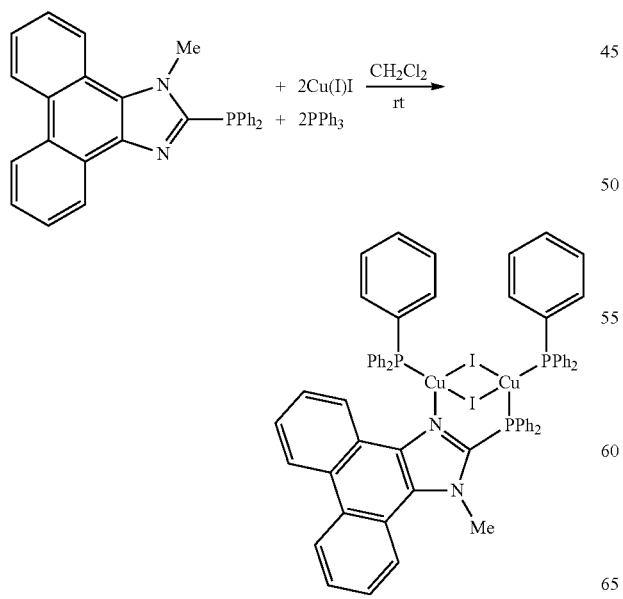

Characterization:
Elemental Analysis:
found: C 57.66; H 3.88; N 1.91
(with ⅛ molecule DCM)
calc.: C 57.45; H 3.86; N 2.09

XXVI. P∩N*=Ph$_2$P(Ph$_2$-Triaz), L=PPh$_3$: Cu$_2$I$_2$(Ph$_2$P(Ph$_2$-Triaz)(PPh$_3$)$_2$ (26)

The compound 26 is a white, fine-crystalline solid.

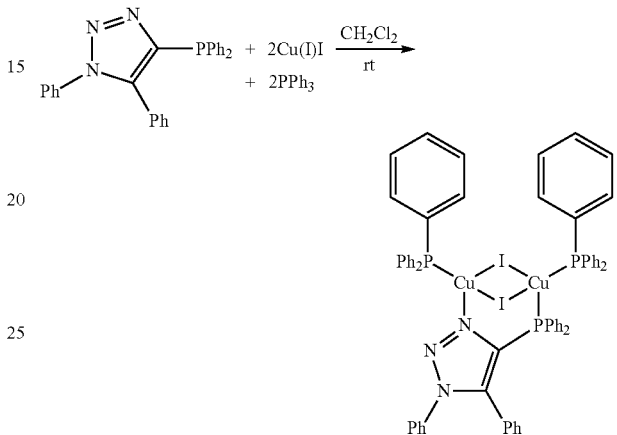

Figure 25:
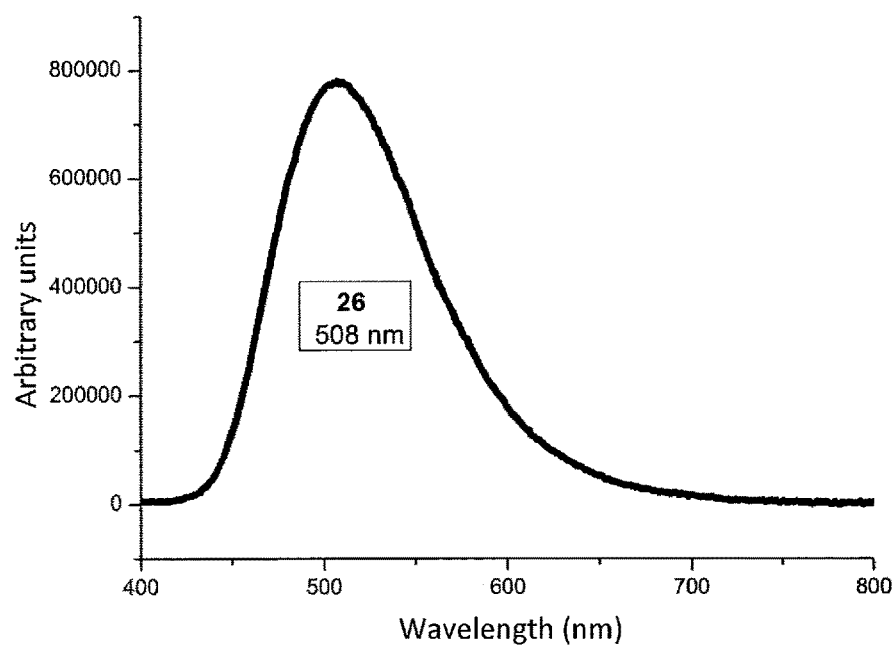
FIG. 25 shows a graphical overview of the emission spectrum of compound 26 in accordance with an embodiment of the present invention.

Characterization:
The emission spectrum is shown in FIG. 25.

XXVII. P∩N*=Ph$_2$Ppic, L=P(p-OMePh)$_3$: Cu$_2$I$_2$(Ph$_2$Ppic)(P(p-OMePh)$_3$)$_2$ (27)

The compound 27 is a yellowish, fine-crystalline solid.

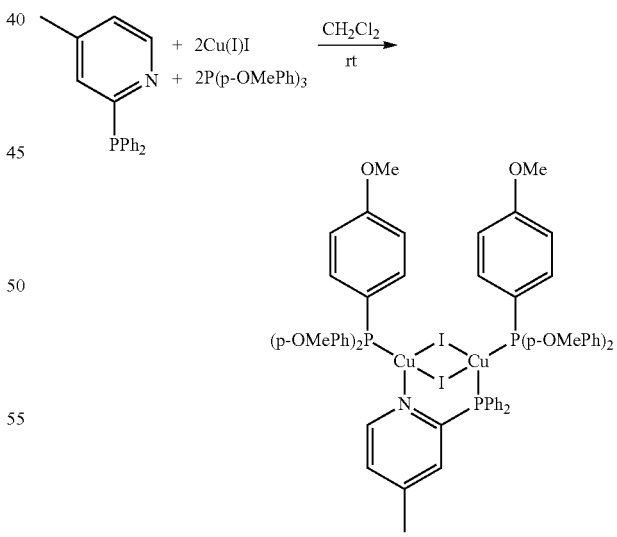

Figure 26:
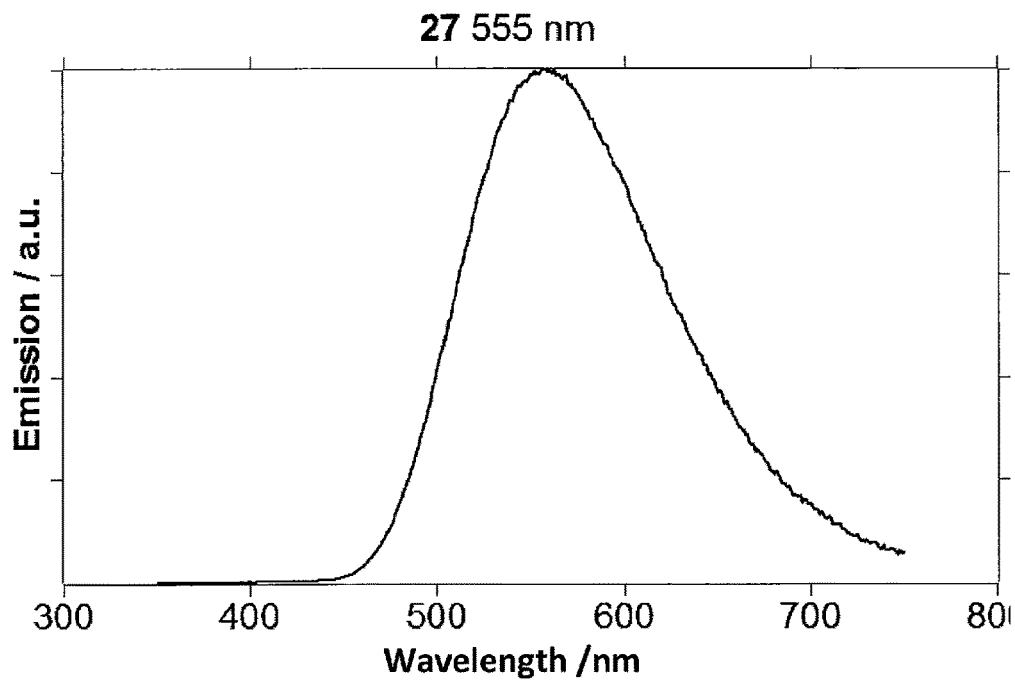
FIG. 26 shows a graphical overview of the emission spectrum of compound 27 in accordance with an embodiment of the present invention.

Characterization:
Elemental Analysis:
found: C 51.89; H 4.33; N 0.61
(with ½ molecule DCM)
calc.: C 51.70; H 4.23; N 1.00
The emission spectrum is shown in FIG. 26.

XXVIII. P∩N*=Ph₂Ppic, L=P(2-Furyl)₃: Cu₂I₂(Ph₂Ppic)(P(2-Furyl)₃)₂ (28)

The compound 28 is a white, fine-crystalline solid.

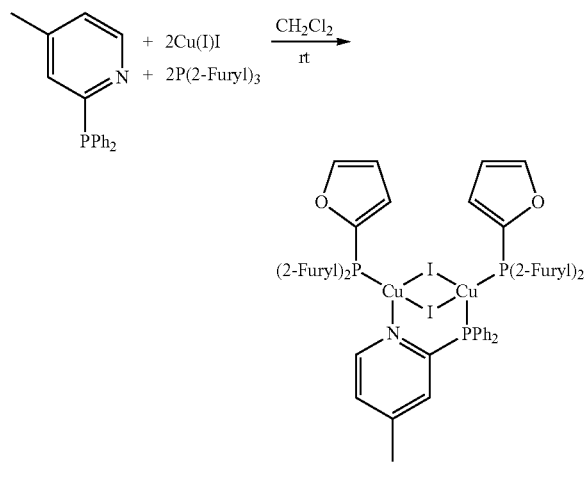

Figure 27:
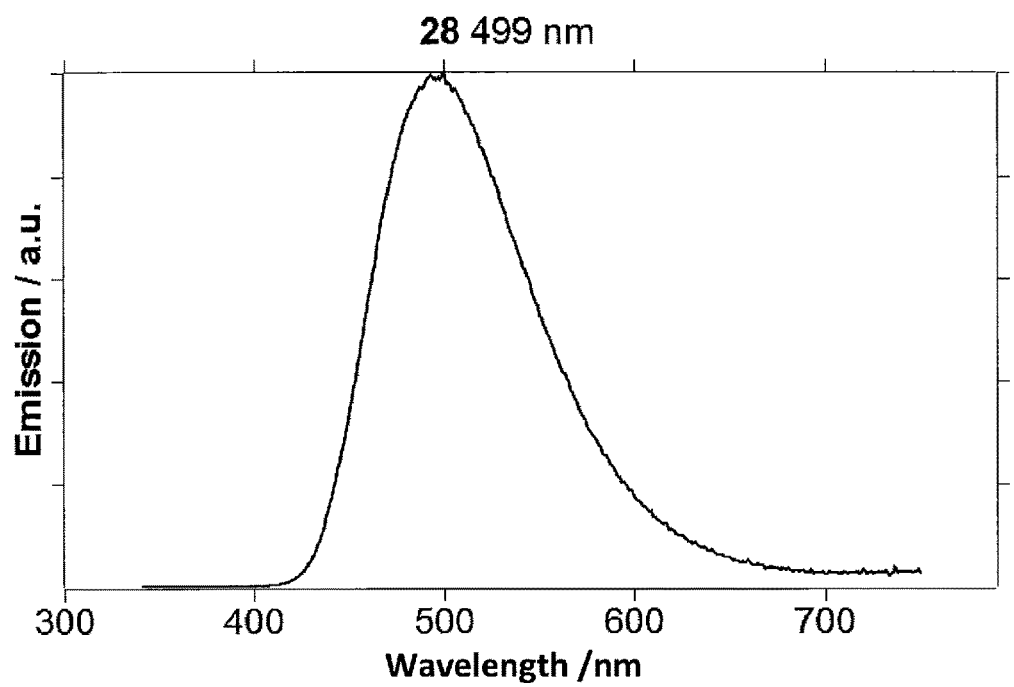
FIG. 27 shows a graphical overview of the emission spectrum of compound 28 in accordance with an embodiment of the present invention.

Characterization:
Elemental Analysis:
found: C 44.56; H 3.60; N 0.91
calc.: C 44.94; H 3.05; N 1.25
The emission spectrum is shown in FIG. 27.

XXIX. P∩N*=Ph₂Ppic, L=P(n-Octyl)₃: Cu₂I₂(Ph₂Ppic)(P(n-Octyl)₃)₂ (29)

The compound 29 is a yellowish, fine-crystalline solid.

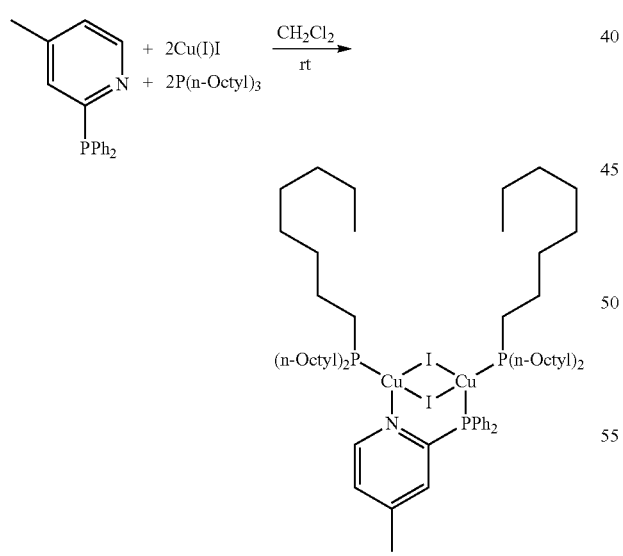

Figure 28:
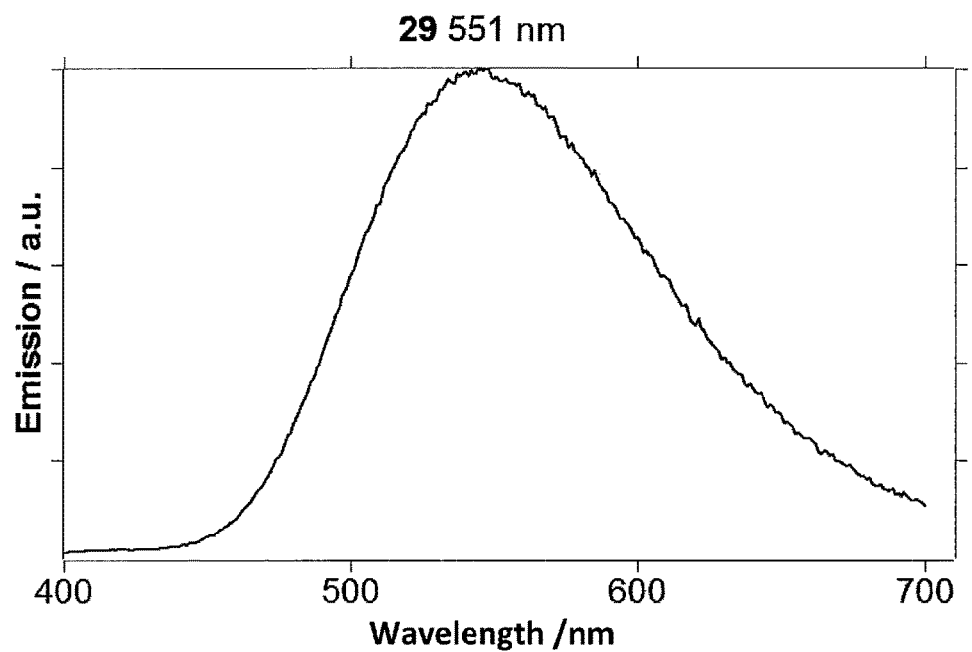
FIG. 28 shows a graphical overview of the emission spectrum of compound 29 in accordance with an embodiment of the present invention.

Characterization:
Elemental Analysis:
found: C 56.76; H 8.85; N 0.60
calc.: C 56.64; H 8.85; N 1.00
The emission spectrum is shown in FIG. 28.

XXX. P∩N*=Ph₂Ppic, L=P(c-Hexyl)₃: Cu₂I₂(Ph₂Ppic)(P(c-Hexyl)₃)₂ (30)

The compound 30 is a yellowish, fine-crystalline solid.

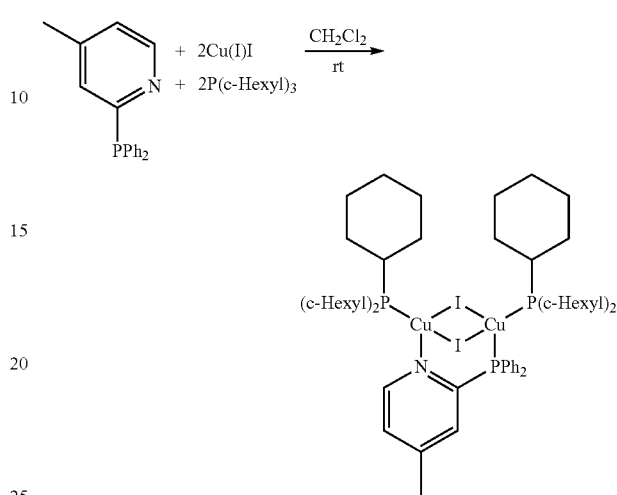

Figure 29:
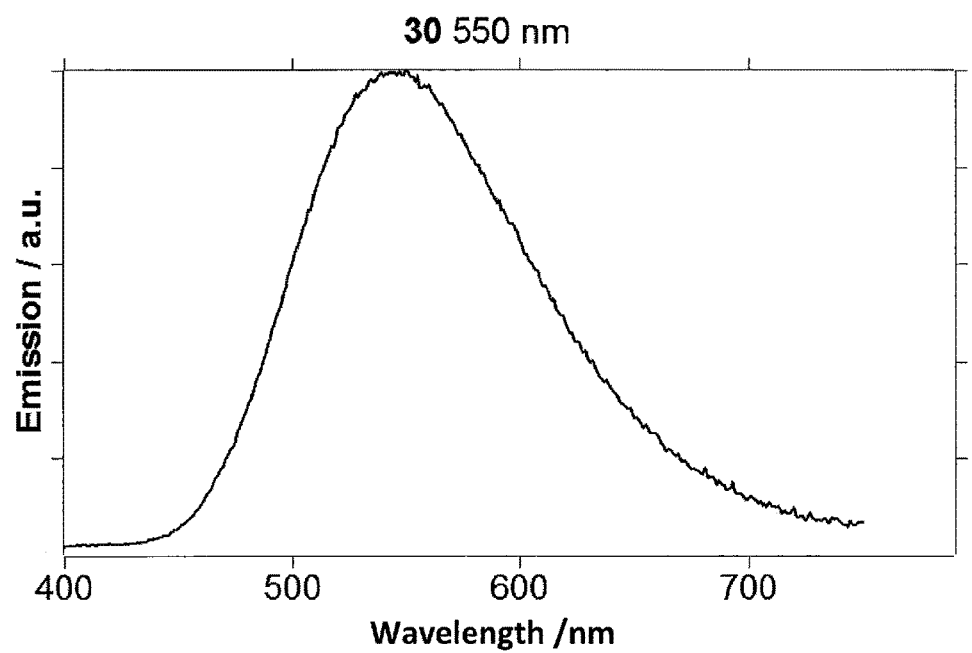
FIG. 29 shows a graphical overview of the emission spectrum of compound 30 in accordance with an embodiment of the present invention.

Characterization:
The emission spectrum is shown in FIG. 29.

XXXI. P∩N*=Ph₂Ppic, L=P(OEt)₃: Cu₂I₂(Ph₂Ppic)(P(OEt)₃)₂ (31)

The compound 31 is a greenish, fine-crystalline solid.

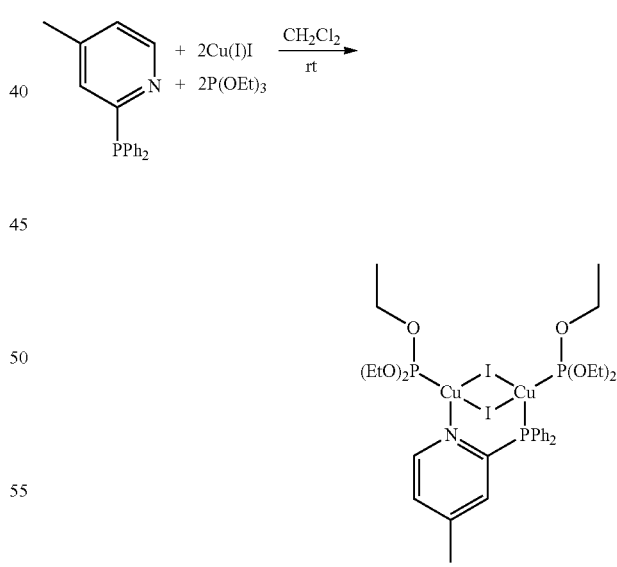

Figure 30:
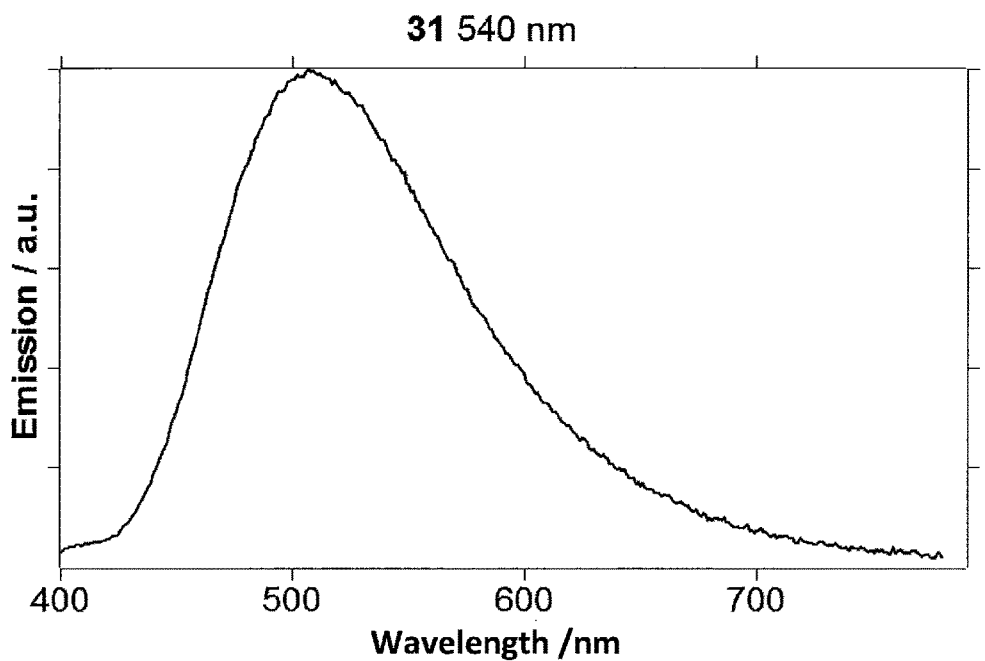
FIG. 30 shows a graphical overview of the emission spectrum of compound 31 in accordance with an embodiment of the present invention.

Characterization:
Elemental Analysis:
found: C 35.73; H 4.78; N 1.01
(with ⅓ molecule DCM)
calc.: C 35.76; H 4.62; N 1.37
The emission spectrum is shown in FIG. 30.

XXXII. P∩N*=Ph₂PPyButyne, L=P(OEt)₃: Cu₂I₂
(Ph₂PyButyne)(P(OEt)₂ (32)

The compound 32 is a yellowish, fine-crystalline solid.

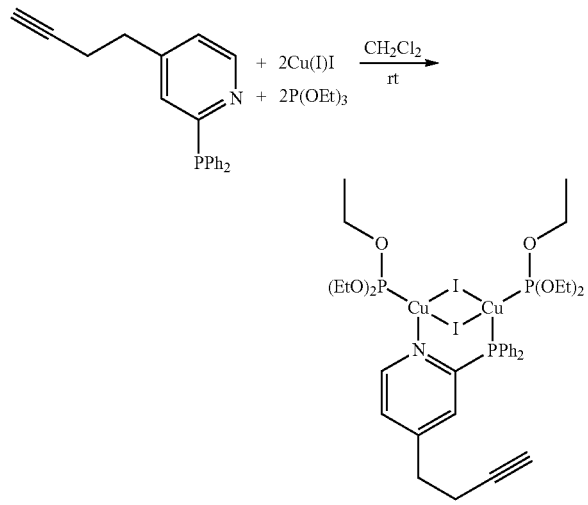

Figure 31:
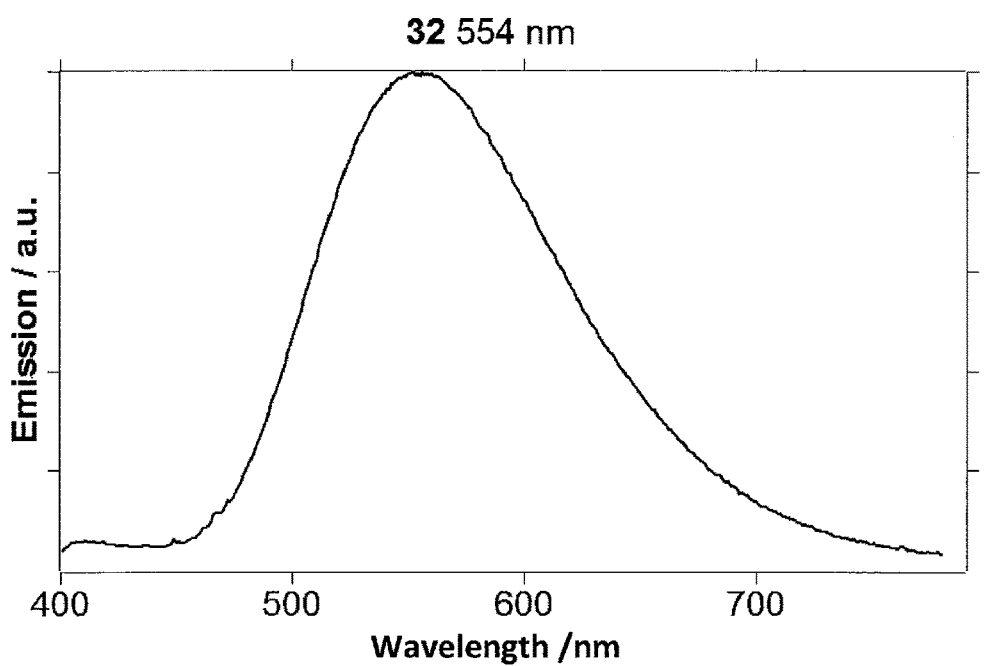
FIG. 31 shows a graphical overview of the emission spectrum of compound 32 in accordance with an embodiment of the present invention.

Characterization:
Elemental Analysis:
found: C 37.25; H 4.90; N 0.90
(with ½ molecule DCM)
calc.: C 37.57; H 4.61; N 1.30
The emission spectrum is shown in FIG. 31.

XXXIII. P∩N*=Ph₂Ppic, L=P(OiPr)₃: Cu₂I₂
(Ph₂Ppic)(P(OiPr)₃)₂ (33)

The compound 33 is a greenish, fine-crystalline solid.

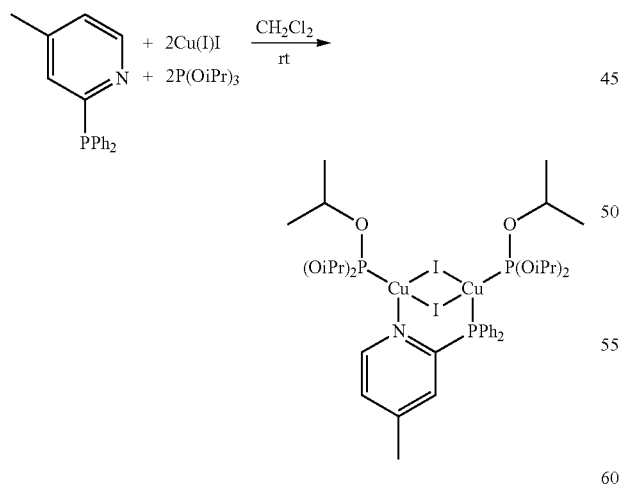

Figure 32:
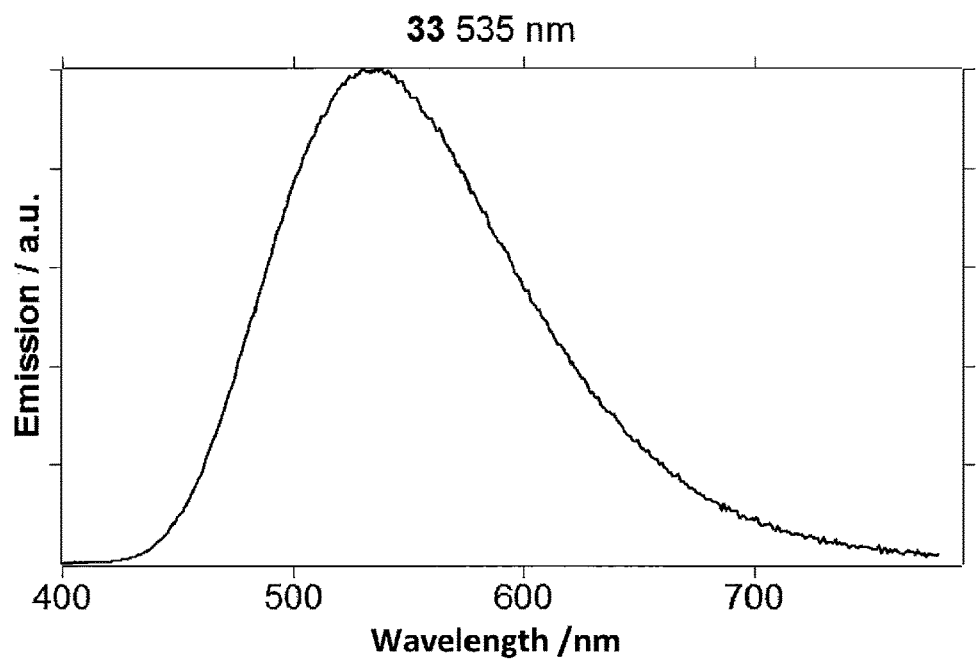
FIG. 32 shows a graphical overview of the emission spectrum of compound 33 in accordance with an embodiment of the present invention.

Characterization:
Elemental Analysis:
found: C 40.53; H 5.41; N 1.03
calc.: C 40.23; H 5.44; N 1.30
The emission spectrum is shown in FIG. 32.

XXXIV. P∩N*=Ph₂Ppic, L=PPh₂OEt: Cu₂I₂
(Ph₂Ppic)(PPh₂OEt)₂ (34)

The compound 34 is a yellowish, fine-crystalline solid.

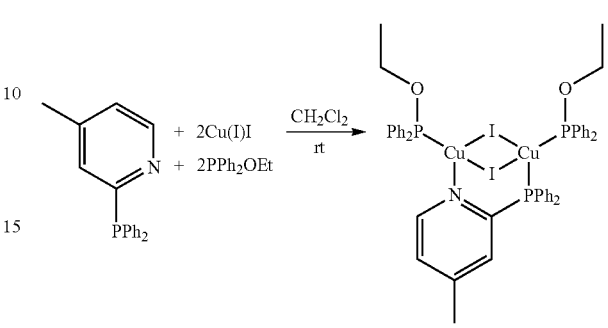

Figure 33:
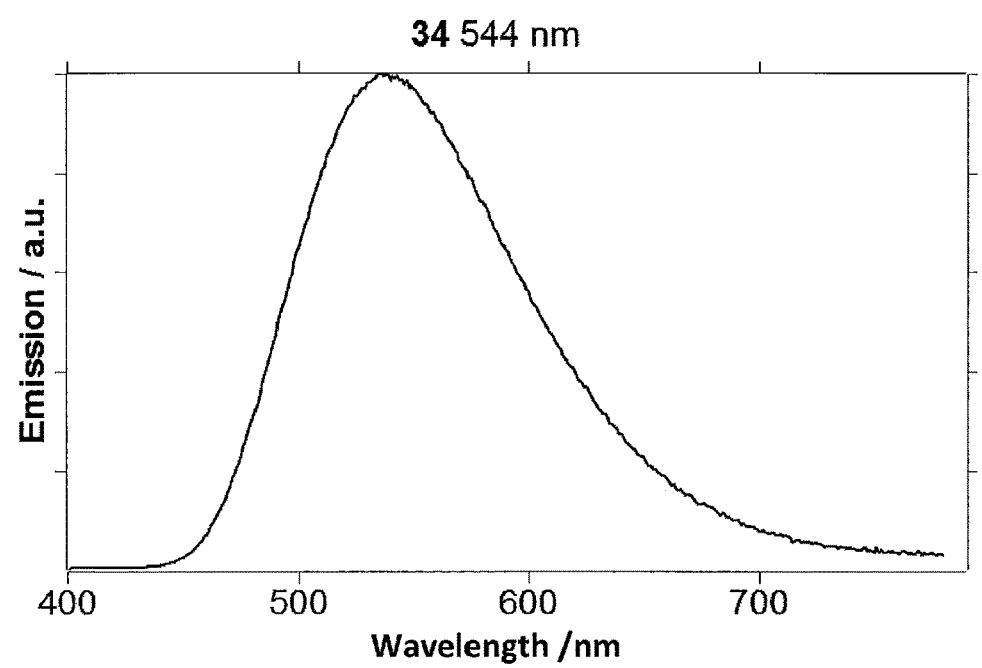
FIG. 33 shows a graphical overview of the emission spectrum of compound 34 in accordance with an embodiment of the present invention.

Characterization:
Elemental Analysis:
found: C 50.10; H 4.41; N 1.23
(with ⅓ molecule DCM)
calc.: C 50.43; H 4.29; N 1.00
The emission spectrum is shown in FIG. 33.

XXXV. P∩N*=Ph₂Ppic, L=PPhOEt₂: Cu₂I₂
(Ph₂Ppic)(PPhOEt₂)₂ (35)

The compound 35 is a slightly greenish, fine-crystalline solid.

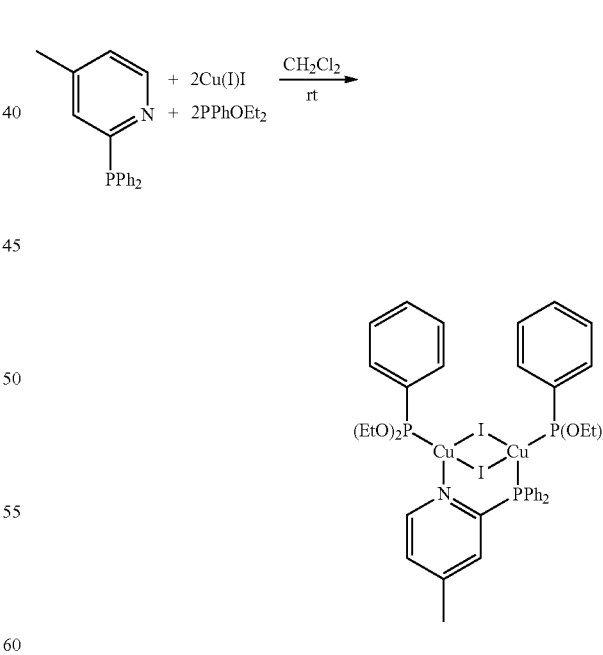

Figure 34:
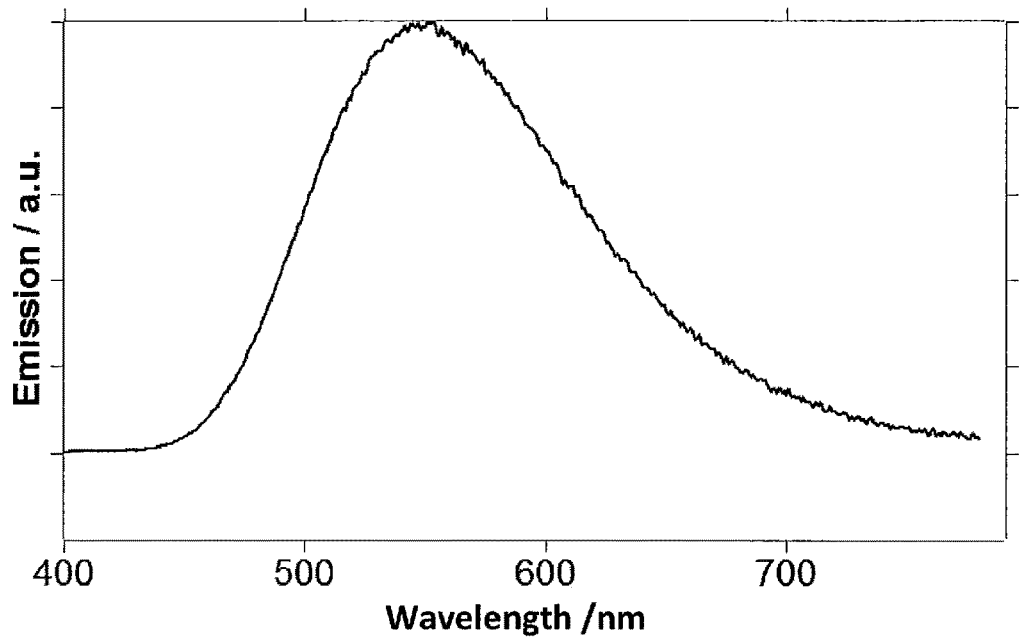
FIG. 34 shows a graphical overview of the emission spectrum of compound 35 in accordance with an embodiment of the present invention.

Characterization:
Elemental Analysis:
found: C 43.18; H 4.10; N 1.55
calc.: C 43.28; H 4.40; N 1.33
The emission spectrum is shown in FIG. 34.

XXXVI. P∩N*=Ph₂Ppic, L=PPh₂Bu: Cu₂I₂(Ph₂Ppic)(PPh₂Bu)₂ (36)

The compound 36 is a slightly greenish, fine-crystalline solid.

XXXVIII. P∩N*=Ph₂P(TolOxadiazole), L=DPEphos: Cu₂I₂(Ph₂P(Oxadiazole)(DPEphos) (38)

The compound 38 is a white, fine-crystalline solid.

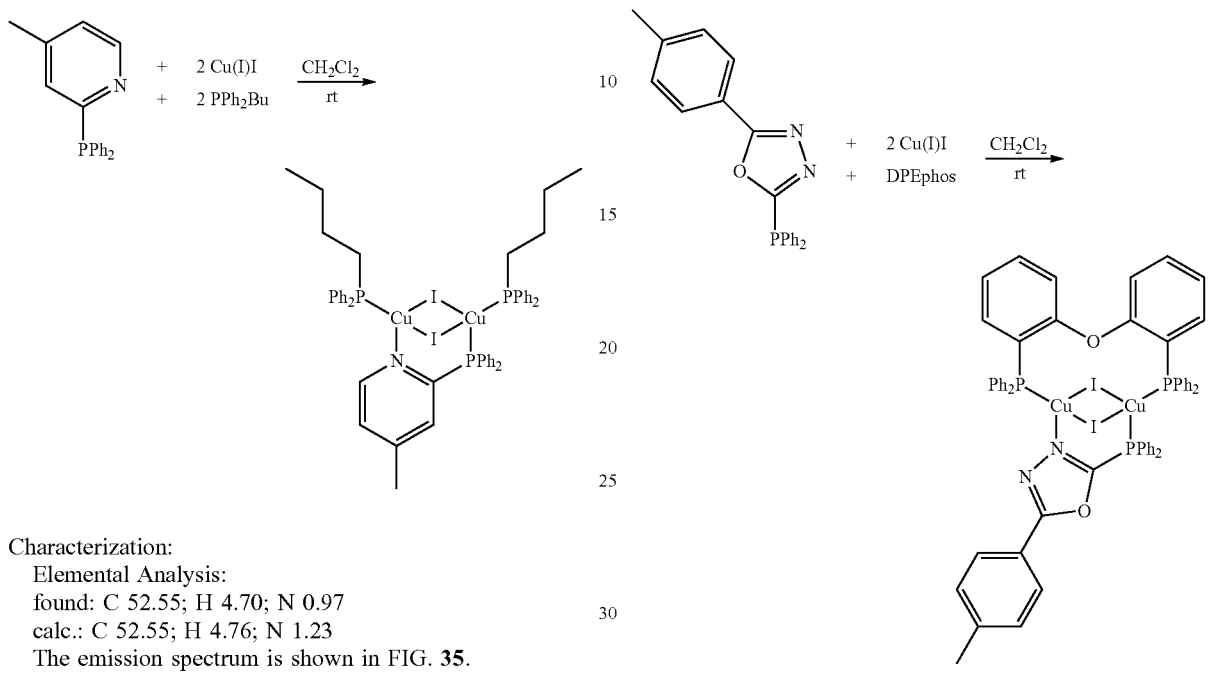

Figure 35:
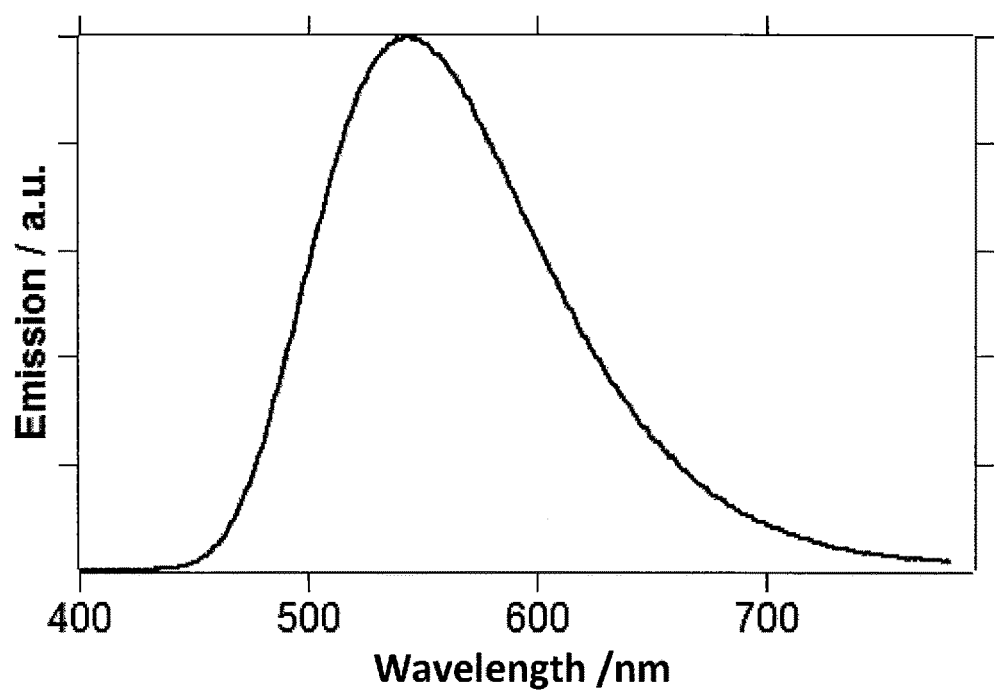
FIG. 35 shows a graphical overview of the emission spectrum of compound 36 in accordance with an embodiment of the present invention.

Characterization:
Elemental Analysis:
found: C 52.55; H 4.70; N 0.97
calc.: C 52.55; H 4.76; N 1.23
The emission spectrum is shown in FIG. 35.

XXXVII. P∩N*=Ph₂P(MeTolImide), L=DPEphos: Cu₂I₂(Ph₂P(MeTolImide)(PPEphos) (37)

The compound 37 is a white, fine-crystalline solid.

Characterization:
Elemental Analysis:
found: C 51.00; H 3.46; N 2.22
calc.: C 50.89; H 3.43; N 2.33

XXXIX. P∩N*=(Ph₂PThiaz), L=DPEphos: Cu₂I₂(Ph₂PThiaz)(DPEphos) (39)

The compound 39 is a white, fine-crystalline solid.

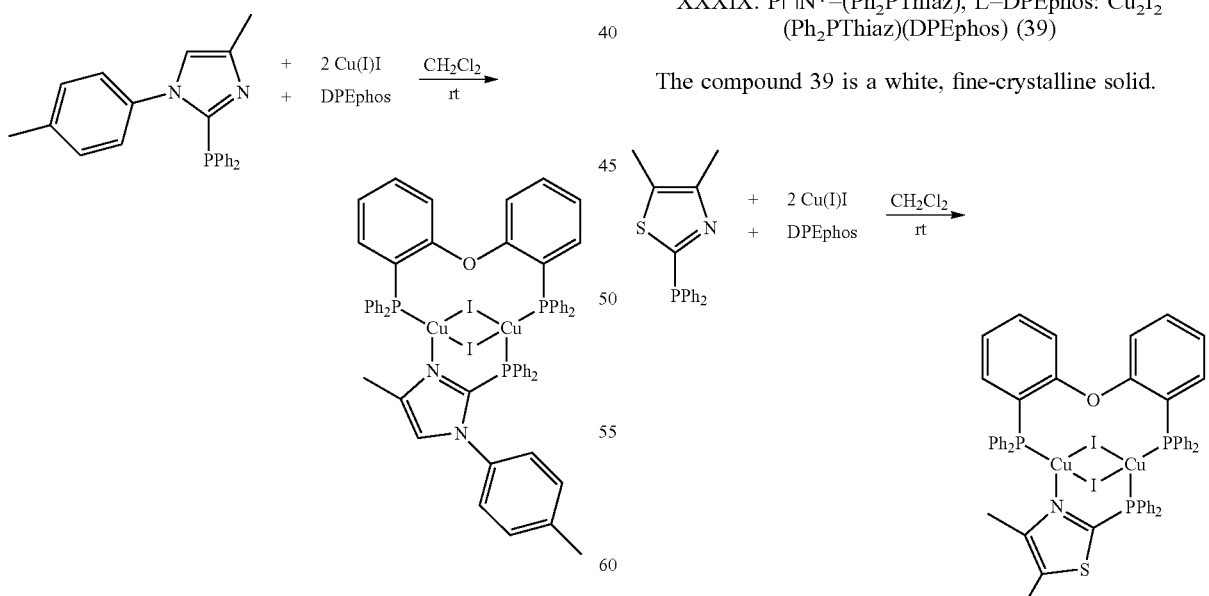

Figure 36:
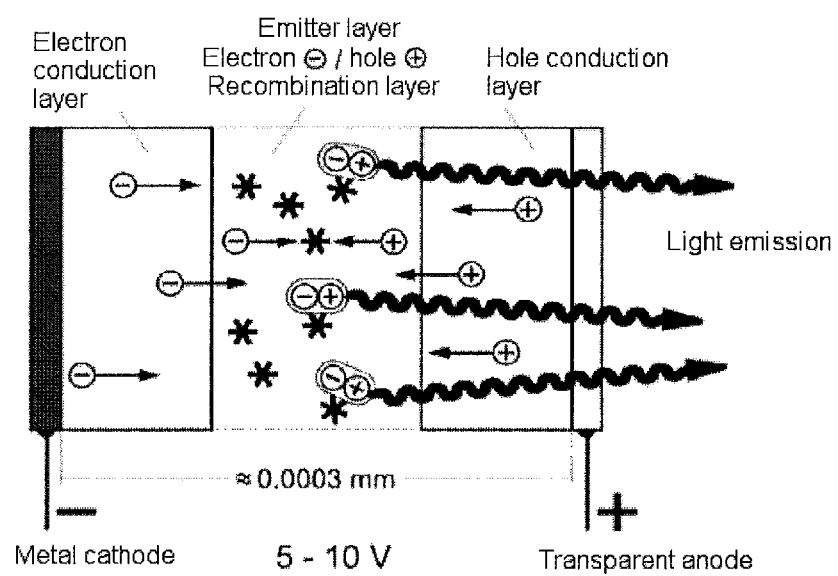
FIG. 36 shows a schematic and simplified diagram of an Organic Light Emitting Diode (OLED) in accordance with an embodiment of the present invention.

Characterization:
Elemental Analysis:
found: C 48.62; H 3.38; N 3.01
(with 1 molecule DCM)
calc.: C 48.50; H 3.44; N 3.26
The emission spectrum is shown in FIG. 36.

Characterization:
Elemental Analysis:
found: C 48.57; H 3.43; N 1.03; S 2.74
calc.: C 48.80; H 3.49; N 1.21; S 2.77

XXXX. P∩N*=Ph₂P(TolOxadiazole), L=4-Ethy-nylPhPPh₂: Cu₂I₂(Ph₂P(TolOxadiazole)(4-EthynylPhPPh₂)₂ (40)

The compound 40 is a yellow, fine-crystalline solid.

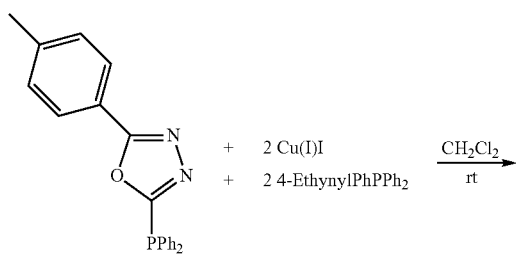

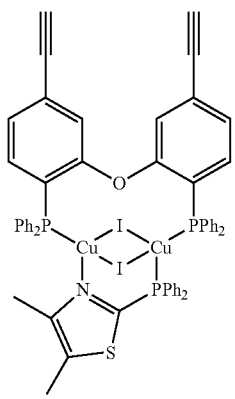

Characterization:
Elemental Analysis:
found: C 53.40; H 3.84; N 0.84; S 2.60
(with ½ molecule DCM)
calc.: C 53.40; H 3.66; N 1.08; S 2.48

XXXXII. P∩N=(Ph₂PPyrim), L=PPh₃: Cu₂I₂(Ph₂PPyrim)(PPh₃)₂ (42)

The compound 42 is an orange-colored, fine-crystalline solid.

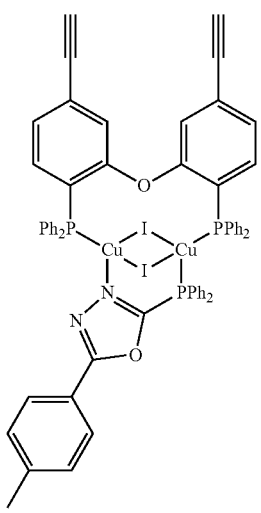

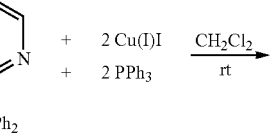

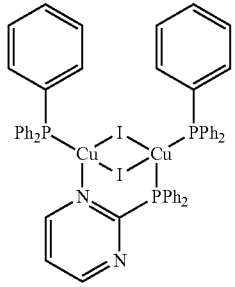

Characterization:
Elemental Analysis:
found: C 55.47; H 3.70; N 2.08
(with ¼ molecule DCM)
calc.: C 55.77; H 3.63; N 2.12

XXXXI. P∩N*=(Ph₂PThiaz), L=4-EthynylPhPPh₂: Cu₂I₂(Ph₂PThiaz)(4-EthynylPhPPh₂)₂ (41)

The compound 41 is a yellow, fine-crystalline solid.

Characterization:
Elemental Analysis:
found: C 53.92; H 4.31; N 2.11
(with ½ molecule MTBE)
calc.: C 53.93; H 4.07; N 2.31

XXXXIII-XXXV. P∩N*=(Ph₂PPyr), L=PPh₃, X=Cl, Br, I: Cu₂X₂((Ph₂PPyr)(PPh₃)₂ (43-45)

The compounds 43-45 are yellow, fine-crystalline solids.

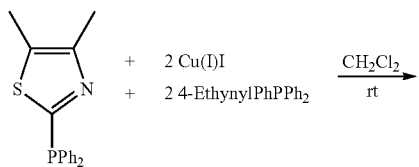

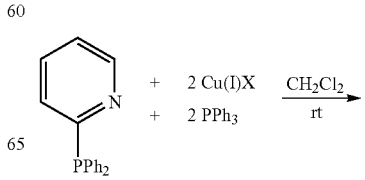

-continued

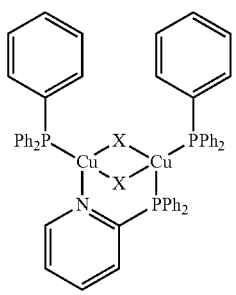

Characterization:
Elemental Analysis:
43 X=Cl:
found: C 64.22; H 4.51; N 1.16
calc.: C 64.57; H 4.50; N 1.42
44 X=Br:
found: C 58.91; H 4.28; N 1.03
calc.: C 58.88; H 4.25; N 1.20
45 X=I:
found: C 54.39; H 3.85; N 0.93
calc.: C 54.47; H 3.79; N 1.20

XXXVI. P∩N*=(Ph$_2$P(iBupy), L=PPh$_3$: Cu$_2$I$_2$(Ph$_2$P(iBupy))$_2$(PPh$_3$)(46)

The compound 46 is a yellow, fine-crystalline solid.

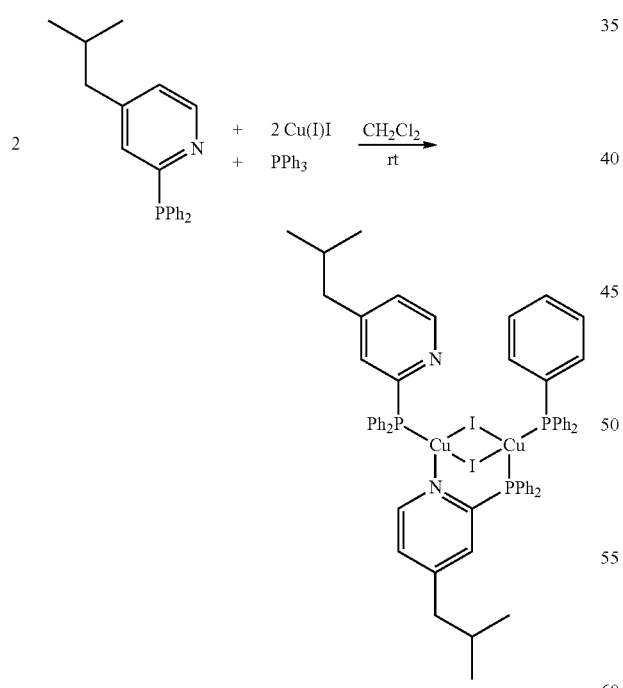

Characterization:
Elemental Analysis:
found: C 54.55; H 4.52; N 1.89
(with ½ molecule DCM)
calc.: C 54.87; H 4.57; N 2.12

XXXVII. P∩N*=(Ph$_2$PPyraz), L=PPh$_3$: Cu$_2$I$_2$(Ph$_2$PPyraz)(PPh$_3$)$_2$ (47)

The compound 47 is an orange-colored, fine-crystalline solid.

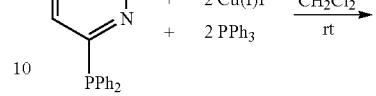

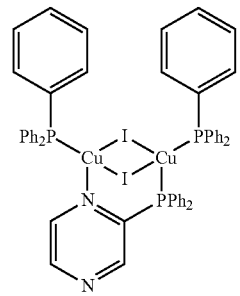

Characterization:
Elemental Analysis:
found: C 52.63; H 3.72; N 2.15
(with ¼ molecule DCM)
calc.: C 52.69; H 3.68; N 2.35

XXXVIII. P∩N*=(Ph$_2$PAlkoxyPy), L=PPh$_3$: Cu$_2$I$_2$(Ph$_2$PAlkoxyPy)(PPh$_3$)$_2$ (48)

The compound 48 is a yellow, fine-crystalline solid.

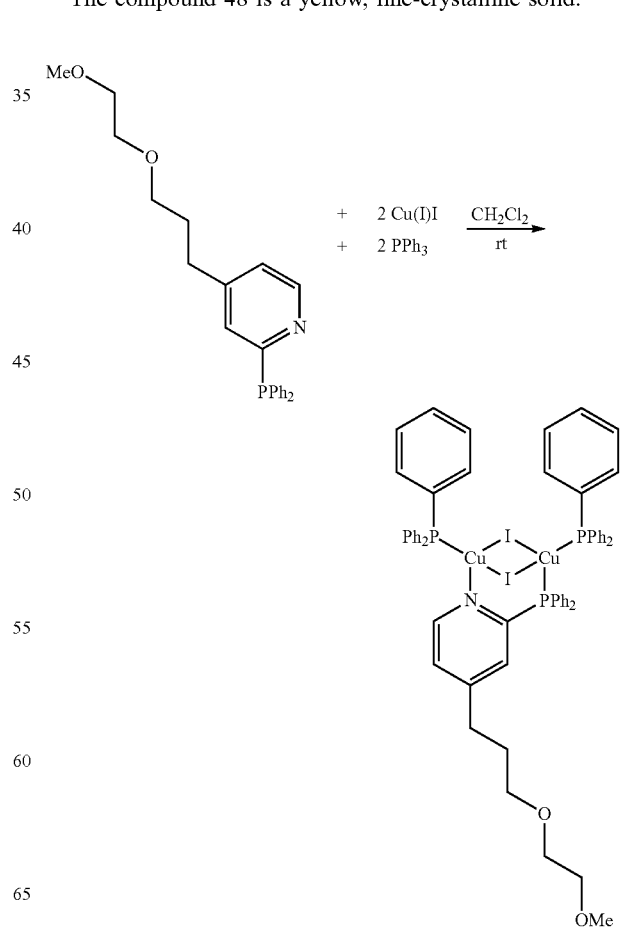

49

Characterization:
Elemental Analysis:
found: C 54.75; H 4.34; N 0.74
calc.: C 55.15; H 4.39; N 1.09

XXXIX. P∩N*=(Ph$_2$PAlkoxyPy), L=Ph$_2$PPAlkoxy: Cu$_2$I$_2$((Ph$_2$PAlkoxyPy)(Ph$_2$PPAlkoxy)$_2$ (49)

The compound 49 is a yellow solid.

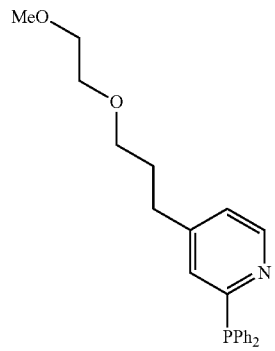

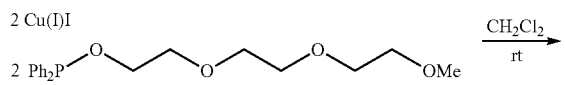

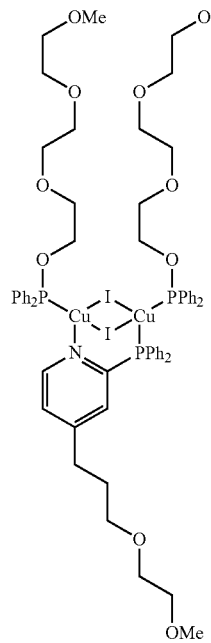

Characterization:
Elemental Analysis:
found: C 48.14; H 4.85; N 0.88
(with 1 molecule DCM)
calc.: C 48.29; H 5.10; N 0.91

50

L. P∩N*=Ph$_2$P(TolMeBenzimide), L=PPh$_3$: Cu$_2$I$_2$(Ph$_2$P(TolMeBenzimide)(PPh$_3$)$_2$ (50)

The compound 50 is a white, fine-crystalline solid.

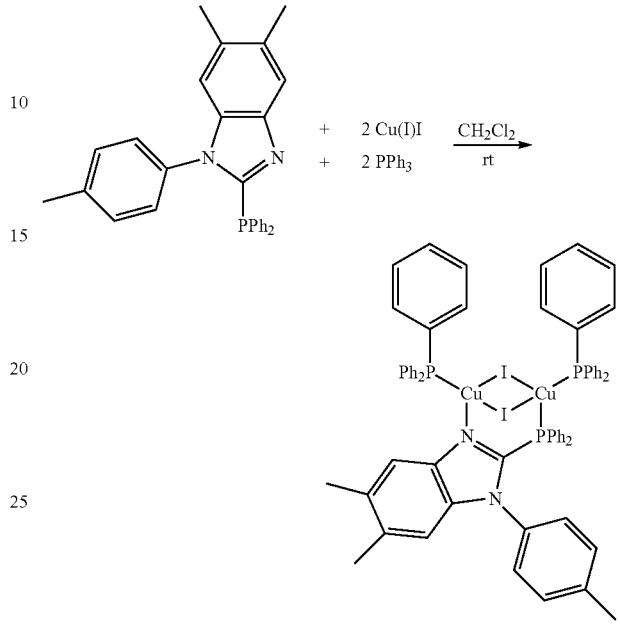

Characterization:
Elemental Analysis:
found: C 57.96; H 4.32; N 1.80
calc.: C 57.97; H 4.18; N 2.11

LI. P∩N*=Ph$_2$P(TolImide), L=PPh$_3$: Cu$_2$I$_2$(Ph$_2$P(TolImide)(PPh$_3$)$_2$ (51)

The compound 51 is a white, fine-crystalline solid.

Characterization:
Elemental Analysis:
found: C 55.13; H 4.05; N 1.81
(with ¼ molecule DCM)
calc.: C 55.13; H 3.93; N 2.21

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

REFERENCES

[i] C. Adachi, M. A. Baldo, S. R. Forrest, S. Lamansky, M. E. Thompson, R. C. Kwong, *Appl. Phys. Lett.* 2001, 78, 1622.
[ii] X. H. Yang, D. C. Müller, D. Neher, K. Meerholz, *Adv. Mater.* 2006, 18, 948; X. H. Yang, D. Neher, *Appl. Phys. Lett.* 2004, 84, 2476.
[iii] J. Shinar (Hrsg.), *Organic light-emitting devices—A survey*, AIP-Press, Springer, New York, 2004.
[iv] H. Yersin, *Top. Curr. Chem.* 2004, 241, 1.
[v] H. Yersin, *Highly Efficient OLEDs with Phosphorescent Materials*, Wiley-VCH, Weinheim 2008.
[vi] Z. H. Kafafi, *Organic Electroluminescence*, Taylor & Francis, Boca Raton, 2005.
[vii] M. E. Thompson, P. I. Djurovich, J. Li (University of Southern California, Los Angeles, Calif.), WO 2004/017043 A2, 2004.
[viii] M. E. Thompson, P. I. Djurovich, R. Kwong (University of Southern California, Los Angeles, Calif., Universal Display Corp, Ewing, N.Y.), WO 2004/016711 A1, 2004.
[ix] A. Tsuboyama, S. Okada, T. Takiguchi, K. Ueno, S. Igawa, J. Kamatani, M. Furugori, H. Iwawaki (Canon KK, Tokyo), WO 03/095587 A1, 2003.
[x] C.-M. Che, US 2003/0205707 A1, 2003.
[xi] C.-M. Che, W. Lu, M. C.-W. Chan, US 2002/0179885 A1, 2002.
[xii] J. Kamatani, S. Okada, A. Tsuboyama, T. Takiguchi, S. Igawa, US 2003/186080 A1, 2003.
[xiii] P. Stößel, I. Bach, A. Busing (Covion Organic Semiconductors GmbH), DE 10350606 A1, 2005.
[xiv] M. Bold, C. Lennartz, M. Egen, H.-W. Schmidt, M. Thelakkat, M. Bäte, C. Neuber, W. Kowalsky, C. Schildknecht (BASF AG), DE 10338550 A1, 2005.
[xv] C. Lennartz, A. Vogler, V. Pawlowski (BASF AG), DE 10358665 A1, 2005.
[xvi] B. Hsieh, T. P. S. Thorns, J. P. Chen (Canon KK, Tokyo), US 2006/989273 B2, 2006.
[xvii] N. Schulte, S. Heun, I. Bach, P. Stoessel, K. Treacher (Covion Organic Semiconductors), WO 2006/003000 A1, 2006.
[xviii] A. Vogler, V. Pawlowski, H.-W. Schmidt, M. Thelakkat (BASF AG), WO 2006/032449 A1, 2006.
[xix] T. K. Hatwar, J. P. Spindler, R. H. Young (Eastman Kodak Co), WO 2006/028546 A1, 2006.
[xx] P. C. Ford, E. Cariati, J. Bourassa, *Chem. Rev.* 1999, 99, 3625.
[xxi] H. Araki, K. Tsuge, Y. Sasaki, S. Ishizaka, N. Kitamura, *Inorg. Chem.* 2007, 46, 10032.
[xxii] A. Rössler, G. Skillas, S. E. Pratsinis, *Chemie in unserer Zeit* 2001, 35, 32.
[xxiii] Y. Sun, K. Ye, H. Zhang, J. Zhang, L. Zhao, B. Li, G. Yang, B. Yang, Y. Wang, S.-W. Lai, C.-M. Che, *Angew. Chem.* 2006, 118, 5738.
[xxiv] Y. Chen, J. F. Gerald, L. T. Chadderton, L. Chaffron, *Appl. Phys. Lett.* 1999, 74, 2782.

The invention claimed is:

1. A copper(I) complex comprising a structure of formula A:

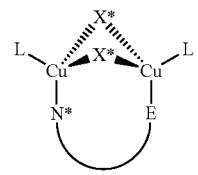

Formula A wherein
each X* is independently selected from Cl, Br, I, CN, OCN, SCN, alkynyl and $N_3$;
N*∩E is a bidentate ligand, wherein
E is selected from a phosphanyl group, an arsenyl group, and an antimonyl group of the form $R_2E$, wherein R is selected from alkyl, aryl, heteroaryl, alkoxyl, phenoxyl, and amide;
N* is an imine function which is part of an aromatic group selected from pyridazinyl, pyrimidyl, pyrazinyl, triazinyl, tetrazinyl, oxazolyl, thiazolyl, imidazolyl, pyrazolyl, isoxazolyl, isothiazolyl, 1,2,3-triazolyl, 1,2,4-triazolyl, 1,2,4-oxadiazolyl, 1,2,4-thiadiazolyl, tetrazolyl, 1,2,3,4-oxatriazolyl, 1,2,3,4-thiatriazole, chinoxalyl, and chinazolyl;
∩ is one carbon atom which is likewise part of the aromatic group, wherein the carbon atom is directly adjacent both to the imine nitrogen atom and to one of a phosphorus atom of the phosphanyl group, an arsenic atom of the arsenyl group, or an antimony atom of the antimonyl group; and
ligands L are each monodentate ligand in the form $DR_3$, wherein D is selected from P, As and Sb, wherein R is each independently selected from hydrogen, halogen, alkyl, heteroalkyl, aryl, alkenyl, alkynyl groups or substituted alkyl, heteroalkyl, aryl and alkenyl groups with substituents selected from halogens and deuterium, alkyl groups, heteroalkyl, aryl, heteroaryl and donor and acceptor groups selected from amines, carboxylates and their esters and $CF_3$ groups, wherein the alkyl group or the substituted alkyl group is optionally bound to D via an oxygen atom and wherein the three R groups optionally lead to annulated ring systems;
or
the ligands L are connected to each other via a bridge B such that a bidentate ligand in the form $R_2D$-B-$DR_2$ results, wherein D is selected from P, As and Sb, wherein the bridge B is a direct bond or a substituted or unsubstituted alkylene, alkenylene, alkynylene or arylene group or a combination of both, or —O—, —NR— or —$SiR_2$—, wherein R is each independently selected from hydrogen, halogen, alkyl, heteroalkyl, aryl, heteroaryl, alkenyl, alkynyl groups or substituted alkyl, heteroalkyl, aryl, heteroaryl and alkenyl groups with substituents selected from halogens and deuterium, alkyl groups, heteroalkyl, aryl, heteroaryl and donor and acceptor groups selected from amines, carboxylates and their esters and $CF_3$ groups, and wherein the alkyl or the substituted alkyl is optionally bound to D via an oxygen atom and wherein the two R groups optionally lead to annulated ring systems;
wherein ligand N*∩E comprises at least one substituent selected from the group consisting of:

branched, unbranched or cyclic alkyl chains with a length of C1 to C30;
branched, unbranched or cyclic alkoxy chains with a length of C1 to C30;
branched, unbranched or cyclic perfluoroalkyl chains with a length of C1 to C30; and
polyethers with a chain length of 5-50 repeat units.

2. The copper(I) complex of claim 1, wherein the ligand N*∩E is selected from the group consisting of

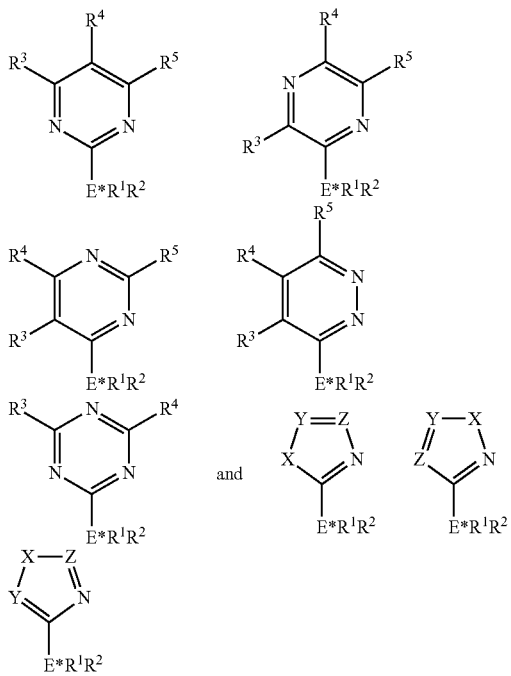

wherein
E* is selected from P, As and Sb;
X is selected from $NR^3$, O and S;
Y is selected from $CR^3$ and N;
Z is selected from $CR^4$ and N;
$R^1$, $R^2$ are each independently selected from alkyl, aryl, heteroaryl, alkoxyl, phenoxyl, and amide;
$R^3$-$R^5$ are each independently selected from hydrogen, halogen, alkyl, heteroalkyl, aryl, heteroaryl, alkenyl, alkynyl groups or substituted alkyl, heteroalkyl, aryl, heteroaryl and alkenyl groups with substituents selected from halogens and deuterium, alkyl groups, heteroalkyl, aryl, heteroaryl and donor and acceptor groups selected from amines, carboxylates and their esters and $CF_3$ groups; $R^3$-$R^5$ optionally lead to annulated ring systems;
wherein the ligand N*∩E comprises at least one of $R^1$-$R^5$ that comprises:
  a branched, unbranched or cyclic alkyl chain with a length of C1 to C30;
  a branched, unbranched or cyclic alkoxy chain with a length of C1 to C30;
  a branched, unbranched or cyclic perfluoroalkyl chain with a length of C1 to C30; and
  a polyether with a chain length of 5-50 repeat units;
wherein each D of the monodentate ligands in the form $DR_3$ or each D of the bidentate ligand $R_2D$-B-$DR_2$ is P;
wherein R of the monodentate ligands in the form $DR_3$ or R of the bidentate ligand $R_2D$-B-$DR_2$ is selected from hydrogen, halogen, alkyl, heteroalkyl, aryl, alkenyl, alkynyl groups or substituted alkyl, heteroalkyl, aryl and alkenyl groups with substituents selected from halogens or deuterium, alkyl groups, heteroalkyl, aryl, heteroaryl and further donor and acceptor groups selected from amines, carboxylates and their esters and $CF_3$ groups; wherein the alkyl or the substituted alkyl is optionally bound to D via an oxygen atom; the individual R groups optionally lead to annulated ring systems; and
wherein $R_2D$-B-$DR_2$ is selected from:

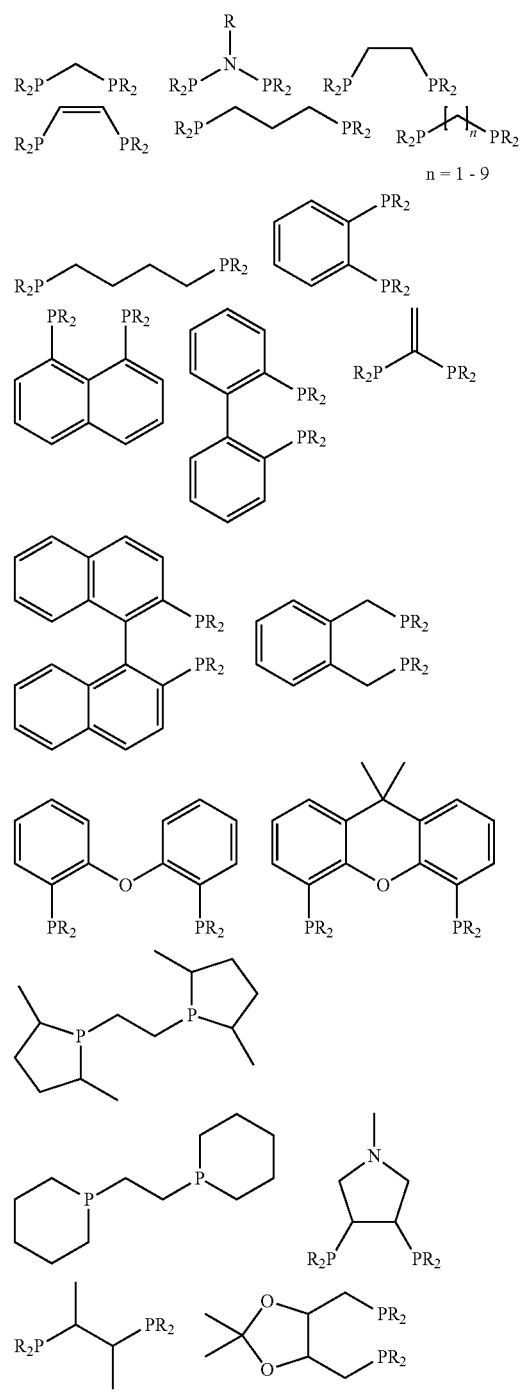

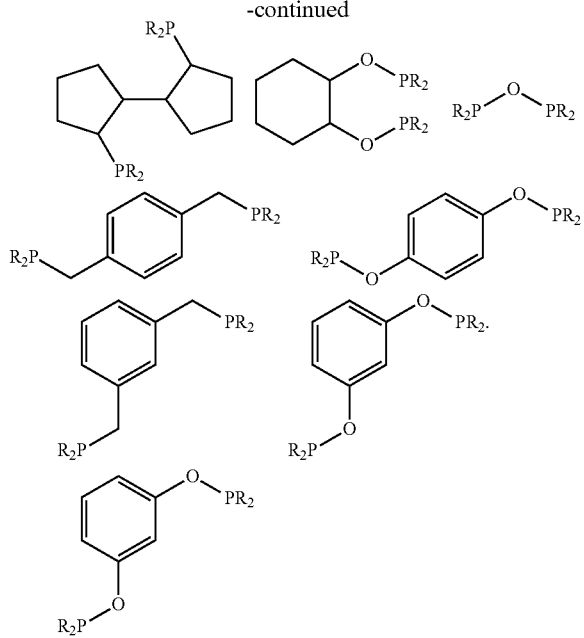

3. The copper(I) complex of claim 1, wherein at least one of the ligand N*∩E and the ligands L comprise at least one substituent selected from the group consisting of an electron conductor and a hole conductor.

4. The copper(I) complex of claim 1, wherein each X* is independently selected from Cl, Br, and I.

5. A method for the production of the copper(I) complex of claim 4, comprising conducting a reaction of the ligand N*∩E and the ligand L with Cu(I)X, wherein X is selected from Cl, Br, and I.

6. The method of claim 5, wherein the reaction is conducted in at least one of dichloromethane, acetonitrile, tetrahydrofuran, dimethylsulfoxide and ethanol.

7. The method of claim 6, further comprising the step of adding at least one of diethyl ether, pentane, hexane, methyl-tert-butyl ether, methanol, ethanol and water for obtaining the copper(I) complex in the form of a solid.

8. The method of claim 5, wherein the copper(I) complex is soluble in an organic solvent, wherein the organic solvent is selected from the group consisting of alcohols, ethers, alkanes, halogenated aliphatic hydrocarbons, aromatic hydrocarbons, and alkylated aromatic hydrocarbons.

9. The method of claim 5, further comprising the step of substituting at least one of the ligand N*∩E and the ligand L with at least one functional group for improving a charge carrier transport selected from an electron conductor and a hole conductor.

10. An optoelectronic component comprising at least one of:
    an emitter comprising the copper(I) complex of claim 1; and
    an absorber comprising the copper(I) complex of claim 1.

11. The optoelectronic component of claim 10, wherein the optoelectronic component is one of:
    an organic light emitting diode (OLED);
    a light emitting electrochemical cell;
    a OLED sensor;
    an organic solar cell;
    an organic field-effect transistor;
    an organic laser; and
    a down-conversion element.

12. An optoelectronic device comprising the copper(I) complex of claim 1, wherein the optoelectronic device is in the form of a component selected from the group consisting of an organic light emitting component, an organic diode, an organic solar cell, an organic transistor, an organic light emitting diode, a light emitting electrochemical cell, an organic field-effect transistor and an organic laser.

13. A method for the production of an optoelectronic component, wherein the copper(I) complex of claim 1 is applied to a carrier by a wet-chemical process, a colloidal suspension process, or a sublimation process.

14. A process for altering at least one of an emission property and an absorption property of an electronic component, wherein the copper(I) complex of claim 1 is introduced into a matrix material for conduction of electrons or holes in an optoelectronic component.

15. A method for using the copper(I) complex of claim 1, wherein the copper(I) complex is used in an optoelectronic component for conversion of UV radiation or of blue light to visible light, and wherein the visible light is green, yellow or red light.

* * * * *

UNITED STATES PATENT AND TRADEMARK OFFICE
CERTIFICATE OF CORRECTION

PATENT NO. : 9,985,225 B2  
APPLICATION NO. : 14/357805  
DATED : May 29, 2018  
INVENTOR(S) : Baumann et al.

Page 1 of 1

It is certified that error appears in the above-identified patent and that said Letters Patent is hereby corrected as shown below:

In the Specification

Column 10, Line 33, after "substitutions at the" please delete "spa-carbon" and insert --sp³-carbon--

In the Claims

Claim 1, Column 52, Line 36, after "ligands L are each" insert --a--

Claim 2, Column 55, Line 20, delete redundant chemical compound at end of the claim as follows:

" 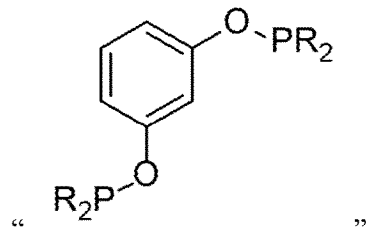 "

Signed and Sealed this  
Thirty-first Day of July, 2018

Andrei Iancu  
*Director of the United States Patent and Trademark Office*